(12) United States Patent
Paderi et al.

(10) Patent No.: US 11,896,642 B2
(45) Date of Patent: *Feb. 13, 2024

(54) BIOCONJUGATES WITH CHEMICALLY MODIFIED BACKBONES

(71) Applicant: Symic Holdings, Inc., San Francisco, CA (US)

(72) Inventors: John Eric Paderi, San Francisco, CA (US); Glenn Prestwich, San Francisco, CA (US); Katherine Allison Stuart, San Francisco, CA (US); Harsha Kabra, San Francisco, CA (US); Elvis Ikwa, Palo Alto, CA (US)

(73) Assignee: Symic Holdings, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/629,183

(22) PCT Filed: Jul. 9, 2018

(86) PCT No.: PCT/US2018/041280
§ 371 (c)(1),
(2) Date: Jan. 7, 2020

(87) PCT Pub. No.: WO2019/010490
PCT Pub. Date: Jan. 10, 2019

(65) Prior Publication Data
US 2021/0290726 A1    Sep. 23, 2021

Related U.S. Application Data

(60) Provisional application No. 62/530,066, filed on Jul. 7, 2017.

(51) Int. Cl.
*A61K 47/61* (2017.01)
*A61K 47/64* (2017.01)
(Continued)

(52) U.S. Cl.
CPC .............. *A61K 38/16* (2013.01); *A61K 38/08* (2013.01); *A61K 38/10* (2013.01); *A61K 47/61* (2017.08); *A61K 47/64* (2017.08)

(58) Field of Classification Search
CPC ........ A61K 38/16; A61K 47/61; A61K 47/64; A61K 38/08; A61K 38/10
(Continued)

(56) References Cited

U.S. PATENT DOCUMENTS

| 6,051,701 | A  | 4/2000 | Cialdi et al. |
| 8,846,003 | B2 | 9/2014 | Panitch et al. |

(Continued)

FOREIGN PATENT DOCUMENTS

| WO | WO-2010129547 | 11/2010 |
| WO | WO-2012112767 | 8/2012 |

(Continued)

OTHER PUBLICATIONS

Sampaio et al. Heparins and heparan sulfates Structure, distribution and protein interactions, Insights into Carbohydrate Structure and Biological Function: ISBN: 81-7895-243-2 Editor: Hugo Verli (Year: 2006).*

(Continued)

*Primary Examiner* — Kevin S Orwig
*Assistant Examiner* — John Michael Cronin
(74) *Attorney, Agent, or Firm* — Sheppard Mullin Richter & Hampton LLP

(57) ABSTRACT

Provided herein are synthetic bioconjugates comprising collagen-binding peptides covalently bound to chemically modified glycan backbones, compositions containing the same, and uses thereof.

8 Claims, 12 Drawing Sheets

Specification includes a Sequence Listing.

(51) Int. Cl.
*A61K 38/10* (2006.01)
*A61K 38/16* (2006.01)
*A61K 38/08* (2019.01)

(58) Field of Classification Search
USPC ........................................................ 514/21.2
See application file for complete search history.

(56) References Cited

U.S. PATENT DOCUMENTS

| | | | |
|---|---|---|---|
| 9,173,919 | B2 | 11/2015 | Paderi et al. |
| 9,200,039 | B2 | 12/2015 | Panitch et al. |
| 9,217,016 | B2 | 12/2015 | Panitch et al. |
| 9,512,192 | B2 | 12/2016 | Panitch et al. |
| 9,872,887 | B2 | 1/2018 | Panitch et al. |
| 10,689,425 | B2 | 6/2020 | Panitch et al. |
| 10,772,931 | B2 | 9/2020 | Panitch et al. |
| 10,828,370 | B2 | 11/2020 | Panitch et al. |
| 2012/0100106 | A1 | 4/2012 | Panitch et al. |
| 2014/0288002 | A1* | 9/2014 | Panitch .................. A61K 38/14 514/17.1 |
| 2015/0031619 | A1* | 1/2015 | Panitch .................. C07K 9/001 514/13.8 |
| 2015/0038427 | A1 | 2/2015 | Panitch et al. |
| 2016/0166654 | A1 | 6/2016 | Paderi et al. |
| 2016/0222064 | A1 | 8/2016 | Panitch et al. |
| 2016/0331841 | A1 | 11/2016 | Prestwich et al. |
| 2017/0112941 | A1 | 4/2017 | Panitch et al. |
| 2017/0283458 | A1 | 10/2017 | Panitch et al. |
| 2017/0368192 | A1 | 12/2017 | Paderi et al. |
| 2019/0330276 | A1 | 10/2019 | Panitch et al. |
| 2020/0078469 | A1 | 3/2020 | Prestwich et al. |
| 2020/0222548 | A1 | 7/2020 | Paderi et al. |
| 2021/0188915 | A1 | 6/2021 | Panitch et al. |

FOREIGN PATENT DOCUMENTS

| | | | |
|---|---|---|---|
| WO | WO-2012162534 | | 11/2012 |
| WO | WO-2016061145 | | 4/2016 |
| WO | WO-2016061147 | | 4/2016 |
| WO | WO-2016065083 | | 4/2016 |
| WO | WO-2016065083 A1 * | 4/2016 | ............ A61K 31/727 |
| WO | WO-2016111651 A1 * | 7/2016 | ............ A61K 31/727 |
| WO | WO-2016161333 | | 10/2016 |
| WO | WO-2016168743 | | 10/2016 |
| WO | WO-2017066349 | | 4/2017 |
| WO | WO-2019010484 | | 1/2019 |
| WO | WO-2019010485 | | 1/2019 |

OTHER PUBLICATIONS

Extended European Search Report for European Patent Application 18827869.1 dated Mar. 24, 2021. 13 pages.

Hempel et al., Artificial extracellular matrices composed of collagen I and sulfated hyaluronan with adsorbed transforming growth factor β1 promote collagen synthesis of human mesenchymal stromal cells. Acta Biomaterialia 2011, vol. 8, No. 2, pp. 659-666, XP028123827.

Hintze et al., Sulfated hyaluronan and chondroitin sulfate derivatives interact differently with human transforming growth factor-β1 (TGF-β1). Acta Biomaterialia 2012, vol. 8, No. 6, pp. 2144-2152, XP028480436.

Jiang et al., Targeting Heparin to Collagen within Extracellular Matrix Significantly Reduces Thrombogenicity and Improves Endothelialization of Decellularized Tissues. Biomacromolecules 2016, vol. 17, No. 12, pp. 3940-3948, XP055592025.

Koehler et al., Sulfated Hyaluronan Derivatives Modulate TGF-Æ1:Receptor Complex Formation: Possible Consequences for TGF-β1 Signaling. Scientific Reports 2017, vol. 7, No. 1, XP055780190. Retrieved from the Internet: www.nature.com/articles/s41598-017-01264-8.

Van der Smissen et al., Artificial extracellular matrix composed of collagen I and highly sulfated hyaluronan interferes with TGFb1 signaling and prevents TGFb1-induced myofibroblast differentiation. Acta Biomaterialia 2013, vol. 9, pp. 7775-7786, XP055780186. Retrieved from the Internet: josorge.com/publications/Citations/Hepatol/014.pdf.

International Search Report and Written Opinion for International Application No. PCT/US2018/041280 dated Oct. 15, 2018. (12 pages).

Schuppan et al., Matrix as a Modulator of Hepatic Fibrogenesis, Seminars in Liver Disease, vol. 21, No. 3, 2001, pp. 351-372.

Stuart et al., Collagen-Binding Peptidoglycans Inhibit MMP Mediated Collagen Degradation and Reduce Dermal Scarring. PLoS ONE 2011, vol. 6, Issue 7; e22139. (8 pages).

* cited by examiner

SEQUENCE LISTING

<160> NUMBER OF SEQ ID NOS: 85

<210> SEQ ID NO 1
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Ala Asn Ala Ala Leu Lys Ala Gly Glu Leu Tyr Lys Ser Ile
1               5                   10                  15

Leu Tyr

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Glu Leu Tyr Lys Ser Ile Leu Tyr
1               5

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Ala Asn Ala Ala Leu Lys Ala Gly Glu Leu Tyr Lys Cys Ile
1               5                   10                  15

Leu Tyr

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Leu Tyr Lys Cys Ile Leu Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Leu Asp Gly Asn Glu Ile Lys Arg
1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Ala His Glu Glu Ile Ser Thr Thr Asn Glu Gly Val Met
1               5                   10

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Gly Val Phe Lys Tyr Arg Pro Arg Tyr Phe Leu Tyr Lys His Ala
1               5                   10                  15

Tyr Phe Tyr Pro Pro Leu Lys Arg Phe Pro Val Gln
            20                  25

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Gln Asp Ser Glu Thr Arg Thr Phe Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Lys Lys Thr Leu Arg Thr
1               5

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Arg Ser Lys Ser Lys Lys Phe Arg Arg Pro Asp Ile Gln Tyr
1               5                   10                  15

Pro Asp Ala Thr Asp Glu Asp Ile Thr Ser His Met
            20                  25

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Ser Gln Asn Pro Val Gln Pro
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Tyr Ile Arg Ile Ala Asp Thr Asn Ile Thr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Glu Leu Asn Leu Val Tyr Thr
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Thr
1

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ser Ile Thr Thr Ile Asp Val Pro Trp Asn Val
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gln Leu Tyr Lys Ser Ile Leu Tyr
1               5

<210> SEQ ID NO 17
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Gly Gln Leu Tyr Lys Ser Ile Leu Tyr Gly Ser Gly Ser Gly Ser Arg
1               5                   10                  15

Arg

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Ala Asn Ala Ala Leu Lys Ala Gly Gln Leu Tyr Lys Ser Ile
1               5                   10                  15

Leu Tyr

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Leu Thr Tyr Thr Trp Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Leu Thr Tyr Thr Trp Ser Gly Ser Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Leu Trp Val Leu Pro Lys
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

Trp Arg Glu Pro Ser Phe Cys Ala Leu Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (16)..(16)
<223> OTHER INFORMATION: Biphenylalanine

<400> SEQUENCE: 23

Ala Trp His Cys Thr Thr Lys Phe Pro His His Tyr Cys Leu Tyr Xaa
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (17)..(17)
<223> OTHER INFORMATION: Biphenylalanine

<400> SEQUENCE: 24

Ala His Lys Cys Pro Trp His Leu Tyr Thr Thr His Tyr Cys Phe Thr
1               5                   10                  15

Xaa

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Alanine

<400> SEQUENCE: 25

Ala His Lys Cys Pro Trp His Leu Tyr Thr His Tyr Cys Phe Thr
1               5                   10                  15

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

```
<400> SEQUENCE: 26

Gly Arg Pro Gly Glu Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 27

Gly Met Pro Gly Glu Arg
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 28

Gly Leu Pro Gly Glu Asn
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 29

Gly Leu Pro Gly Glu Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Leu Lys Gly Glu Asn
1               5

<210> SEQ ID NO 31
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline

<400> SEQUENCE: 31

Gly Phe Pro Gly Glu Arg Gly Val Glu Gly Pro Pro Gly Pro Ala
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Val Trp Met Gln Ala Pro Gly Gly Gly Lys
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Tyr Arg Gly Arg Leu
1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Thr Cys Ser Gly Asp Glu Tyr Thr Trp His Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Thr Cys Val Gly Asp His Lys Thr Trp Lys Cys
1               5                   10

<210> SEQ ID NO 36
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 36

Gln Trp His Cys Thr Thr Arg Phe Pro His His Tyr Cys Leu Tyr Gly
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Thr Trp Thr Trp Asn Gly Ser Ala Trp Thr Trp Asn Glu Gly Gly
1               5                   10                  15

Lys

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Thr Trp Thr Trp Asn Gly Thr Asn Trp Thr Arg Asn Asp Gly Gly
1               5                   10                  15

Lys

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Val Trp Leu Trp Glu Gln Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Val Trp Leu Trp Glu Asn Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Cys Met Thr Ser Pro Trp Arg Cys
1               5
```

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Cys Pro Gly Arg Val Met His Gly Leu His Leu Gly Asp Asp Glu Gly
1               5                   10                  15

Pro Cys
```

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Lys Leu Trp Leu Leu Pro Lys
1               5
```

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Leu Ser Glu Leu Arg Leu His Glu Asn
1               5
```

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Leu Thr Glu Leu His Leu Asp Asn Asn
1               5
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Leu Ser Glu Leu Arg Leu His Asn Asn
1               5
```

<210> SEQ ID NO 47
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 47

Leu Ser Glu Leu Arg Leu His Ala Asn
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Arg Glu Leu His Leu Asn Asn Asn
1               5

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 50
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Ile Val Ile Glu Leu Gly Thr Asn Pro Leu Lys Ser Ser Gly Ile
1               5                   10                  15

Glu Asn Gly Ala Phe Gln Gly Met Lys Lys
            20                  25

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Glu Leu Asn Leu Val Tyr
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 52

Asp Ala Arg Lys Ser Glu Val Gln Lys
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Val Trp Met Gln Ala Pro
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Trp Gly Ser Leu Arg Ala
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Biphenylalanine

<400> SEQUENCE: 55

Gly Lys Trp His Cys Thr Thr Lys Phe Pro His His Tyr Cys Leu Tyr
1               5                   10                  15

Xaa

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Val Met His Gly Leu His Leu Gly Asp Asp Glu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(12)
<223> OTHER INFORMATION: D-amino acid

<400> SEQUENCE: 57

Glu Asp Asp Gly Leu His Leu Gly His Met Val Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Val Met His Gly Leu His Leu Gly Asn Asn Gln
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 59

Gln Asn Asn Gly Leu His Leu Gly His Met Val Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gln Leu Tyr Lys Ser Ile Leu Tyr Gly Ser Gly
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ser Gly Gln Leu Tyr Lys Ser Ile Leu Tyr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

```
Gly Ser Gly Gly Gln Leu Tyr Lys Ser Ile Leu Tyr
1               5                   10
```

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Lys Gln Leu Asn Leu Val Tyr Thr
1               5
```

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Cys Val Trp Leu Trp Gln Gln Cys
1               5
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Trp Arg Glu Pro Ser Phe Ser Ala Leu Ser
1               5                   10
```

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25
```

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gly His Arg Pro Leu Asn Lys Lys Arg Gln Gln Ala Pro Ser Leu Arg
1               5                   10                  15

Pro Ala Pro Pro Pro Ile Ser Gly Gly Gly Tyr Arg
            20                  25
```

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Ile Leu Tyr
1

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Ala Asn Ala Ala Leu Lys Ala Gly Glu Leu Tyr Lys Ser Ile
1               5                   10                  15

Leu Tyr Gly Ser Gly
            20

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly
1

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Gly Gly
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Gly Cys
1

<210> SEQ ID NO 73
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 73

Gly Ser Gly Ser Gly
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ser Gly Ser Gly Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Gly Arg Arg
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Gly Ser Arg Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ser Gly Ser Gly Arg Arg
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ser Gly Ser Gly Ser Arg Arg
1               5
```

```
<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This region may encompass 0-5 residues

<400> SEQUENCE: 79

Lys Lys Lys Lys Lys Gly Ser Gly
1               5

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Gly Ser Gly
1

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Gly Lys Arg Arg Gly Ser Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Lys Gly Ser Gly
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Lys Lys Gly Ser Gly
1               5

<210> SEQ ID NO 84
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 84

Gly Glu Leu Tyr Lys Ser Ile Leu Tyr Gly Ser Gly
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Arg Arg Gly Ser Gly
1               5
```

BIOCONJUGATES WITH CHEMICALLY MODIFIED BACKBONES

CROSS-REFERENCE TO RELATED APPLICATIONS

This application is a U.S. National Stage Application under 35 U.S.C. § 371 of International Application No. PCT/US2018/041280, filed Jul. 9, 2018, which application claims the benefit under 35 U.S.C. § 119(e) to U.S. Provisional Patent Application No. 62/530,066, filed Jul. 7, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 20, 2018, is named 38FE-253694-WO_SL.txt and is 21,963 bytes in size.

FIELD

Provided herein are synthetic bioconjugates comprising collagen-binding peptides covalently bound to chemically modified glycan backbones, compositions containing the same, and uses thereof.

BACKGROUND

In tissues, cells are surrounded by an extracellular matrix (ECM) containing various macromolecules, such as bioconjugates, collagen, hyaluronic acid, laminin, fibronectin, etc. In mammals, bioconjugates are a major component of the extracellular matrix, where they form large complexes, both to other bioconjugates, to hyaluronic acid, and to fibrous matrix proteins (such as collagen). As mammals age, sustain wounds and in some disease states, the extracellular matrix in certain areas of the body (e.g., in synovial joints, the vitreous humor, the spinal discs, the skin, etc.) can be lost or degrade, causing undesirable symptoms. In addition, some tissue injuries, such as vascular injury, corneal injury and wounds, result in the exposure of the extracellular matrix and/or components thereof, including collagen.

SUMMARY

Surprisingly, the bioconjugates described herein are poorly metabolized as they are not found to be substrates for GAG degradation enzymes, and they have been found to target the liver while having an extended half-life with decreased renal clearance when compared to non-sulfated derivatives. The present disclosure provides bioconjugates comprising at least one peptide(s), wherein the peptide(s) comprises a collagen-binding unit covalently bonded to a chemically sulfated glycan.

Also provided are compositions comprising the bioconjugates described herein, and methods of use thereof. In one aspect, provided are compositions comprising the bioconjugates as described herein, where the number peptides bound to the glycan varies. For example, the composition can comprise bioconjugates where the number of peptides bound thereto is calculated as an average, such as from about 50 to about 150 peptides per glycan.

Also provided are pharmaceutical compositions comprising the bioconjugates described herein or compositions containing the same and one or more diluent or carrier (such as saline).

The bioconjugates, and compositions comprising the same, as described herein can be used to for treating fibrosis in a patient in need thereof, including, but not limited to, pulmonary fibrosis, cystic fibrosis, idiopathic pulmonary fibrosis, renal fibrosis, liver fibrosis (such as liver fibrosis as a result of chronic alcohol exposure, hepatitis B virus (HBV) infection, non-alcoholic fatty liver disease (NAFLD), Non-alcoholic steatohepatitis (NASH), hepatitis C virus (HCV) infection, Wilson's disease, alpha-1-antitrypsin deficiency, hemochromatosis, primary biliary cirrhosis, primary sclerosing cholangitis, or autoimmune hepatitis), cirrhosis, cardiac fibrosis, atrial fibrosis, endomyocardial fibrosis, myocardial infarction, glial scar, arthrofibrosis, Crohn's disease, Dupuytren's contracture, keloid, mediastinal fibrosis, myelofibrosis, Peyronie's disease, nephrogenic systemic fibrosis, progressive massive fibrosis, retroperitoneal fibrosis, scleroderma, systemic sclerosis and adhesive capsulitis.

Also provided herein is a method for making a bioconjugate as described herein, comprising contacting a chemically sulfated glycan with at least one peptide(s), wherein the peptide(s) comprises a collagen-binding unit, optionally in the presence of an activating agent, under coupling reaction conditions to provide the bioconjugate. In certain embodiments, the method first comprises providing the chemically sulfated glycan by contacting a glycan with a sulfating agent under reaction conditions sufficient to provide the chemically sulfated glycan.

BRIEF DESCRIPTION OF THE DRAWINGS

Certain aspects of the present disclosure can be viewed by the accompanying figures. Included are the following.

DETAILED DESCRIPTION

Figure 1:
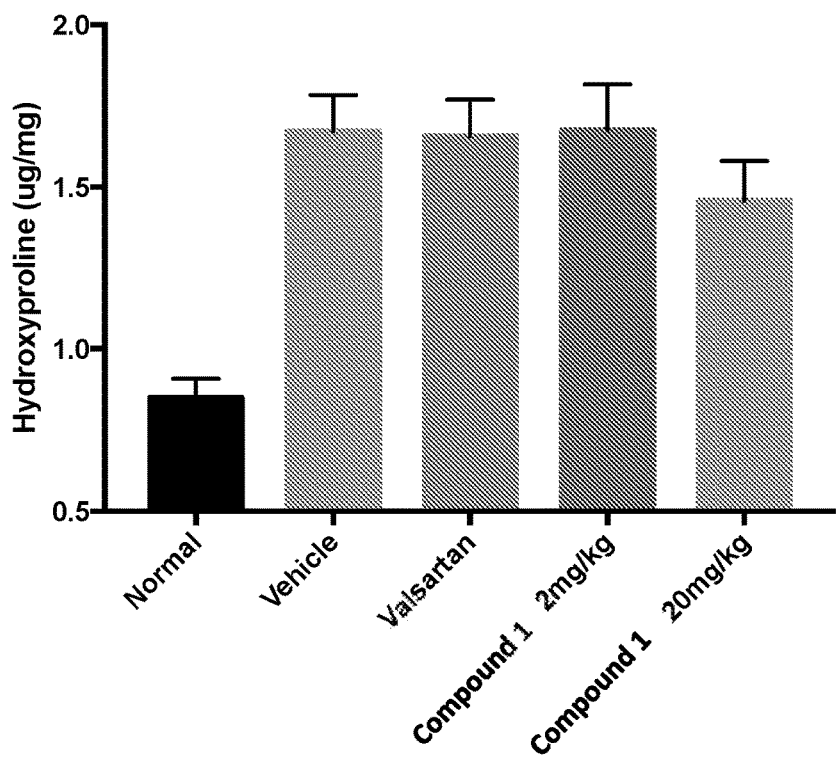
FIG. 1 shows the hydroxyproline content in the liver for two doses of Compound 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

1. Definitions

Unless defined otherwise, all technical and scientific terms used herein have the same meaning as commonly understood by one of ordinary skill in the art to which this disclosure belongs. It must be noted that as used herein and in the appended claims, the singular forms "a", "an", and "the" include plural referents unless the context clearly dictates otherwise. Thus, for example, reference to "a peptide" includes a plurality of peptides.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the terms "bioconjugate," "peptidoglycan," and "proteoglycan," and "synthetic bioconjugate" are used interchangeably and refer to a synthetic conjugate that comprises chemically sulfated glycan having one or more peptides covalently bonded thereto.

As used herein, the term "chemically sulfated glycan" refers to a compound having a large number of monosaccharides linked glycosidically, which has been chemically modified to include sulfate moieties. In certain embodiments, the glycan is a glycosaminoglycan (GAG), which comprises 2-aminosugars linked in an alternating fashion with uronic acids, and include polymers such as heparin, heparan sulfate, chondroitin, keratin, and dermatan. Accordingly, non-limiting examples of glycans which can be used in the embodiments described herein include alginate, agarose, dextran, dextran sulfate, chondroitin, chondroitin sulfate (CS), dermatan, dermatan sulfate (DS), heparan sulfate, heparin (Hep), keratin, keratan sulfate, and hyaluronic acid (HA), including derivatives thereof. In another embodiment, the molecular weight of the glycan is varied to tailor the effects of the bioconjugate (see e.g., Radek, K. A., et al., Wound Repair Regen., 2009, 17: 118-126; and Taylor, K. R., et al., J. Biol. Chem., 2005, 280:5300-5306). In one embodiment, the glycan is degraded by oxidation and alkaline elimination (see e.g., Fransson, L. A., et al., Eur. J. Biochem., 1980, 106:59-69) to afford degraded glycan having a lower molecular weight (e.g., from about 10 kDa to about 50 kDa). In another embodiment, the glycan is degraded enzymatically, by heat, by ultrasound, by ozonolysis, by shearing, or by other methods known to depolymerize and reduce the molecular weight of the glycan. In certain embodiments, the glycan does not contain oxidatively cleaved saccharide rings and thus does not, and has not, contain(ed) aldehyde functional groups.

As used herein, the terms "bonded" and "covalently bonded" can be used interchangeably and refer to the sharing of one or more pairs of electrons by two atoms.

In one embodiment, the bioconjugates of the disclosure bind, either directly or indirectly to collagen. The terms "binding" or "bind" as used herein are meant to include interactions between molecules that may be detected using, for example, a hybridization assay, surface plasmon resonance, ELISA, competitive binding assays, isothermal titration calorimetry, phage display, affinity chromatography, rheology or immunohistochemistry. The terms are also meant to include "binding" interactions between molecules. Binding may be "direct" or "indirect." "Direct" binding comprises direct physical contact between molecules. "Indirect" binding between molecules comprises the molecules having direct physical contact with one or more molecules simultaneously. This binding can result in the formation of a "complex" comprising the interacting molecules. A "complex" refers to the binding of two or more molecules held together by covalent or non-covalent bonds, interactions or forces.

As used herein, the term "extracellular matrix" refers to the extracellular part of tissue that provides structural and biochemical support to the surrounding cells.

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution. As used herein, the term "topically"

refers to administering a composition non-systemically to the surface of a tissue and/or organ (internal or, in some cases, external) to be treated, for local effect.

As used herein, the term "pharmaceutically acceptable" indicates that the indicated material does not have properties that would cause a reasonably prudent medical practitioner to avoid administration to a patient, taking into consideration the amount used and/or the disease or conditions to be treated and the respective route of administration. Typical pharmaceutically acceptable materials are essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the internal surface of a vein.

As used herein, the term "formulated" or "formulation" refers to the process in which different chemical substances, including one or more pharmaceutically active ingredients, are combined to produce a dosage form. In certain embodiments, two or more pharmaceutically active ingredients can be coformulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to routes, approaches, formulations, technologies, and systems for transporting a pharmaceutical composition in the body as needed to safely achieve its desired therapeutic effect. The route of delivery can be any suitable route, including but not limited to, intravascular, intravenous, intraarterial, intramuscular, cutaneous, subcutaneous, percutaneous, intradermal, and intraepidermal routes.

As used herein, the term "solution" refers to solutions, suspensions, emulsions, drops, ointments, liquid wash, sprays, and liposomes, which are well known in the art. In some embodiments, the liquid solution contains an aqueous pH buffering agent which resists changes in pH when small quantities of acid or base are added. In certain embodiments, the liquid solution contains a lubricity enhancing agent.

As used herein, the term "treating" refers to preventing, curing, reversing, attenuating, alleviating, minimizing, inhibiting, suppressing and/or halting one or more clinical symptoms of a disease or disorder prior to, during, and/or after a vascular injury or intervention.

2. Bioconjugates

The present disclosure provides bioconjugates comprising at least one peptide(s), wherein the peptide(s) comprises a collagen-binding unit covalently bonded to a chemically sulfated glycan. Surprisingly, the bioconjugates described herein are poorly metabolized as they are not found to be substrates for GAG degradation enzymes, and they have been found to target the liver while having an extended half-life with decreased renal clearance when compared to non-sulfated derivatives.

The chemically sulfated glycan which can be used in the embodiments described herein can be any chemically sulfated glycan (e.g., a glycosaminoglycan (GAG)). Non limiting examples include a chemically sulfated alginate, a chemically sulfated chondroitin, a chemically sulfated chondroitin sulfate, a chemically sulfated dermatan, a chemically sulfated heparan, a chemically sulfated heparosan, a chemically sulfated heparan sulfate, a chemically sulfated heparin, a chemically sulfated dextran, a chemically sulfated dextran sulfate, a chemically sulfated hyaluronic acid, or a derivative thereof. In one embodiment, the chemically sulfated glycan is a chemically sulfated heparosan, or a derivative thereof. In one embodiment, the chemically sulfated glycan is a chemically sulfated dextran, or a derivative thereof. In one embodiment, the chemically sulfated glycan is a chemically sulfated hyaluronic acid, or a derivative thereof.

In certain embodiments, the chemically sulfated glycan has been further derivatized, which can take place prior to or after the sulfation. In certain embodiments, the glycan has been derivatized to comprise carboxymethyl substituents prior to the sulfation step. Accordingly, in certain embodiments, the chemically sulfated glycan is chemically sulfated carboxymethyl alginate, a chemically sulfated carboxymethyl chondroitin, a chemically sulfated carboxymethyl chondroitin sulfate, a chemically sulfated carboxymethyl dermatan, a chemically sulfated carboxymethyl heparan, a chemically sulfated carboxymethyl heparosan, a chemically sulfated carboxymethyl heparan sulfate, a chemically sulfated carboxymethyl heparin, a chemically sulfated carboxymethyl dextran, a chemically sulfated carboxymethyl dextran sulfate, a chemically sulfated carboxymethyl hyaluronic acid, or a derivative thereof.

In certain embodiments, the chemically sulfated glycan is a chemically sulfated heparosan, a chemically sulfated carboxymethyl heparosan, a chemically sulfated dextran, a chemically sulfated carboxymethyl dextran, a chemically sulfated hyaluronic acid, a chemically sulfated carboxymethyl hyaluronic acid, or a derivative thereof.

The degree of sulfation on the glycan can vary depending on the starting glycan and the desired properties of the final bioconjugate. In certain embodiments, the glycan has a degree of sulfation of from about 0.5 to about 4, or from about 0.5 to about 3.9, or greater than about 0.5, or about 0.6, or about 0.7, or about 0.8, or about 0.9, or about 1.0, or about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.4, or about 3.5, or about 3.6, or about 3.7, or about 3.8, or about 3.9, or about 4. The degree of sulfation can be calculated by methods known in the art (see, e.g., Example 1 and Biomacromolecules, 2009, 10, 3290-3297).

In certain embodiments, the chemically sulfated glycan comprises from about 0.25 to about 4, from about 0.5 to about 3, from about 2 to about 3, from about 0.5 to about 2.5, or from about 0.5 to about 2 sulfate moieties per disaccharide, or about 0.5, or about 0.6, or about 0.7, or about 0.8, or about 0.9, or about 1.0, or about 1.1, or about 1.2, or about 1.3, or about 1.4, or about 1.5, or about 1.6, or about 1.7, or about 1.8, or about 1.9, or about 2.0, or about 2.1, or about 2.2, or about 2.3, or about 2.4, or about 2.5, or about 2.6, or about 2.7, or about 2.8, or about 2.9, or about 3.0, or about 3.1, or about 3.2, or about 3.3, or about 3.4, or about 3.5, or about 3.6, or about 3.7, or about 3.8, or about 3.9, or about 4 sulfate moieties per disaccharide. In embodiments where the glycan does not contain conventional "disaccharide units" (e.g., alginic acid), the chemically sulfated glycan typically comprises from about 0.25 to about 0.75, or about 0.3, or about 0.4, or about 0.5, or about 0.6, or about 0.7, or about 0.75, or about 0.8, or about 0.85, or about 0.9, or about 0.95, or about 1, or about 1.25, or about 1.5, or about 1.75, or about 2 sulfate moieties per monosaccharide.

Various molecular weights for the glycan can be used in the bioconjugates described herein, however, it is contemplated that a higher molecular weight would provide certain benefits, such as an increased half-life. In some embodiments, the molecular weight of the chemically sulfated glycan is from about 5 to about 1000 kDa. In some embodiments, the chemically sulfated glycan is at least about 20, or about 25, or about 30, or about 35, about 40, or about 45, or about 50, or about 100, or about 150, or about 200, or about 250, or about 300, or about 350, or about 400, or about 450, or about 500, or about 550, or about 600, or about 650, or about 700, or about 750, or about 800, or about 850, or about 900, or about 950, or about 1000 kDa. In some embodiments, the chemically sulfated glycan has a molecular weight greater than about 150 kDa. In some embodiments, the chemically sulfated glycan has a molecular weight of from about 150 to about 750 kDa. In some embodiments, the chemically sulfated glycan has a molecular weight of from about 150 to about 350 kDa. In some embodiments, the chemically sulfated glycan has a molecular weight of from about 200 to about 400 kDa. In certain embodiments, the glycan does not contain oxidatively cleaved saccharide rings and thus does not, and has not, contain(ed) aldehyde functional groups.

In one embodiment, the bioconjugate comprises a peptide having a collagen-binding unit which binds to one or more of collagen type I, II, III, IV, V, VI, VII, VIII, IX, X, XI, XII, XIII, or XIV. In one embodiment, the collagen-binding unit promotes or inhibits fibrillogenesis upon binding to collagen. In one embodiment, the collagen-binding unit does not promote or inhibit fibrillogenesis upon binding to collagen. In some embodiments, the peptide binds to type I collagen. In other embodiments, the peptide binds to type IV collagen. In certain embodiments, one or more peptide(s) having a specified binding affinity for collagen can be used in the bioconjugates described herein. For example, the synthetic bioconjugates can comprise at least one peptide which has binding affinity to type I collagen and at least one peptide which has binding affinity to type IV collagen. In another embodiment, the peptides have binding affinity to type I collagen. In another embodiment, the peptides have binding affinity to type IV collagen. In certain embodiments, the peptides have binding affinity to type II collagen. In certain embodiments, the peptides have binding affinity to type III collagen. In certain embodiments, the peptide binds to more than one type of collagen, where the relative affinity to each collagen type may vary. In one embodiment, the bioconjugate binds to collagen with a dissociation constant ($K_d$) of less than about 1 mM, or less than about 900 µM, or less than about 800 µM, or less than about 700 µM, or less than about 600 µM, or less than about 500 µM, or less than about 400 µM, or less than about 300 µM, or less than about 200 µM, or less than about 100 µM.

Further, the bioconjugates described herein may comprise peptides with more than one binding unit, where the binding unit can be the same or different. For example, in certain embodiments, the peptide comprises two or more collagen-binding units, where the collagen-binding units are the same. In another embodiment, the peptide comprises two or more collagen-binding units, where the collagen-binding units are different.

Depending on the desired properties of the bioconjugate, the total number of peptides bonded to the glycan can be varied. In certain embodiments, the total number of peptides present in the bioconjugate is from about 50 to about 250, or from about 50 to about 150, or from about 75 to about 125, or about 50, or about 60, or about 70, or about 80, or about 90, or about 100, or about 110, or about 120, or about 130, or about 140, or about 150, or about 160, or about 170, or about 180, or about 190, or about 200, or about 210, or about 220, or about 230, or about 240, or about 250 peptides per glycan.

The peptides as used herein can be linear or branched and typically comprise from 1 to about 120 amino acids and have at least one collagen-binding units (or sequences). In one embodiment, the peptide comprises from about 3 to about 120 amino acids, or from about 3 to about 110 amino acids, or from about 3 to about 100 amino acids, or from about 3 to about 90 amino acids, or from about 3 to about 80 amino acids, or from about 3 to about 70 amino acids, or from about 3 to about 60 amino acids, or from about 3 to about 50 amino acids, or from about 3 to about 40 amino acids, or from about 5 to about 120 amino acids, or from about 5 to about 100 amino acids, or from about 5 to about 90 amino acids, or from about 5 to about 80 amino acids, or from about 5 to about 70 amino acids, or from about 5 to about 60 amino acids, or from about 5 to about 50 amino acids, or from about 5 to about 40 amino acids, or from about 5 to about 30 amino acids, or from about 5 to about 20 amino acids, or from about 5 to about 10 amino acids. These peptides may also be referred to as "collagen-binding peptides". As used herein, the term "collagen-binding unit" is intended to refer to an amino acid sequence within a peptide which binds to collagen. "Collagen-binding" indicates an interaction with collagen that could include hydrophobic, ionic (charge), and/or Van der Waals interactions, such that the compound binds or interacts favorably with collagen. This binding (or interaction) is intended to be differentiated from covalent bonds and nonspecific interactions with common functional groups, such that the peptide would interact with any species containing that functional group to which the peptide binds on the collagen. Peptides can be tested and assessed for binding to collagen using any method known in the art. See, e.g., Li, Y., et al., Current Opinion in Chemical Biology, 2013, 17: 968-975, Helmes, B. A., et al., J. Am. Chem. Soc. 2009, 131, 11683-11685, and Petsalaki, E., et al., PLoS Comput Biol, 2009, 5(3): e1000335. In one embodiment, the peptide, or the collagen-binding unit of the peptide, binds to collagen with a dissociation constant (Kd) of less than about 1 mM, or less than about 900 µM, or less than about 800 µM, or less than about 700 µM, or less than about 600 µM, or less than about 500 µM, or less than about 400 µM, or less than about 300 µM, or less than about 200 µM, or less than about 100 µM.

Collagen-binding peptide can bind to one or more of collagen type I, II, III, IV, V, VI, VII, VIII, IX, X, XI, XII, XIII, or XIV. In some embodiments, the collagen-binding peptides bind to type IV collagen, which can be intact, cleaved or degraded. In some embodiments, the collagen-binding peptides bind to type I or III collagen, which can be intact, cleaved or degraded.

In various embodiments, the peptides that bind to type I or III collagen include an amino acid sequence selected from RRANAALKAGELYKSILY (SEQ ID NO: 1), GELYKSILY (SEQ ID NO: 2), RRANAALKAGELYKCILY (SEQ ID NO: 3), GELYKCILY (SEQ ID NO: 4), RLDGNEIKR (SEQ ID NO: 5), AHEEISTTNEGVM (SEQ ID NO: 6), NGVFKYRPRYFLYKHAYFYPPLKRFPVQ (SEQ ID NO: 7), CQDSETRTFY (SEQ ID NO: 8), TKKTLRT (SEQ ID NO: 9), GLRSKSKKFRRPDIQYPDATDEDITSHM (SEQ ID NO: 10), SQNPVQP (SEQ ID NO: 11), SYIRIADTNIT (SEQ ID NO: 12), KELNLVYT (SEQ ID NO: 13), GSIT (SEQ ID NO: 14), GSITTIDVPWNV (SEQ ID NO: 15), GQLYKSILY (SEQ ID NO: 16), GQLYKSILYGSGSGSRR (SEQ ID NO: 17), RRANAALKAGQLYKSILY (SEQ ID NO: 18), or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In one embodiment, peptides that bind to type I or III collagen include an amino acid sequence RRANAALKAGELYKSILY (SEQ ID NO: 1) or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In one embodiment, peptides that bind to type I or III collagen include an amino acid sequence GELYKSILY (SEQ ID NO: 2) or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In one embodiment, peptides that bind to type I or III collagen include an amino acid sequence GQLYKSILY (SEQ ID NO: 16) or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In one embodiment, peptides that bind to type I or III collagen include an amino acid sequence GQLYKSILYGSGSGSRR (SEQ ID NO: 17) or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

In one embodiment, peptides that bind to type I or III collagen include an amino acid sequence RRANAALKAGQLYKSILY (SEQ ID NO: 18) or a sequence having at least about 80% sequence identity, or at least about 83% sequence identity, or at least about 85% sequence identity, or at least about 90% sequence identity, or at least about 95% sequence identity, or at least about 98% sequence identity thereto, provided the sequence is capable of binding to collagen.

A non-limiting example of collagen-binding units that bind type IV collagen is TLTYTWS (SEQ ID NO: 19) which binds specifically to MMP 2 and 9-degraded basement membrane type IV collagen. Likewise, TLTYTWSGSG (SEQ ID NO: 20) which further includes a GSG linker can also bind to cleaved or degraded type IV collagen specifically. Another example is KLWVLPK (SEQ ID NO: 21) which selectively binds to intact type IV collagen.

In certain embodiments, the peptide comprises an amino acid sequence that has at least about 80%, or at least about 83%, or at least about 85%, or at least about 90%, or at least about 95%, or at least about 98%, or at least about 100% sequence identity with the collagen-binding domain(s) of the von Willebrand factor (vWF) or a platelet collagen receptor as described in Chiang, T. M., et al. J. Biol. Chem., 2002, 277: 34896-34901, Huizinga, E. G. et al., Structure, 1997, 5: 1147-1156, Romijn, R. A., et al., J. Biol. Chem., 2003, 278: 15035-15039, and Chiang, et al., Cardio. & Haemato. Disorders-Drug Targets, 2007, 7: 71-75, each incorporated herein by reference. A non-limiting example is WREPSFCALS (SEQ ID NO: 22), derived from vWF.

Various methods for screening peptide sequences for collagen-binding affinity (or a collagen-binding domain/unit) are routine in the art. Other peptide sequences shown to have collagen-binding affinity (or a collagen-binding unit) which can be used in the bioconjugates and methods disclosed herein include but are not limited to, βAWHCTTKFPHHYCLYBip (SEQ ID NO: 23), βAHKCPWHLYTTHYCFTBip (SEQ ID NO: 24), βAHKCPWHLYTHYCFT (SEQ ID NO: 25), etc., where Bip is biphenylalanine and βA is beta-alanine (see, Abd-Elgaliel, W. R., et al., Biopolymers, 2013, 100(2), 167-173), GROGER (SEQ ID NO: 26), GMOGER (SEQ ID NO: 27), GLOGEN (SEQ ID NO: 28), GLOGER (SEQ ID NO: 29), GLKGEN (SEQ ID NO: 30), GFOGERGVEGPOGPA (SEQ ID NO: 31), etc., where O is 4-hydroxyproline (see, Raynal, N., et al., J. Biol. Chem., 2006, 281(7), 3821-3831), HVWMQAPGGGK (SEQ ID NO: 32) (see, Helms, B. A., et al., J. Am. Chem. Soc. 2009, 131, 11683-11685), WREPSFCALS (SEQ ID NO: 22) (see, Takagi, J., et al., Biochemistry, 1992, 31, 8530-8534), WYRGRL (SEQ ID NO: 33), etc. (see, Rothenfluh D. A., et al., Nat Mater. 2008, 7(3), 248-54), WTCSGDEYTWHC (SEQ ID NO: 34), WTCVGDHKTWKC (SEQ ID NO: 35), QWHCTTRFPHHYCLYG (SEQ ID NO: 36), etc. (see, U.S. 2007/0293656), STWTWNGSAWTWNEGGK (SEQ ID NO: 37), STWTWNGTNWTRNDGGK (SEQ ID NO: 38), etc. (see, WO/2014/059530), CVWLWEQC (SEQ ID NO: 39) cyclic CVWLWENC (SEQ ID NO: 40), cyclic CVWLWEQC (SEQ ID NO: 39), (see, Depraetere H., et al., Blood. 1998, 92, 4207-4211, and Duncan R., Nat Rev Drug Discov, 2003, 2(5), 347-360), CMTSPWRC (SEQ ID NO: 41), etc. (see, Vanhoorelbeke, K., et al., J. Biol. Chem., 2003, 278, 37815-37821), CPGRVMHGLHLGDDEGPC (SEQ ID NO: 42) (see, Muzzard, J., et al., PLoS one. 4 (e 5585) I-10), KLWLLPK (SEQ ID NO: 43) (see, Chan, J. M., et al., Proc Natl Acad Sci U.S.A., 2010, 107, 2213-2218), and CQDSETRTFY (SEQ ID NO: 8), etc. (see, U.S. 2013/0243700), H-V-F/W-Q/M-Q-P/A-P/K (Helms, B. A., et al., J. Am. Chem. Soc., 2009, 131(33), 11683-11685), wherein each is hereby incorporated by reference in its entirety.

Additional peptide sequences shown to have collagen-binding affinity (or a collagen-binding unit) which can be used in the bioconjugates and methods disclosed herein include but are not limited to, LSELRLHEN (SEQ ID NO: 44), LTELHLDNN (SEQ ID NO: 45), LSELRLHNN (SEQ ID NO: 46), LSELRLHAN (SEQ ID NO: 47), and LRELHLNNN (SEQ ID NO: 48) (see, Fredrico, S., Angew. Chem. Int. Ed. 2015, 37, 10980-10984).

Additional peptide sequences shown to have collagen-binding affinity (or a collagen-binding unit) which can be used in the bioconjugates and methods disclosed herein include but are not limited to, RRANAALKAGELYKSILYGC (SEQ ID NO: 49), MIVIELGTNPLKSSGIENGAFQGMKK (SEQ ID NO: 50), KELNLVY (SEQ ID NO: 51), DARKSEVQK (SEQ ID NO: 52), HVWMQAP (SEQ ID NO: 53), HWGSLRA (SEQ ID NO: 54) (see, Hendra Wahyudi et al., J Control Release. 2016, 240, 323-331), and GKWH[CTTKFPHHYC]LYBip-CONH2 (SEQ ID NO: 55), where Bip is biphenylalanine (see, Wei Chen et al., JACC Cardiovasc Imaging. 2013, 6(3): 373-384).

In certain embodiments, the peptides include one or more sequences selected from the group consisting of RVMHGLHLGDDE (SEQ ID NO: 56), D-amino acid EDDGLHLGHMVR (SEQ ID NO: 57), RVMHGLHLGNNQ (SEQ ID NO: 58), D-amino acid QNNGLHLGHMVR (SEQ ID NO: 59), RVMHGLHLGNNQ (SEQ ID NO: 58), (GQLYKSI-LYGSG)$_4$K$_2$K (core peptide disclosed as SEQ ID NO: 60) (a 4-branch peptide), GSGQLYKSILY (SEQ ID NO: 61), GSGGQLYKSILY (SEQ ID NO: 62), KQLNLVYT (SEQ ID NO: 63), CVWLWQQC (SEQ ID NO: 64), WREPSFSALS (SEQ ID NO: 65), GHRPLDKKREE-APSLRPAPPPISGGGYR (SEQ ID NO: 66), and GHR-PLNKKRQQAPSLRPAPPPISGGGYR (SEQ ID NO: 67).

Similarly for a collagen-binding peptide, a peptide derived from a phage display library selected for collagen can be generated. The peptide can be synthesized and evaluated for binding to collagen by any of the techniques such as SPR, ELISA, ITC, affinity chromatography, or others known in the art. An example could be a biotin modified peptide sequence (e.g., SILYbiotin (SEQ ID NO: 68)) that is incubated on a microplate containing immobilized collagen. A dose response binding curve can be generated using a streptavidin-chromophore to determine the ability of the peptide to bind to collagen.

In one embodiment, the peptides comprise one or more collagen-binding units which binds any one or more of collagen type I, III or IV. In one embodiment, the peptide binds to type I collagen with a dissociation constant (Kd) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type III collagen with a dissociation constant (Kd) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type IV collagen with a dissociation constant (Kd) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM. In one embodiment, the peptide binds to type IV collagen with a dissociation constant (Kd) of less than about 1 mM, or less than about 900 μM, or less than about 800 μM, or less than about 700 μM, or less than about 600 μM, or less than about 500 μM, or less than about 400 μM, or less than about 300 μM, or less than about 200 μM, or less than about 100 μM.

In any of the embodiments described herein, the peptide collagen-binding unit, comprises any amino acid sequence described in the preceding paragraphs or an amino acid sequence having at least about 80%, or at least about 83%, or at least about 85%, or at least about 90%, or at least about 95%, or at least about 98%, or at least about 100% homology to any of these amino acid sequences. In various embodiments, the peptide components of the bioconjugates described herein can be modified by the inclusion of one or more conservative amino acid substitutions. As is well-known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure. Likewise, the present disclosure also includes sequences that have one, two, three, four, or five substitution, deletion or addition of amino acid residues as compared to the reference sequences. In certain embodiments, in any one or more of the sequences specified herein, the sequence may be modified by having one, two, or three amino addition, deletion and/or substitution each therefrom.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

The peptide(s) can be bonded to the glycan directly or via a linker. In some embodiments, the linker can be any suitable bifunctional linker, e.g., N-[β-maleimidopropionic acid]hydrazide (BMPH), 3-(2-pyridyldithio)propionyl hydrazide (PDPH), and the like. In any of the various embodiments described herein, the sequence of the peptide may be modified to include a glycine-cysteine (GC) attached to the C-terminus of the peptide and/or a glycine-cysteine-glycine (GCG) attached to the N-terminus to provide an attachment point for a glycan or a glycan-linker conjugate. In certain embodiments, the linker is N-[β-maleimidopropionic acid] hydrazide (BMPH). In certain embodiments, the linker is 3-(2-pyridyldithio)propionyl hydrazide (PDPH).

Depending on the desired properties of the bioconjugate, the total number of peptides bonded to the glycan can be varied. In certain embodiments, the total number of peptides present in the bioconjugate is from about 50 to about 200, or from about 50 to about 160, or from about 50 to about 160, or from about 50 to about 160, or from about 50 to about 160, or from about 50 to about 150, or from about 50 to about 140, or from about 60 to about 120, or from about 70 to about 110, or from about 80 to about 110, or from about 90 to about 110, or about 50, or about 60, or about 70, or about 80, or about 90, or about 100, or about 110, or about 120, or about 130, or about 140, or about 150, or about 160, or about 170, or about 180, or about 190, or about 200. In other embodiments, the bioconjugate comprises from about 5 to about 200 peptides. In various embodiments, the bioconjugate comprises from about 4 to about 180 peptides. In certain embodiments, the bioconjugate comprises less than about 200 peptides. In certain embodiments, the bioconjugate comprises less than about 180 peptides. In certain embodiments, the bioconjugate comprises less than about 150 peptides. In certain embodiments, the bioconjugate comprises less than about 100 peptides.

In any of the embodiments described herein, the number of peptides per glycan is an average, where certain bioconjugates in a composition may have more peptides per glycan and certain bioconjugates have less peptides per glycan. Accordingly, in certain embodiments, the number of peptides as described herein is an average in a composition of bioconjugates. For example, in certain embodiments, the bioconjugates are a composition where the average number of peptides per glycan is about 50 or greater than about 50. In other embodiments, the average number of peptides per glycan is about 60, or about 70, or about 80, or about 90, or about 100, or about 110, or about 120, or about 130, or about 140, or about 150, or about 160, or about 170, or about 180, or about 190, or about 200, or about 250, or about 300.

In certain embodiments, the number of peptides per glycan may be described as a "percent (%) functionalization" based on the percent of disaccharide units which are functionalized with peptide on the glycan backbone. For example, the total number of available disaccharide units present on the glycan can be calculated by dividing the molecular weight (or the average molecular weight) of a single disaccharide unit (e.g., about 550-800 Da, or from about 650-750 Da) by the molecular weight of the glycan (e.g., about 25 kDa up to about 70 kDa, or even about 100 kDa). In embodiments where the glycan does not contain conventional "disaccharide units" (e.g., alginic acid), the total number of available disaccharide units present on the glycan to be used in the calculations presented herein, can be calculated by dividing the molecular weight (or the average molecular weight) of a single saccharide unit by the molecular weight of the glycan, and multiplying by 2.

Therefore, in certain embodiments, the glycan comprises from about 1 to about 50, or from about 5 to about 30% functionalization with peptides, or from about 10 to about 30% functionalization with peptides, or about 20% functionalization with peptides, wherein the percent (%) functionalization with peptides is determined by a percent of disaccharide units on the glycan which are functionalized with peptide. In some embodiments, the percent (%) functionalization of the glycan with peptides is from about 1% to about 50%, or from about 3% to about 40%, or from about 5% to about 30%, or from about 10% to about 30%, or about 5%, or about 10%, or about 15%, or about 20%, or about 25%, or about 30%, or about 35%, or about 40%, or about 45%, or about 50%.

In certain embodiments, provided is a composition comprising a bioconjugate as described herein and peptide, where the peptide is closely associated (e.g., via ionic bonding) to the bioconjugate. In certain embodiments, a bioconjugate aggregate may be formed thereby. It is contemplated that the bioconjugate aggregate (comprising bioconjugate and non-covalently bound peptide) may comprise from 1% to 200% functionalization with peptides (determined by a percent of disaccharide units on the glycan which are functionalized with peptide). In some embodiments, the percent (%) functionalization with peptides in the bioconjugate aggregate is from about 1% to about 50%, or from about 3% to about 40%, or from about 5% to about 30%, or from about 10% to about 20%, or about 1%, or about 2%, or about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 100%.

In one embodiment, the bioconjugate used in the methods described above comprises heparin and from about 50 to about 150, or about 100, peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17) and are bound to the heparin via a hydrazide-carbonyl linkage. In certain embodiments, the heparin is unfractionated heparin (UFH) or low molecular weight heparin (LMWH).

In one embodiment, the bioconjugate used in the methods described above comprises heparin and from about 15 to about 30% functionalization with peptides, wherein the peptides comprise at least one sequence of RRANAALKAGELYKSILY (SEQ ID NO: 1) RRANAALKAGELYKSILYGSG (SEQ ID NO: 69), GQLYKSILY (SEQ ID NO: 16), or GQLYKSILYGSGSGSRR (SEQ ID NO: 17) and are bound to the heparin via a hydrazide-carbonyl linkage.

In one embodiment, the bioconjugate used in the methods described above comprises heparin and from about 15 to about 30% functionalization with peptides, wherein the peptides comprise at least one sequence of: GQLYKSILY (SEQ ID NO: 16), GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom. In certain embodiments, the bioconjugate comprises at least two different collagen-binding units.

The peptide can be synthesized and evaluated for binding to collagen by any of the techniques such as SPR, ELISA, ITC, affinity chromatography, or others known in the art. An example could be a biotin modified peptide sequence (e.g., SILYbiotin (SEQ ID NO: 68)) that is incubated on a microplate containing immobilized collagen. A dose response binding curve can be generated using a streptavidin-chromophore to determine the ability of the peptide to bind to collagen. In various embodiments described herein, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid which has been replaced. Non-conservative substitutions may too be possible, provided that they do not substantially affect the binding activity of the peptide (i.e., collagen-binding affinity).

Therefore, in some embodiments, peptides are bound to glycans, such as dermatan sulfate, by utilizing oxidation chemistry to cleave one or more of the saccharide ring within the glycan backbone in order to provide aldehyde binding sites on the glycan. The aldehyde binding sites are then used to conjugate the peptides (e.g., via a —C(O)—NH—N=C bond).

In some embodiments, the peptides can be covalently bound to glycan via a —C(O)—NH—NH—C(O)— (i.e. a hydrazide-carbonyl) linkage. Here, the peptides are bound to the glycan via a hydrazide-carbonyl linkage, where a carbonyl group of the hydrazide-carbonyl is an exocyclic carbonyl group present on the glycan. The exocyclic carbonyl group may be present on the native glycan, or alternatively, the glycan can be modified to include such a functional group. Such methods are further detailed below. It is contemplated that the beneficial effects exhibited by the bioconjugates as disclosed herein (such as increased binding affinity) is at least partially due to the glycan not containing oxidatively cleaved saccharide rings.

Accordingly, in certain embodiments, the peptides as described herein further comprise a hydrazide moiety for conjugation to the peptide. The hydrazide group can be bound to the peptide(s) at any suitable point of attachment, such as for example, the C-terminus, the N-terminus or via a side chain on an amino acid. For example, when a peptide is bound to the glycan via a side chain of an amino acid of the peptide, the side chain is glutamic acid or aspartic acid. The hydrazide can be formed between a hydrazine (—NHNH$_2$) bound to a carbonyl group present on an amino acid in the peptide sequence (e.g., a C-terminal carbonyl group) or to a spacer, if present.

In certain embodiments, the peptide(s) are bonded to the glycan (or the linker, if present) via a spacer. As used herein, the term "spacer" is intended to refer to an optional portion of the bioconjugate which links the peptide (or binding unit) to either the linker, when present, or the glycan (can be bound directly). In any of the embodiments described herein, any one or more of the peptides may have a linear or branched spacer sequence comprising from 1 to about 15 amino acids. In one embodiment, the spacer comprises one or more, or from 1 to 20, or from 10 to 20, or from 5 to 15, or from 5 to 10, or from 1 to 10, or from 1 to 5, or from 1 to 3, amino acids. It is contemplated that any amino acid, natural or unnatural, can be used in the spacer sequence, provided that the spacer sequence does not significantly interfere with the intended binding of the peptide. The amino acids are, in some instances, non-polar amino acids, such as alanine, cysteine, glycine, isoleucine, leucine, methionine, phenylalanine, proline, tryptophan, tyrosine and valine. In certain embodiments, the amino acids are selected from the group consisting of glycine, alanine, arginine and serine.

Exemplary spacers include, but are not limited to, short sequences comprising from one to five glycine units (e.g., G, GG, GGG, GGGG (SEQ ID NO: 70), or GGGGG (SEQ ID NO: 71)), optionally comprising cysteine (e.g., GC, GCG, GSGC (SEQ ID NO: 72), or GGC) and/or serine (e.g., GSG, SGG, GSGSG (SEQ ID NO: 73) or GSGSGS (SEQ ID NO: 74)), from one to five arginine units (e.g., R, RR, RRR, etc.), or a combination thereof (e.g., GSGRR (SEQ ID NO: 75), GSGSRR (SEQ ID NO: 76), GSGSGRR (SEQ ID NO: 77) or GSGSGSRR (SEQ ID NO: 78)). The spacer may also comprise non-amino acid moieties, such as polyethylene glycol (PEG), 6-aminohexanoic acid, succinic acid, or combinations thereof, with or without an additional amino acid spacer. In certain embodiments, the peptide sequences described herein further comprise a GSG-NHNH$_2$ moiety. Typically, the GSG-NHNH$_2$ moiety is bound to either the C- or N-terminus.

In certain embodiments, the spacer comprises more than one binding site (where the spacer may be linear or branched) such that more than one peptide sequence can be bound thereto, thus creating a branched construct. In addition, since the peptide can be bound to the glycan via a terminal or non-terminal amino acid moiety, the peptide will be branched when bound to the glycan via a non-terminal amino acid moiety. The binding sites on the spacer can be the same or different, and can be any suitable binding site, such as an amine or carboxylic acid moiety, such that a desired peptide sequence can be bound thereto (e.g. via an amide bond). Thus in certain embodiments, the spacer contains one or more lysine, glutamic acid or aspartic acid residues. In certain embodiments, the spacer comprises from 2 to 6 amino acids, or 3 or 4 amino acids. In certain embodiments, the spacer comprises one or more amino acid sequences of the formula KXX, where each X is independently a natural or unnatural amino acid. Specific examples of spacers which can be used alone or in combination to make branched constructs include, but are not limited to, KRR, KKK, (K)$_n$GSG (SEQ ID NO: 79), and (KRR)$_n$-KGSG (spacer peptide disclosed as SEQ ID NO: 80), where n is 0 to 5, or 1, 2, 3, 4, or 5. In one embodiment, the spacer is or GSGKRRGSG (SEQ ID NO: 81).

Such constructs can provide peptides having more than one unit of the formula P$_n$L, where at least one P is a collagen-binding unit, L is a spacer and n is an integer from 2 to about 10, or from 2 to 8, or from 2 to 6, or from 2 to 5, or from 2 to 4, or 2, or 3, or 4, or 5, or 6, or 7, or 8, or 9, or 10. For example, the spacer L can be an amino acid sequence such as KGSG (SEQ ID NO: 80), KKGSG (SEQ ID NO: 82, KKKGSG (core peptide disclosed as SEQ ID NO: 82), or KKKKGSG (SEQ ID NO: 83), etc., where peptides can be bound to the N-terminus and the side chain nitrogen, providing 2, 3, and 4 binding sites, respectively. A schematic of these spacers bound to peptides is shown in the table below.

| Spacer | Number of peptides (i.e., binding sites) | Structure of Spacer |
|---|---|---|
| KGSG (SEQ ID NO: 80) | 2 | 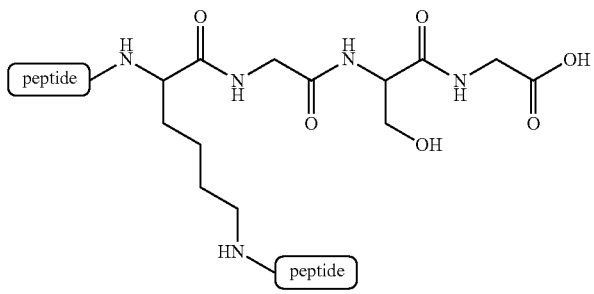 [SMILES: CNCCCCC(NC)C(=O)NCC(=O)NC(CO)C(=O)NCC(=O)O] |
| KKGSG (SEQ ID NO: 82) | 3 | 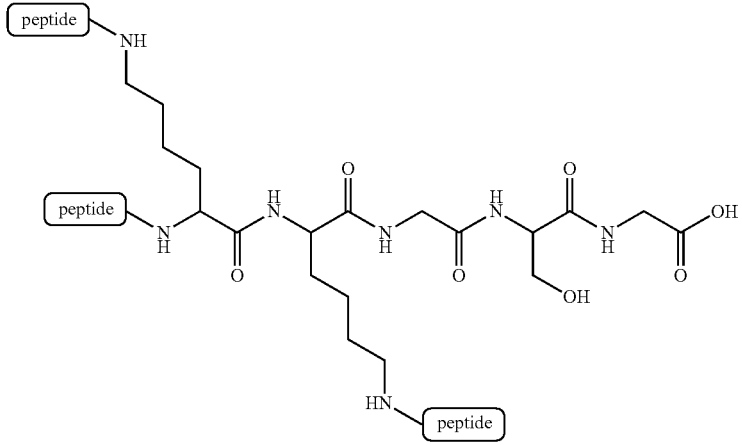 [SMILES: CNCCCCC(NC)C(=O)NC(CCCCNC)C(=O)NCC(=O)NC(CO)C(=O)NCC(=O)O] |
| KKKGSG (SEQ ID NO: 83) | 4 | 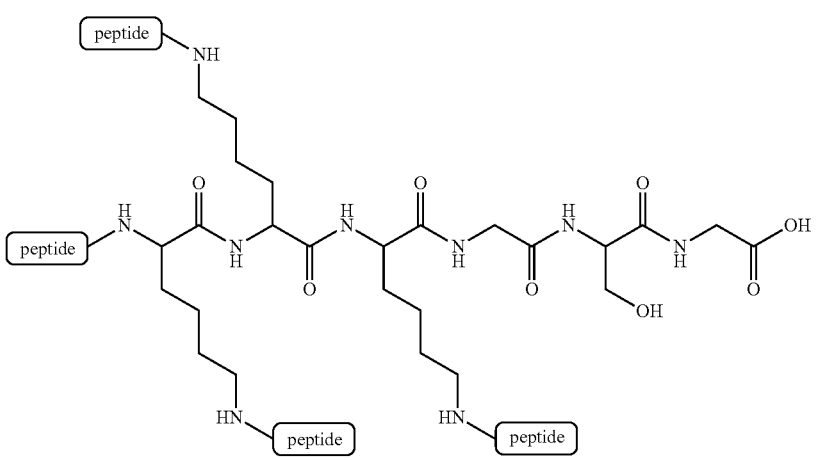 [SMILES: CNCCCCC(NC)C(=O)NC(CCCCNC)C(=O)NC(CCCCNC)C(=O)NCC(=O)NC(CO)C(=O)NCC(=O)O] |

| Spacer | Number of peptides (i.e., binding sites) | Structure of Spacer |
|---|---|---|
| K$_2$KGSG (core peptide disclosed as SEQ ID NO: 82) | 4 | (chemical structure showing four peptide groups attached via lysine branches to a KGSG backbone) |

In some embodiments, the peptide sequences are modified to replace one or more glutamic acid residue(s) with glutamine and/or one or more aspartic acid residue(s) with asparagine.

Exemplary branched collagen-binding constructs include, but are not limited to, (GELYKSILYGSG)$_2$K (core peptide disclosed as SEQ ID NO: 84), (GELYKSILYGSG)$_2$KGSG (core peptide disclosed as SEQ ID NO: 84 and spacer peptide disclosed as SEQ ID NO: 80), (GELYKSILYGSG)$_3$KK (core peptide disclosed as SEQ ID NO: 84), (GELYKSILYGSG)$_3$KKGSG (core peptide disclosed as SEQ ID NO: 84 and spacer peptide disclosed as SEQ ID NO: 82), (GELYKSILYGSG)$_4$KKK (core peptide disclosed as SEQ ID NO: 84), (GELYKSILYGSG)$_4$KKKGSG (core peptide disclosed as SEQ ID NO: 84 and spacer peptide disclosed as SEQ ID NO: 83), (GQLYKSILYGSG)$_2$K (core peptide disclosed as SEQ ID NO: 60), (GQLYKSILYGSG)$_2$KGSG (core peptide disclosed as SEQ ID NO: 60 and spacer peptide disclosed as SEQ ID NO: 80), (GQLYKSILYGSG)$_3$KK (core peptide disclosed as SEQ ID NO: 60), (GQLYKSILYGSG)$_3$KKGSG (core peptide disclosed as SEQ ID NO: 60 and spacer peptide disclosed as SEQ ID NO: 82), (GQLYKSILYGSG)$_4$K$_2$K (core peptide disclosed as SEQ ID NO: 60), (GQLYKSILYGSG)$_4$K$_2$KGSG (core peptide disclosed as SEQ ID NO: 60 and spacer peptide disclosed as SEQ ID NO: 82), (GQLYKSILYGSG)$_4$KKK (core peptide disclosed as SEQ ID NO: 60), (GQLYKSILYGSG)$_4$KKKGSG (core peptide disclosed as SEQ ID NO: 60 and spacer peptide disclosed as SEQ ID NO: 83), (GQLYKSILYGSG)$_4$-(KRR)$_2$-K (core peptide disclosed as SEQ ID NO: 60), and (GQLYKSILYGSG)$_4$-(KRR)$_2$-KGSG (core peptide disclosed as SEQ ID NO: 60 and spacer peptide disclosed as SEQ ID NO: 80).

In one embodiment, the hydrazide group is bonded to the C-terminus via a spacer comprising one or more amino acids selected from the group consisting of glycine, alanine, arginine and serine. In one embodiment, the spacer is selected from the group consisting of glycine, glycine-glycine, and glycine-serine-glycine. In various embodiments, the peptide comprises an amino acid spacer, such as glycine-serine-glycine (GSG), GSGSGSRR (SEQ ID NO: 78), KRRGSG (SEQ ID NO: 85), or GSGKRRGSG (SEQ ID NO: 81).

3. Synthesis of Bioconjugates

The peptides as used herein may be purchased from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

As shown below in Scheme 1, the bioconjugates described herein are synthesized from chemically sulfated glycan derivatives (e.g., sulfated hyaluronic acid). Various glycan derivatives suitable for use in the bioconjugates described herein can be prepared using methods known in the art, such via nucleophilic substitution of hydroxyls along the glycan backbone (see, e.g., Biomacromolecules, 2009, 10, 3290-3297). As shown in Scheme 1, glycan (e.g., hyaluronic acid) 1A can be reacted with a suitable sulfating agent, such as a SO₃/DMF complex, to provide one or more chemically sulfated glycan derivative(s) 1B. As is apparent to one of skill in the art, the chemically sulfated glycan derivative 1B can be tailored depending on the reagents and reaction conditions employed, such that partial, complete or a mixture of sulfated glycan derivative(s) 1B can be obtained. The chemically sulfated glycan derivative 1B can then be reacted with peptide, optionally in the presence of a coupling agent under typical peptide coupling reaction conditions to provide bioconjugate 1C.

As is typical in peptide coupling reactions, an activating agent may be used to facilitate the reaction. Suitable coupling agents (or activating agents) are known in the art and include for example, carbodiimides (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), tetramethylfluoroformamidinium hexafluorophosphate (TFFH), anhydrides (e.g., symmetric, mixed, or cyclic anhydrides), activated esters (e.g., phenyl activated ester derivatives, p-hydroxamic activated ester, hexafluoroacetone (HFA), etc.), acylazoles (acylimidazoles using CDI, acylbenzotriazoles, etc.), acyl azides, acid halides, phosphonium salts (BOP, AOP, PyAOP, BOP-Cl, Brop, PyBrop, PyOxim, HOBt, PyBOP, HOAt, etc.), EEDQ, IIDQ, CIP, DPPA, aminium/uronium salts (e.g., HATU, HBTU, COMU, tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), organophosphorus reagents (e.g., phosphinic and phosphoric acid derivatives), organosulfur reagents (e.g., sulfonic acid derivatives), triazine coupling reagents (e.g., 2-chloro-4,6-dimethoxy-1,3,5-triazine, 4-(4,6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like (see, e.g., El-Faham, et al. Chem. Rev., 2011, 111(11): 6557-6602; Han, et al. Tetrahedron, 2004, 60:2447-2467).

In one embodiment, the peptide coupling reaction proceeds via an activated glycan intermediate by reacting a carboxylic acid moiety of the glycan with a coupling agent (e.g., a carbodiimide reagent, such as but not limited to, N,N'-dicyclohexylcarbodiimide (DCC), N,N'-diisopropylcarbodiimide (DIC), 1-ethyl-3-(3-dimethylaminopropyl) carbodiimide (EDC), etc.) to form an O-acylisourea intermediate. Such carbodiimide chemistry is well known in the art and suitable coupling agents can be purchased from commercial sources. Contacting the O-acylisourea intermediate with the desired peptide yields the bioconjugate. The glycan can be contacted with activating agent prior to, or in the presence of, the peptide.

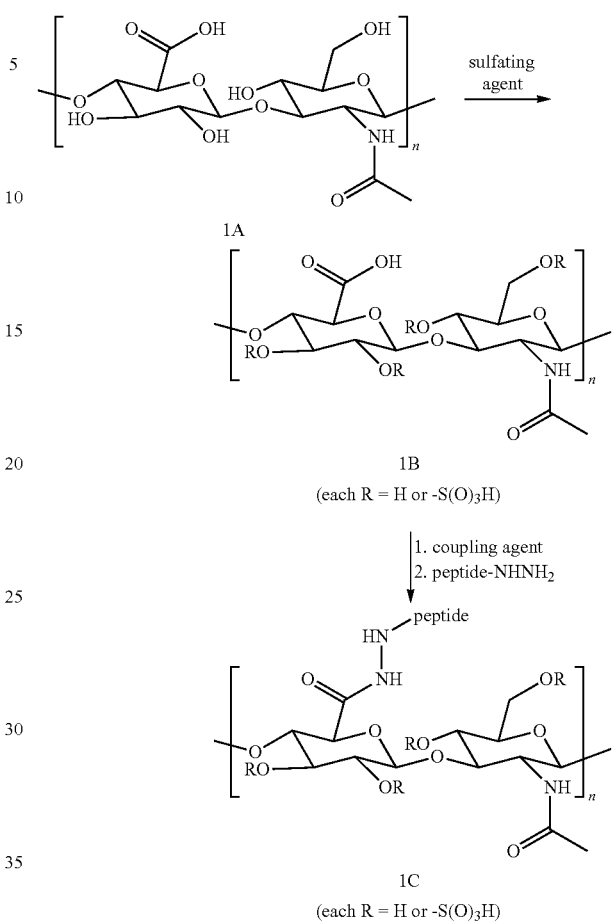

Scheme 1. Synthesis of Bioconjugates

1A 1B
(each R = H or -S(O)₃H)

1. coupling agent
2. peptide-NHNH₂

1C
(each R = H or -S(O)₃H)

In certain embodiments, the peptide sequence can comprise a reactive moiety (e.g., a hydrazide functional group) to aid in the coupling reaction with the glycan, or O-acylisourea intermediate thereof. In some embodiments, the peptide sequence includes one or more amino acid residues that act as a spacer between the binding unit and the terminal amino acid (e.g., a terminating glycine) or reactive moiety (i.e., hydrazide functional group). In addition, in certain instances where one or more amino acids in the peptides contain reactive functional groups (e.g., carboxylic acid side chains), standard protecting group chemistry may be used to protect one or more side chains facilitate the coupling reaction. In addition, non-amino acid spacers may also be employed alone, or in combination with amino acid spacers (e.g., aminohexanoic acid). In certain embodiments, the chemically sulfated glycan derivative 1B is prepared from an O-carboxymethylated glycan derivative(s) (i.e., wherein at least one R is —CH₂C(O)OH), which can then be further reacted with peptide, optionally in the presence of a coupling agent, to provide alternative bioconjugates. In certain embodiments, the chemically sulfated glycan derivative 1B derivatives having at least one free hydroxyl group can be converted to an O-carboxymethylated glycan derivative(s), which can then be further reacted with peptide, optionally in the presence of a coupling agent, to provide alternative bioconjugates.

In some embodiments, the reaction is carried out in the presence of reactive nucleophile, such as N-hydroxysuccinimide (NHS), and/or hydroxybenzotriazole (HOBT) N-hydroxysuccinimide (NHS), hydroxybenzotriazole (HOBt), 1-hydroxy-1,2,3-benzotriazole, HOBt/CuCl$_2$, 7-aza-1-hydroxy-1,2,3-benzotriazole (HOAt), 3,4-dihydro-3-hydroxy-4-oxo-1,2,3-benzotriazole (HOOBt), and/or 3-sulfo-1-hydroxysuccinimide (S-NHS), or derivatives thereof.

4. Methods of Use a. Treatment of Fibrosis

In one embodiment, provided herein are bioconjugates and methods for preventing and/or treating fibrosis. Fibrosis is an inflammatory disease in which inflammatory cells migrate into tissue and organs, leading to cellular responses that result in scarring. Fibrosis can occur in many tissues within the body, typically as a result of inflammation or damage. By preventing inflammatory cell extravasation, fibrosis can be attenuated or prevented.

In one embodiment, the bioconjugates and methods provided herein can be used to prevent and/or treat pulmonary fibrosis. In lungs, types of fibrosis include pulmonary fibrosis such as cystic fibrosis and idiopathic pulmonary fibrosis. Pulmonary fibrosis is a respiratory disease in which scars are formed in the lung tissues, leading to serious breathing problems. Scar formation leads to thickening of the walls, and causes reduced oxygen supply in the blood. As a consequence patients suffer from perpetual shortness of breath.

In one embodiment, the bioconjugates and methods provided herein can be used to treat liver fibrosis. Liver fibrosis may result from a wide variety of conditions including chronic alcohol exposure, hepatitis B virus (HBV) infection, non-alcoholic fatty liver disease (NAFLD), Nonalcoholic steatohepatitis (NASH), hepatitis C virus (HCV) infection, Wilson's disease, alpha-1-antitrypsin deficiency, hemochromatosis, primary biliary cirrhosis, primary sclerosing cholangitis, and autoimmune hepatitis. Chronic HCV is the leading contributor to chronic liver disease and the liver elicits a persistent inflammatory and fibrosis, which is characterized by the formation of fibrous tissue and scarring on the liver. NAFLD and NASH also cause inflammation and fibrosis in the liver.

Cirrhosis is fibrosis in the liver in which the liver does not function properly due to long-term damage. Typically, the disease comes on slowly over months or years. Early on, there are often no symptoms. As the disease worsens, a person may become tired, weak, itchy, have swelling in the lower legs, develop yellow skin, bruise easily, have fluid buildup in the abdomen, or develop spider-like blood vessels on the skin. The fluid build-up in the abdomen may become spontaneously infected. Other complications include hepatic encephalopathy, bleeding from dilated veins in the esophagus or dilated stomach veins, and liver cancer. Hepatic encephalopathy results in confusion and possibly unconsciousness. Cirrhosis can result in liver dysfunction. The following symptoms or features are direct consequences of liver dysfunction and thus can also be treated or ameliorated by the presently disclosed compositions and methods.

It has been shown that that direct interaction between hepatic stellate cells (HSCs) and tumor cells promotes tumor growth via multiple mechanisms. Therefore, targeting HSCs to lessen or eliminate their tumor-supporting role presents a potential therapeutic strategy to prevent, inhibit or treat hepatocellular carcinoma (HCC). In certain embodiments, provided is a method of preventing or inhibiting the development of hepatocellular carcinoma (HCC) in a patient in need thereof, comprising administering to the patient an effective amount of a bioconjugate as described herein. In certain embodiments, the development of hepatocellular carcinoma (HCC) is a result of liver cirrhosis. In certain embodiments, the method comprises inhibiting hepatic stellate cell proliferation and/or fibrotic phenotype transition. In certain embodiments, the bioconjugate is administered locally to the liver, such as during a transcatheter arterial chemoembolization (TACE) procedure.

Spider angiomas or spider nevi are vascular lesions consisting of a central arteriole surrounded by many smaller vessels and occur due to an increase in estradiol. Palmar erythema is a reddening of palms at the thenar and hypothenar eminences also as a result of increased estrogen. Gynecomastia, or increase in breast gland size in men that is not cancerous, is caused by increased estradiol and can occur in up to two thirds of patients. Hypogonadism, a decrease in sex hormones manifest as impotence, infertility, loss of sexual drive, and testicular atrophy, can result from primary gonadal injury or suppression of hypothalamic/pituitary function. Hypogonadism is associated with cirrhosis due to alcoholism and hemochromatosis. Liver size can be enlarged, normal, or shrunken in people with cirrhosis.

In one embodiment, the bioconjugates and methods provided herein can be used to prevent and/or treat renal fibrosis. Renal fibrosis can result from acute or sustained injury to the kidney. The injury can lead to excessive deposition of extracellular matrix. Over time, this can result in kidney failure, requiring patients to undergo dialysis or kidney transplant.

Ascites, accumulation of fluid in the peritoneal cavity, gives rise to flank dullness. This can be visible as increase in abdominal girth. Fetor hepaticus is a musty breath odor resulting from increased dimethyl sulfide. Jaundice is yellow discoloration of the skin and mucous membranes due to increased bilirubin. In addition, liver cirrhosis increases resistance to blood flow and higher pressure in the portal venous system, resulting in portal hypertension.

In one embodiment, the bioconjugates and methods provided herein can be used to prevent and/or treat fibrosis in the heart. Fibrosis in the heart is present in the form of atrial fibrosis, endomyocardial fibrosis, or myocardial infarction. Glial scar is fibrosis in the brain. Other types of fibrosis include, without limitation, arthrofibrosis (knee, shoulder, other joints), Crohn's disease (intestine), Dupuytren's contracture (hands, fingers), keloid (skin), mediastinal fibrosis (soft tissue of the mediastinum), myelofibrosis (bone marrow), Peyronie's disease (penis), nephrogenic systemic fibrosis (skin), progressive massive fibrosis (lungs), retroperitoneal fibrosis (soft tissue of the retroperitoneum), scleroderma/systemic sclerosis (skin, lungs), and some forms of adhesive capsulitis (shoulder).

It is contemplated that the compositions and methods of the present disclosure are suitable for preventing and/or treating any of these diseases or symptoms or features associated with these diseases. Development of fibrosis involves stimulated cells laying down connective tissue, including collagen and glycosaminoglycans. The bioconjugates of the present disclosure can interact with the collagen or glycosaminoglycans and thus disrupt the formation of such excessive connective tissue. The bioconjugates can also protect the endothelial barrier. This can be by interacting with exposed extracellular matrix due to microvascular injury. Protecting the endothelial barrier prevents inflammatory cells from extravating into the tissue to cause the excessive ECM deposition that leads to the fibrotic tissue. Accordingly, the bioconjugates can prevent, inhibit, delay, and/or reverse fibrosis.

In certain embodiments, the fibrosis is post ischemic, post infectious, or idiopathic (e.g., renal, hepatic, cardiac, pulmonary). See, e.g., Guerrot, D., et al. Fibrogenesis & tissue repair 5.Suppl 1 (2012): S15, and Yamaguchi, I., et al. Nephron Experimental Nephrology 120.1 (2012): e20-e31. In certain embodiments, the fibrosis is retroperitoneal. In certain embodiments, the fibrosis is dermal (e.g., scleroderma). See, e.g., Maurer, B., et al. Annals of the rheumatic diseases (2013): annrheumdis-2013.

In one embodiment, the disease is not acute tubular necrosis, diabetic chronic renal failure, lupus nephritis, renal fibrosis, or acute glomerulonephritis. In one embodiment, the disease is not idiopathic pulmonary fibrosis (IPF), chronic obstructive pulmonary disease, asthma, or emphysema.

In certain embodiments, the fibrosis is caused by, or otherwise related to, a lysosomal storage disorder, including but not limited to, Fabry disease, Gaucher disease, Niemann-Pick disease, and Hunter syndrome (mucopolysaccharidoses). Therefore, in certain embodiments, provided herein a method for preventing fibrosis caused by, or otherwise related to, a lysosomal storage disorder in a patient in need thereof.

In one embodiment, provided herein is a use of the bioconjugate(s) disclosed herein for the prevention or treatment of fibrosis. In one embodiment, provided herein is a use of the bioconjugate(s) disclosed herein for the preparation of a medicament for the prevention or treatment of fibrosis. In one embodiment, provided herein is a use of the bioconjugate(s) disclosed herein for the prevention or treatment of liver fibrosis. In one embodiment, provided herein is a use of the bioconjugate(s) disclosed herein for the prevention or treatment of pulmonary fibrosis. In one embodiment, the bioconjugate comprises sulfated hyaluronic acid and from about 50 to about 150, or about 100, peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom. In one embodiment, the peptide(s) are bond to the heparin or other glycan via a hydrazide-carbonyl linkage. In one embodiment, the bioconjugate comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17). In one embodiment, the peptide(s) are bound to the heparin via a hydrazide-carbonyl linkage.

In one embodiment, provided herein is a method for preventing or treating liver fibrosis or pulmonary fibrosis in a patient in need thereof, comprising administering to the patient an effective amount of a bioconjugate comprising sulfated hyaluronic acid bonded to about 50 to about 150, or about 100 peptides comprising GQLYKSILYGSGSGSRR (SEQ ID NO: 17) or GQLYKSILY (SEQ ID NO: 16). In one embodiment, provided herein is a use of the bioconjugate(s) disclosed herein for the prevention or treatment of liver fibrosis or pulmonary fibrosis in a patient in need thereof. In one embodiment, an effective amount of a bioconjugate comprising sulfated hyaluronic acid bonded to about 50 to about 150, or about 100 peptides comprising GQLYKSILYGSGSGSRR (SEQ ID NO: 17) is administered.

Also provided herein are methods for preventing and/or treating vasculitis. Vasculitis is defined by inflammation of the blood-vessel wall and forms the pathological foundation of a diverse group of individual disease entities. Vasculitis is one of the intractable pathological conditions commonly observed in autoimmune diseases, and many cases thereof are refractory to conventionally-used therapeutic methods such as steroids and immunosuppressants. In the vasculitis syndrome, inflammation occurs in arteries of various sizes, and fever, pain in muscles and joints, vascular occlusion, skin ulcer, and mononeuritis multiplex may develop. The methods may be used to treat large vessel vasculitis (LVV), medium vessel vasculitis (MVV), small vessel vasculitis (SVV), variable vessel vasculitis (VVV), single-organ vasculitis (SOV), vasculitis associated with systemic disease, and/or vasculitis associated with probable etiology. Non-limiting examples of large vessel vasculitis (LVV) include takayasu arteritis (TAK) and giant cell arteritis (GCA). Non-limiting examples of medium vessel vasculitis (MVV) include polyarteritis nodosa (PAN) and kawasaki disease (KD). Non-limiting examples of small vessel vasculitis (SVV) include antineutrophil cytoplasmic antibody (ANCA)-associated vasculitis (AAV), microscopic polyangiitis (MPA), granulomatosis with polyangiitis (Wegener's) (GPA), eosinophilic granulomatosis with polyangiitis (Churg-Strauss) (EGPA), immune complex SVV, anti-glomerular basement membrane (anti-GBM) disease, gryoglobulinemic vasculitis (CV), IgA vasculitis (Henoch-Schonlein) (IgAV), and hypocomplementemic urticarial vasculitis (HUV)) (anti-C1q vasculitis). Non-limiting examples of variable vessel vasculitis (VVV) include Behcet's disease (BD) and Cogan's syndrome (CS). Non-limiting examples of single-organ vasculitis (SOV) include cutaneous leukocytoclastic angiitis, cutaneous arteritis, primary central nervous system vasculitis, and isolated aortitis. Non-limiting examples of vasculitis associated with systemic disease include lupus vasculitis, rheumatoid vasculitis, and sarcoid vasculitis. Non-limiting examples of vasculitis associated with probable etiology include hepatitis C virus-associated cryoglobulinemic vasculitis, hepatitis B virus-associated vasculitis, syphilis-associated aortitis, drug-associated immune complex vasculitis, drug-associated ANCA-associated vasculitis, and cancer-associated vasculitis. Other examples of vasculitis include antiphospholipid syndrome, Buerger's disease (thromboangiitis obliterans), cryoglobulinemia, cryopyrin-associated autoinflammatory syndrome (CAPS) (juvenile), goodpastures, localized scleroderma (juvenile), polymyalgia rheumatica, Raynaud's phenomenon, scleroderma, Sjogren's syndrome, and systemic lupus erythematosus. It is contemplated that the bioconjugates and methods disclosed herein can be used to inhibiting and/or treating vasculitis.

In one embodiment, provided herein are methods for preventing and/or treating vessel vasculitis. In one embodiment, provided herein are methods for preventing and/or treating small vessel vasculitis, including antineutrophil cytoplasmic antibody (ANCA)-associated vasculitis (AAV), microscopic polyangiitis (MPA), granulomatosis with polyangiitis (Wegener's) (GPA), eosinophilic granulomatosis with polyangiitis (Churg-Strauss) (EGPA), immune complex SVV, anti-glomerular basement membrane (anti-GBM) disease, gryoglobulinemic vasculitis (CV), IgA vasculitis (Henoch-Schonlein) (IgAV), and/or hypocomplementemic urticarial vasculitis (HUV)) (anti-C1q vasculitis). Such diseases affect small vessels (e.g., very small arteries, arterioles, capillaries, and small veins).

Combination Therapy

In some embodiments, the compositions of the present disclosure can be used in combination with a second agent useful for preventing or treating fibrosis. Accordingly, in one embodiment, a combination, composition, package or kit is provided that includes any composition of the present disclosure and one or more such second agent. In one embodiment, any treatment method of the present disclosure further includes administration of one or more such second agent.

The second agent can be any pharmaceutical or biologic agent that is useful for preventing, treating or otherwise ameliorating symptoms of fibrosis. Non-limiting examples include steroids such as predonine, reducing agents such as N-acetylcysteine, antifibrotic drugs such as pirfenidone and nintedanib, immunosuppressive drugs such as corticosteroids, cyclophosphamide, azathioprine, methotrexate, penicillamine, and cyclosporine A and FK506, and other agents like colchicine, IFN-γ and mycophenolate mofetil.

In some embodiments, the compositions of the present disclosure can be used in combination with a second agent useful for preventing or treating vasculitis. Accordingly, in one embodiment, a combination, composition, package or kit is provided that includes any composition of the present disclosure and one or more such second agent. In one embodiment, any treatment method of the present disclosure further includes administration of one or more such second agent.

The second agent can be any pharmaceutical or biologic agent that is useful for preventing, treating or otherwise ameliorating symptoms of vasculitis. Non-limiting examples include prednisone, Cyclophosphamide (Cytoxan), methylprednisolone, methotrexate sodium, Medrol (Pak), Medrol, dexamethasone, prednisolone, DexPak, Deltasone, cortisone, Prednisone Intensol, dexamethasone sodium phosphate, Orapred ODT, Trexall, Rheumatrex, methotrexate sodium (PF), Veripred 20, Dexamethasone Intensol, prednisolone sodium phosphate, Pediapred, Millipred, Rayos, Millipred, and DoubleDex.

b. Coronary Artery Disease (CAD) and Peripheral Artery Disease (PAD)

One embodiment of the present disclosure provides methods and associated compositions for improving the success rate and/or reducing failure of a surgical bypass procedure. Bypass grafts are used as one form of treatment of arterial blockage in both coronary artery disease (CAD) and peripheral artery disease (PAD). Approximately 500,000 coronary artery bypass graft (CABG) procedures and over 70,000 peripheral bypass graft procedures are performed annually in the US. Most commonly, an autologous vessel graft is harvested, often from the saphenous vein.

Despite the prevalence of surgical bypass with autologous vein grafts to restore blood flow, there are a large number of vein graft failures (VGF) in both CAD and PAD. In the periphery alone, vein graft failure rates reach levels of 50% failure within 5 years. While 5% to 10% of vein grafts fail shortly after implantation due to technical factors and acute thrombosis, mid-term failure (3 to 24 months) may occur in another 20% to 30% of cases and can lead to costly surveillance, reintervention procedures and amputation. The 12-month incidence of vein graft failure in CLI patients (n=1219) was 29% during a two-decade experience at the Brigham and Women's Hospital. The consequences of vein graft failure are often severe for the patient, including recurrent ischemic symptoms, debilitating surgery and limb loss. To date, pharmacotherapies and technical innovations have had little impact on reducing vein graft failure.

It is contemplated that injuries to the fragile endothelial layer of vein graft conduits, whether caused by vein graft harvesting, preservation media, excessive manipulation in preparation for bypass, or ischemia and reperfusion injury, result in a platelet mediated inflammatory response within the vessel wall after implantation. Such endothelial injuries and ECM-platelet activation cascade can result in early VGF via acute inflammation and thrombosis, or delayed VGF via neointimal hyperplasia. Limiting the exposure of the vein graft sub-endothelial matrix to circulating platelets after implantation, therefore, can help reduce acute vessel wall inflammation, improve re-epithelialization and limit excessive neointimal hyperplasia that may lead to vessel occlusion and VGF. The bioconjugate as described herein can be used as a vein graft preservation solution for patients with cardiovascular disease undergoing surgical bypass with autologous vein grafts. The bioconjugates, and compositions comprising the same, as described herein can be used to treat and/or prevent coronary artery disease and/or peripheral artery disease in a patient in need thereof.

In accordance with one embodiment of the present disclosure, therefore, provided is a method for preparing a vascular graft (e.g., a vein graft) by contacting the internal wall of a section of a blood vessel with a solution that contains a synthetic bioconjugate of the disclosure. One way of implementing the contact is to soak the section in the solution. Conditions for this contact can vary but can be readily determined, depending on the concentration of the synthetic bioconjugate and the characteristics of the blood vessel, such that there is a suitable amount of the synthetic bioconjugate bound to the internal wall. The vascular graft prepared with such a method is also within the scope of the present disclosure.

Once the graft is prepared, it can be implanted to a patient in need thereof. The surgical bypass procedure can be readily carried out by a medical professional. Once implanted, the synthetic bioconjugate bound to the internal wall of the grant can help reduce acute vessel wall inflammation, improve re-epithelialization of the graft and limit excessive neointimal hyperplasia of the graft, resulting in reduced graft failure.

In one embodiment, when the graft has been treated with a synthetic bioconjugate as described above, during or following the bypass procedure, a solution of the synthetic bioconjugate can be injected into the lumen of the graft such that the synthetic bioconjugate will bind to the internal wall of the graft. In one aspect, the injection is done before blood flow is restored or started through the graft. In another aspect, the injection is done shortly after (e.g., within 10 minutes, within 5 minutes, or within 1 minute) the blood flow is restored or started.

In some embodiments, the method is effective in inhibiting negative remodeling of the blood vessel. Coronary artery disease, also known as ischemic or coronary heart disease, occurs when part of the smooth, elastic lining inside a coronary artery (the arteries that supply blood to the heart muscle) develops atherosclerosis, effectively restricting blood flow to the heart. Peripheral arterial disease, also known as atherosclerosis or hardening of the arteries, is a disorder that occurs in the arteries of the circulatory system. Negative remodeling includes the physiologic or pathologic response of a blood vessel to a stimulus resulting in a reduction of vessel diameter and lumen diameter. Such a stimulus could be provided by, for example, a change in blood flow or an angioplasty procedure. In some embodiments, the injection of the bioconjugates described herein, and compositions comprising the same, leads to an increase of vessel diameter by about any of 10%, 20%, 30%, 40%, 60%, 70%, 80%, 95%, or more, compared to the diameter of a vessel of without the injection. Negative remodeling can be quantified, for example, angiographically as the percent diameter stenosis at the lesion site (or disease site). Another method of determining the degree of remodeling involves measuring in-lesion external elastic lamina area using intravascular ultrasound (IVUS). IVUS is a technique that can image the external elastic lamina as well as the vascular lumen. In some embodiments, the negative remodeling is associated with a vascular interventional procedure, such as angioplasty, stenting, or atherectomy. The bioconjugates, and compositions comprising the same, as described herein can therefore be injected before, during and/or after the vascular interventional procedure. In certain embodiments, provided is a method of treating stenosis, or occlusion within the femoropopliteal artery, in a patient in need thereof, comprising applying a solution to the internal wall of a lumen before, during and/or after a balloon angioplasty, wherein the solution comprises an effective amount of a bioconjugate as described herein or a composition comprising the same.

The present disclosure thus provides a method of inhibiting negative remodeling in a blood vessel (e.g., artery) in an individual in need thereof, comprising injecting into the blood vessel wall or tissue surrounding the blood vessel wall an effective amount of a bioconjugate as described herein or a composition comprising the same. In some embodiments, the bioconjugate or composition is injected at or adjacent to a site of potential or actual negative remodeling (such as no more than about 2, 1, or 0.5 cm away from the site). In some embodiments, the nanoparticle composition is injected remotely from a site of potential or actual negative remodeling (for example at least about any of 1, 2, 3, 4, 5, 6, 7, 8, 9, or 10 cm away from the site). In some embodiments, the injection is via a catheter with a needle. In some embodiments, the site is a coronary artery or a peripheral artery. In some embodiments, the artery is selected from the group consisting of renal artery, cerebral artery, pulmonary artery, and artery in the leg. In some embodiments, the artery is a balloon injured artery. Further examples, include, but are not limited to, abdominal aorta, anterior tibial artery, arch of aorta, arcuate artery, axillary artery, brachial artery, carotid artery, celiac artery, circumflex fibular artery, common hepatic artery, common iliac artery, deep femoral artery, deep palmar arterial arch, dorsal digital artery, dorsal metatarsal artery, external carotid artery, external iliac artery, facial artery, femoral artery, inferior mesenteric artery, internal iliac artery, instestinal artery, lateral inferior genicular artery, lateral superior genicular artery, palmar digital artery, peroneal artery, popliteal artery, posterior tibial artery, profunda femoris artery, pulmonary artery, radial artery, renal artery, splenic artery, subclavian artery, superficial palmar arterial arch, superior mesenteric artery, superior ulnar collateral artery, and/or ulnar artery. In certain embodiments, the artery is part of the coronary vasculature.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

c. Vascular Treatments

The bioconjugates and compositions described herein can be used to treat a blood vessel in a patient prior to, during, and/or after a vascular injury or intervention. The vascular intervention can include, but is not limited to, angioplasty with and without stents, graft vessels, atherectomy and vascular access dysfunction, or other surgical procedure.

In various embodiments described herein, a bioconjugate, or composition thereof, may be administered to a patient in need of treatment to inhibit platelet activation, such as that involved in thrombosis, platelet binding to exposed collagen of the denuded endothelium, inflammation resulting from denuding the endothelium, intimal hyperplasia, or vasospasm.

In various embodiments, the bioconjugate can be administered intravenously or into muscle, for example. Other suitable routes for parenteral administration include intravascular, intravenous, intraarterial, intramuscular, cutaneous, subcutaneous, percutaneous, intradermal, and intraepidermal delivery. Suitable means for parenteral administration include needle (including microneedle) injectors, infusion techniques, and catheter-based delivery. The catheter-based delivery can include delivering the bioconjugate as a coating on a balloon, through a porous balloon, or as a coating on a stent. In another embodiment, the bioconjugate can be delivered systemically (i.e., not delivered directly to the target vessel, but delivered by parenteral administration).

These bioconjugates locally bind to exposed collagen through physical peptide-collagen interactions. When bound to collagen, the bioconjugate has a number of functions including 1) acting as a barrier to platelet attachment/activation, 2) protecting collagen from degradation by inhibiting MMP access, and 3) sequestering growth factors FGF-2, FGF-7, and FGF-10, thus promoting endothelial and epithelial cell proliferation and migration.

The bioconjugates can compete for platelet binding sites on collagen and prevent platelet binding and activation. The glycan backbone of the bioconjugate can be negatively charged and bind water molecules, creating a hydrophilic barrier over the collagen surface that prevents platelet and protein adhesion. By masking the exposed collagen, rather than inhibiting normal platelet function, the bioconjugate can provide a local treatment that addresses the initial steps in the cascade to inflammation and intimal hyperplasia.

In one embodiment, the present disclosure provides a new approach to address the unmet need of vascular access dysfunction in patients receiving hemodialysis. In one embodiment, the approach entails generation of a luminal vessel coating designed from a bioconjugate as described herein. In arteriovenous fistula (AVF), for example, the neointimal hyperplasia mostly occurs in the venous portion of the AVF. While the initial mechanisms of intimal hyperplasia are similar in arteries and veins, there are differences in the resulting lesions. Venous neointimal hyperplasia tends to be a more aggressive lesion than arterial intimal hyperplasia in the setting of peripheral vascular disease and have poorer response to angioplasty. The ability of the disclosed bioconjugate to prevent platelet binding and intimal hyperplasia in an arterial injury is contemplated to contribute to its ability to reduce or prevent neointimal hyperplasia.

Thus, in some embodiments, the present disclosure provides a method for improving maturation of an arteriovenous fistula (AVF) in a patient in need of hemodialysis, or alternatively for improving patency, enlarging inner diameter of the veins, reducing stenosis, reducing neointimal hyperplasia, reducing hemodynamic stress, reducing endothelial or smooth muscle cell injury, reducing vascular access dysfunction, or reducing coagulation or inflammation at the AVF. In some embodiments, the method entails applying a solution to the internal wall of a lumen of an AVF; and restoring or initiating blood flow in the AVF, wherein the solution is a bioconjugate of the present disclosure, or the solution comprises an effective amount of a bioconjugate of the present disclosure.

A localized treatment is disclosed using a synthetic polymeric luminal coating, which binds specifically to exposed collagen, where the coating can block platelet adhesion to the vessel wall and thus inhibit the initiating events in thrombosis and intimal hyperplasia. Additionally, the coating can promote rapid re-endothelialization of the vessel wall, resulting in faster healing. It is contemplated that the application of the disclosed bioconjugate to native AV fistulas during the creation will result in fistulas with significantly less stenosis and larger diameters.

In some embodiments, for a newly created AVF before blood flow is initiated, the solution is applied less than about 10 minutes before the blood flow is initiated. In some embodiments, the solution is applied less than about 20, 15, 10, 9, 8, 7, 6, 5, 4, 3, or 2 minutes, or 60, 45, 30, 20, 10 or 5 seconds before the blood flow is initiated. In some embodiments, the solution is applied at least 1 minute or at least 2, 3, 4, 5 minutes before the blood flow is initiated. In some embodiments, the solution is applied at least 1 minute or at least 2, 3, 4, 5 minutes after blood flow is restored. In some embodiments, blood flow is initiated, then stopped to allow for delivery of the solution. In some embodiments, the solution is applied to the vessel prior to creation of an anastomosis, during the creation of an anastomosis, or after. In some embodiments, the solution is applied to the vessel prior to creation of an anastomosis, during the creation of an anastomosis, and after.

In some embodiments, the solution is flushed through the AVF, e.g., with a needle, catheter or other drug-delivery device. In one embodiment, the method further entails closing the AVF after the AVF is flushed with the solution. In some embodiments, in addition to the application of the solution as described above, or alternatively, the solution is injected into an enclosed lumen generated by clamping the proximal and vein and artery of an established AVF.

In one embodiment, the solution is applied within about 5 minutes (or alternatively within 10, 9, 8, 7, 6, 4, 3, or 2 minutes) following vein dilation or rubbing of the vein portion of the AVF, which is used to enlarge the internal diameter of the vein. Applying the solution to the mechanically dilated or rubbed surface of the vein interior can reduce loss of the bioconjugate on the surface during rubbing.

It is further contemplated that the disclosed compositions and methods can be used for establishing a vascular access in a patient which method can entail applying a solution of the disclosure to a wall of a blood vessel in a vascular access; and restoring or initiating blood flow in the vascular access. In some embodiments, the wall is an internal wall of the blood vessel, but it can also be the external wall of any blood vessel.

In some embodiments, the vascular access is an arteriovenous fistula (AVF), an arteriovenous graft (AVG), or a durable vascular access used for parenteral nutrition, chemotherapy, or plasmapheresis. It is contemplated that the solution reduces exposure of the wall to platelets. In some embodiments, the wall comprises a cell or tissue exposed to blood flow due to injury or a surgical procedure. It is shown that application of the solution improves patency, improves survival, improves blood flow, enlarges vascular inner diameter, or reduces stenosis in the vascular access, such as AVF and AVG.

In one embodiment, the present disclosure provides a method for improving maturation of an arteriovenous fistula (AVF) in a patient in need of hemodialysis, or alternatively for improving patency, enlarging inner diameter of the veins, reducing stenosis, reducing neointimal hyperplasia, reducing hemodynamic stress, reducing endothelial or smooth muscle cell injury, reducing vascular access dysfunction or reducing coagulation or inflammation at the AVF. In some embodiments, the method entails applying a solution to the internal wall of a lumen of an AVF; and restoring or initiating blood flow in the AVF, wherein the solution comprises an effective amount of a bioconjugate of the present disclosure.

It is contemplated that the bioconjugates may be administered to the interior of the patient's vessel percutaneously or intravenously. The percutaneous or intravenous delivery allows for treatment of a patient post-surgical fistula creation. The bioconjugates may be delivered for treatment of the vessel, maintenance of the vessel, or prevention of the failure of the fistula.

In some embodiments, the methods further include carrying out one or more maintenance applications, such as balloon-assisted maturation, balloon angioplasty, atherectomy, or declotting procedures. Still, in some embodiments, prophylactic delivery at the time of hemodialysis, especially following the procedure when especially high flow rates damage the endothelium and an injection in the graft or fistula is contemplated to be beneficial for maintenance and prevention of stenosis.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO 42), CVWLWEQC (SEQ ID NO: 39), or WREPSFCALS (SEQ ID NO: 22), or an amino acid sequence having one, two, or three amino additions, deletions and/or substitutions each therefrom.

d. Vascular Intervention

Vascular intervention, such as percutaneous coronary intervention, can be carried out by any conventional procedure prior to, during, or after administration of the collagen-binding synthetic bioconjugate. Examples of vascular intervention procedures contemplated for use in conjunction with the method of the present invention include stenting, atherectomy, and angioplasty, such as balloon angioplasty. The vascular intervention procedure can be one which involves temporarily occluding the vessel (e.g., balloon angioplasty), or it can be one which does not involve temporarily occluding the vessel (e.g., non-balloon angioplasty procedures, stenting procedures that do not involve balloon angioplasty, etc.). Illustrative modes of delivery can include a catheter, parenteral administration, a coating on a balloon, through a porous balloon, a coated stent, and any combinations thereof or any other known methods of delivery of drugs during a vascular intervention procedure.

In another illustrative embodiment, during a vascular intervention procedure, any of these bioconjugates with conservative amino acid substitutions can inhibit platelet binding to exposed collagen of the denuded endothelium, platelet activation, thrombosis, inflammation resulting from denuding the endothelium, intimal hyperplasia, and/or vasospasm, or can stimulate endothelial cell proliferation or can bind to collagen in a denuded vessel. In another illustrative embodiment, during a vascular intervention procedure, any of the bioconjugates with conservative amino acid substitutions described in this paragraph can inhibit platelet binding to exposed collagen of the denuded endothelium, platelet activation, intimal hyperplasia, and/or vasospasm, or can bind to collagen in a denuded vessel.

In various embodiments described herein, a collagen-binding synthetic bioconjugate may be administered to a patient (e.g., a patient in need of treatment to inhibit platelet activation, such as that involved in thrombosis, platelet binding to exposed collagen of the denuded endothelium, thrombosis, inflammation resulting from denuding the endothelium, intimal hyperplasia, or vasospasm). In various embodiments, the collagen-binding synthetic bioconjugate can be administered intravenously or into muscle, for example. Suitable routes for parenteral administration include intravascular, intravenous, intraarterial, intramuscular, cutaneous, subcutaneous, percutaneous, intradermal, and intraepidermal delivery. Suitable means for parenteral administration include needle (including microneedle) injectors, infusion techniques, and catheter-based delivery. In an illustrative embodiment, pharmaceutical formulations for use with collagen-binding synthetic bioconjugates for parenteral administration or catheter-based delivery comprising: a) a pharmaceutically active amount of the collagen-binding synthetic bioconjugate; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any individual component a), b), c), or d) or any combinations of a), b), c) and d) are provided.

In any of the embodiments described herein, the collagen-binding synthetic bioconjugate can be administered intravascularly into the patient (e.g., into an artery or vein) in any suitable way. In various embodiments described herein, the collagen-binding synthetic bioconjugate can be administered into a vessel of a patient prior to, during, or after vascular intervention. In various embodiments, vascular interventions, such as percutaneous coronary intervention (PCI), can include, for example, stenting, atherectomy, grafting, and angioplasty, such as balloon angioplasty. Illustratively, the vascular intervention can be one which involves temporarily occluding an artery, such as a coronary artery or a vein (e.g., balloon angioplasty), or it can be one which does not involve temporarily occluding an artery or a vein (e.g., non-balloon angioplasty procedures, stenting procedures that do not involve balloon angioplasty, etc.). Illustrative modes of delivery can include a catheter, parenteral administration, a coating on a balloon, through a porous balloon, a coated stent, and any combinations thereof or any other known methods of delivery of drugs during a vascular intervention procedure. In one illustrative embodiment, the target vessel can include a coronary artery, e.g., any blood vessel which supplies blood to the heart tissue of a patient, including native coronary arteries as well as those which have been grafted into the patient, for example, in an earlier coronary artery bypass procedure. In any of the embodiments described herein, the target vessel into which the collagen-binding synthetic bioconjugate is to be administered and on which the vascular intervention procedure is to be performed may contain a blockage, such as a stenosis or some other form of complete or partial blockage which causes reduced blood flow through the vessel. Thus, the collagen-binding synthetic bioconjugate can be delivered to the vessel via a catheter (e.g., a dilatation catheter, an over-the-wire angioplasty balloon catheter, an infusion catheter, a rapid exchange or monorail catheter, or any other catheter device known in the art) which is percutaneously inserted into the patient and which is threaded through the patient's blood vessels to the target vessel. Various catheter-based devices are known in the art, including those described in U.S. Pat. No. 7,300,454, incorporated herein by reference. In various embodiments described herein where a catheter is used, the catheter used to deliver the collagen-binding synthetic bioconjugate can be the same catheter through which the vascular intervention is to be performed, or it can be a different catheter (e.g., a different catheter which is percutaneously inserted into the patient via the same or a different cutaneous incision and/or which is threaded through the patient's blood vessels to the target vessel via the same or a different route). In another embodiment, the collagen-binding synthetic bioconjugate can be injected directly into the target vessel. In another embodiment, the collagen-binding synthetic bioconjugate can be delivered systemically (i.e., not delivered directly to the target vessel, but delivered by parenteral administration without catheter-based delivery).

In the case where the vessel contains a blockage (e.g., a stenosis), administration can be carried out by delivering the collagen-binding synthetic bioconjugate directly to the target vessel at the site of the blockage or distal to the blockage or both. In another embodiment, the collagen-binding synthetic bioconjugate can be delivered to one or more sites proximal to the blockage. Illustratively, the catheter tip can be maintained stationary while the collagen-binding synthetic bioconjugate is being delivered, or the catheter tip can be moved while the collagen-binding synthetic bioconjugate is being delivered (e.g., in a proximal direction from a position that is initially distal to the blockage, to or through the blockage, or to a position which is proximal to the blockage).

As indicated above, in one embodiment, the collagen-binding synthetic bioconjugate can be administered directly into the patient's vessel at a time prior to vascular intervention, e.g., percutaneous coronary intervention. For example, delivery of the collagen-binding synthetic bioconjugate can be carried out just prior to vascular intervention (e.g., within about 1 hour, such as within about 30 minutes, within about 15 minutes, and/or within about 5 minutes prior to vascular intervention). Optionally, delivery of the collagen-binding synthetic bioconjugate directly to the target vessel can be continued during all or part of the vascular intervention procedure and/or subsequent to completion of such procedure, or delivery of the collagen-binding synthetic bioconjugate directly to the target vessel can be stopped prior to the commencement of the vascular intervention procedure and not subsequently recommenced. In any of the embodiments described herein, delivery of the collagen-binding synthetic bioconjugate can be continuous or it can be effected through a single or multiple administrations. Prior to, during, and/or after the collagen-binding synthetic bioconjugate is administered to the target vessel, the same collagen-binding synthetic bioconjugate or one or more different collagen-binding synthetic bioconjugates can be administered.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

e. Endothelial Dysfunction

The present disclosure, in one embodiment, provides compositions and methods for treating a patient suffering from a disease associated with endothelial dysfunction. The compositions, in some embodiments, include a synthetic collagen binding bioconjugate of the present disclosure.

It is discovered herein that collagen binding bioconjugates can reduce the inflammatory impact of endothelial dysfunction or injury, in both acute and chronic diseases. It is contemplated that such bioconjugates inhibit or reduce platelet binding to the dysfunctional endothelium and thus reduce platelet-mediated inflammation. Inflammation can be activated through platelet processes such as platelet-platelet binding, platelet-leukocyte binding, facilitation of leukocyte diapedesis, or simply release from platelets of local and regional cytokines.

Further, it is discovered that collagen binding bioconjugates decrease pro-inflammatory cytokine secretion and the expression of E-selectin and P-selectin in the exposed endothelial cells. Moreover, these bioconjugates can increase endothelial cell proliferation and migration, attenuate IL-6 secretion and the production of vascular injury markers, even in the presence of platelet-derived growth factor (PDGF). It is contemplated that some or all of these effects brought about by the administration of collagen binding bioconjugates contribute to the reduction of inflammatory at dysfunctional endothelium.

Also provided, in some embodiments, is a method for preventing or reducing inflammation at a vascular site suffering from endothelial dysfunction. The method entails administering to the site a pharmaceutical composition that includes a synthetic collagen binding bioconjugate of the present disclosure.

The term "endothelial dysfunction" is also referred to as "endothelial cell (EC) dysfunction," "dysfunctional endothelium," or "dysfunctional endothelial cells." Endothelial dysfunction can be determined with unmasking or exposure of ICAM and VCAM receptors or selectin receptors on the cell surface of an endothelial cell. P-selectin and E-selectin are examples of selectin receptors exposed which are transiently expressed on the cell surface due to damage and inflammation, and chronically expressed in dysfunctional endothelium.

In some embodiments, endothelial dysfunction is characterized with permeated endothelial lining or damaged endothelial cells. In some embodiments, the endothelial dysfunction is characterized by loss of glycocalyx. In some embodiments, the endothelial dysfunction is characterized by a selectin protein expressed on the surface of endothelial cells and exposed to circulation. In some embodiments, the site suffers from inflammation.

In one aspect, the vascular site is not denuded by physical means and is not undergoing to recovering from a vascular intervention procedure. Non-limiting examples of vascular intervention procedures include percutaneous coronary intervention (PCI).

A "dysfunctional endothelial cell" or "endothelial cell (EC) dysfunction" means the unmasking or exposure of ICAM and VCAM receptors, as well as, selectin receptors on the cell surface of an endothelial cell. P-selectin and E-selectin are examples of selectin receptors exposed which are transiently expressed on the cell surface due to damage and inflammation, and chronically expressed in dysfunctional endothelium. An example of a disease state with chronic dysfunctional endothelial cells is diabetes.

Dysfunction of the endothelium plays an important role in the pathogenesis of a broad spectrum of diseases as endothelial cells participate in the maintenance of functional capillaries.

For instance, the endothelium is directly involved in peripheral vascular disease, stroke, heart disease, diabetes, insulin resistance, chronic kidney failure, tumor growth, metastasis, venous thrombosis, and severe viral infectious diseases (Rajendran et al., Int. J. Biol. Sci., 9:1057-1069, 2013).

A "disease associated with endothelial dysfunction," as used herein, refers to a human disease or condition that is at least in part caused by endothelial dysfunction or that induces endothelial dysfunction. Treating a disease associated with endothelial dysfunction, accordingly, refers to the treatment of the disease, recovering the dysfunctional endothelium, or preventing or ameliorating conditions or symptoms arising from dysfunctional endothelium, such as inflammation, intimal hyperplasia, and thrombosis.

The present inventors have demonstrated that collagen binding bioconjugates can be effectively delivered to any organ of a human patient. Therefore, the collagen binding bioconjugates can be used to treat endothelial dysfunction that occurs at any of the organs and associated with any of the following diseases or conditions.

Vascular diseases. Vascular diseases that can be suitably treated with collagen binding bioconjugates include, without limitation, atherosclerotic diseases (peripheral artery disease, coronary artery disease, stroke, carotid artery disease, renal arterial stenosis), venous thrombotic diseases (deep or superficial vein thrombosis), and iatrogenic large vessel injury (angioplasty, angioplasty with stent placement, atherectomy, thrombectomy, dialysis access creation, vein harvesting for bypass, treatment of brain or aortic aneurysms).

Renal diseases. Renal diseases that can be suitably treated with collagen binding bioconjugates include, without limitation, acute tubular necrosis, diabetic chronic renal failure, lupus nephritis, renal fibrosis, and acute glomerulonephritis.

Pulmonary diseases. Pulmonary diseases that can be suitably treated with collagen binding bioconjugates include, without limitation, idiopathic pulmonary fibrosis (IPF), chronic obstructive pulmonary disease, asthma, and emphysema.

Hematological diseases. Hematological diseases that can be suitably treated with collagen binding bioconjugates include, without limitation, thrombotic thrombocytopenic purpura (TTP), disseminated intravascular coagulation (DIC), and hemolytic uremic syndrome (HUS).

Additionally, dermal diseases such as systemic sclerosis, rheumatologic diseases including vasculitic disorders (lupus), rheumatoid arthritis and other inflammatory arthritis (gout), gastrointestinal diseases including inflammatory bowel disease, hepatitis, and hepatic fibrosis, tumor growth, tumor metastasis, infectious diseases including viral and bacterial sepsis, neurologic diseases including multiple sclerosis, dementia, and amyotrophic lateral sclerosis, ophthalmologic diseases including macular degeneration, glaucoma, and uveitis, endocrinological diseases such as diabetes, and complex regional pain syndrome (CRPS) can also be treated with collagen binding bioconjugates of the present disclosure.

It is contemplated that the bioconjugates can be tailored with respect to the peptide identity, the number of peptides attached to the glycan, and the GAG backbone identity for optimized treatment depending on the disease to be treated and location of the affected dysfunctional endothelium. Thus, a number of molecular design parameters can be engineered to optimize the target effect.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

f. Tissue Adhesion

The methods of the invention are useful in a variety of applications related to tissue adhesions, such as cardiac, abdominal or pelvic adhesion. It is contemplated that the methods of the invention would be useful in treating and/or preventing these persistent defects or recurrent injury.

In certain embodiments, the disclosure provides a method of treating and/or preventing abdominal or pelvic adhesion in a patient in need thereof, comprising applying a pharmaceutical composition on an unnaturally exposed tissue of an organ. In one embodiment, the composition comprises a bioconjugate comprising a glycan having from about 1 to about 80 collagen binding peptide(s) bonded to the glycan. "Exposed tissue" can refer to tissue or a surface that is exposed to a new environment that is seen under normal, healthy conditions, or to tissue that is not exposed to cells or tissue of a different organ under normal, healthy conditions, but is exposed due to disease, or injury, or during a medical procedure (i.e., unnaturally exposed tissue").

An adhesion is a band of fibrous scar tissue that abnormally binds tissues and/or organs that are not normally connected. Adhesions develop in response to various types of injury or tissue disturbances, for example, such as surgery, trauma, infection, chemotherapy, radiation, foreign body, or cancer.

Abdominal and pelvic adhesions are a common complication of abdominal surgical procedures. Abdominal adhesions can cause severe clinical problems and/or pain. For example, abdominal adhesion-related clinical problems may include small-intestinal obstruction, secondary female infertility, ectopic gestation, chronic abdominal and pelvic pain, and difficult and hazardous re-operations (Diamond, M. P., Freeman, M. L. Eur. Soc. Human. Repro. Embryo. 2001; 7(6): 567-576). Abdominal adhesions may cause pain by tethering tissues and/or organs not normally connected and causing traction of nerves. If the bowel becomes obstructed then distention will causes pain. Accordingly, abdominal adhesions may cause intestinal disturbances and bowel obstruction or blockage. In extreme cases, abdominal adhesions may form fibrous bands around a segment of an intestine which constricts blood flow and leads to tissue death.

Standard treatment of abdominal and pelvic adhesions that cause the above clinical problems and/or pain is surgical intervention. However, surgical intervention carries the risk of additional abdominal adhesions and further complications. Therefore, alternative treatment and/or prevention options for abdominal adhesions would be beneficial in treating and/or preventing abdominal adhesions in patients in need thereof.

In one aspect, trauma to the abdominal tissue or organs results in fibrous tissue band formation between abdominal tissues and/or organs. It is contemplated that the methods described herein would be useful in treating and/or preventing said abdominal adhesion.

It is contemplated that the synthetic bioconjugates provided herein will provide a protective hydrating layer to minimize pain, protect abdominal tissue and/or organ collagen from degradation, and promote epithelial migration and epithelial proliferation.

In certain embodiments, the disclosure provides a method of treating and/or preventing abdominal adhesion in a patient in need thereof, comprising applying a pharmaceutical composition on exposed tissue of an abdominal organ. In one embodiment, the composition comprises a bioconjugate comprising a glycan having from about 1 to about 80 collagen binding peptide(s) bonded to the glycan.

In certain embodiments, the disclosure provides a method of treating and/or preventing tendon—tendon sheath adhesion in a patient in need thereof, comprising applying a bioconjugate or composition as described herein to an unnaturally exposed tendon and/or tendon sheath.

In certain embodiments, the disclosure provides a method of treating and/or preventing cardiac adhesion in a patient in need thereof, comprising applying a bioconjugate or composition as described herein to an unnaturally exposed cardiac tissue.

In some aspects, the tissue is exposed due to surgery, trauma, infection, chemotherapy, radiation, foreign body, or cancer. In one aspect, the tissue is surgically exposed.

In some aspects, the composition is applied as a spray. In some aspects, the tissue is a peritoneal membrane tissue.

The compositions and methods of the present disclosure are also contemplated to be useful for reducing or preventing orthopedic adhesions, such as during hand or finger surgeries.

In some embodiments, the methods can further include other methods known in the art in reducing or preventing adhesion, such as the use of a mesh surrounding a tissue.

The bioconjugates provided herein can be used to treat and/or prevent abdominal adhesion in a patient in need thereof by administering to the patient a synthetic bioconjugate that targets extracellular matrix components of the abdominal tissues and/or organs. It is contemplated that the synthetic bioconjugates provided herein can be tailored with respect to the peptide identity, the number of peptides attached to the glycosaminoglycan (GAG) backbone, and the GAG backbone identity to promote abdominal tissue vascularization. Thus, a number of molecular design parameters can be engineered to optimize the target effect.

The bioconjugates provided herein can be used as an adjunct in surgery to prevent or reduce tissue adhesion. During surgery, the synthetic bioconjugates can be delivered to the tissues or organs that are potentially adhesiogenic. It is contemplated that such an administration will help in preventing and/or reducing the post-operative adhesions. In one embodiment, this disclosure provides a method for decreasing or preventing post-surgical adhesions, wherein the method comprises delivering the synthetic bioconjugates provided herein to a surgical site. In another embodiment, the bioconjugates provided herein can be useful in abdominal procedures such as laparoscopic abdominal surgery. In a further embodiment, the bioconjugates provided herein can be delivered through a laparoscope to the tissues or organs that are potentially adhesiogenic. It is contemplated that the treatment with the bioconjugate will treat and/or prevent abdominal adhesion by binding to the area of injury, providing a protective hydrating layer to minimize pain, protecting abdominal tissue and/or organ collagen from degradation, and promoting epithelial migration and epithelial proliferation. It is further contemplated that the bioconjugate will persist in the injured area so that multiple treatments per day are not necessary.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

The compositions of the present disclosure can be administered during open surgery or via a Laparoscope or via any instrument that allows for access to the surgical site.

g. Gastro-Esophageal Injury

The present disclosure, in one embodiment, provides a new approach to address the unmet need of treating or preventing a gastro-esophageal injury in a patient. In general, the new approach entails applying a pharmaceutical composition that includes a synthetic collagen-binding bioconjugate of the present disclosure on the injured gastro-esophageal tissue or cell.

Such application of the composition can generate a coating of the synthetic collagen-binding bioconjugate. The synthetic collagen-binding bioconjugate can bind to collagen exposed on the esophageal tissue through physical peptide-collagen interactions. When bound to collagen, the bioconjugate has a number of functions including 1) acting as a barrier to platelet attachment/activation, 2) protecting collagen from degradation by inhibiting MMP access, and 3) sequestering growth factors FGF-2, FGF-7, and FGF-10, thus promoting endothelial and epithelial cell proliferation and migration, leading to tissue repair and recovery.

The collagen-binding bioconjugate, in one embodiment, includes a polysaccharide backbone with covalently attached collagen-binding peptides. The synthetic bioconjugates can compete for platelet binding sites on collagen and prevent platelet binding and activation. The glycan backbone can be negatively charged and bind water molecules, creating a hydrophilic barrier over the collagen surface that prevents platelet and protein adhesion. By masking the exposed collagen, rather than inhibiting normal platelet function, the bioconjugate can provide a local treatment that addresses the initial steps in the cascade to inflammation and intimal hyperplasia.

This new approach is contemplated to be useful for treating gastro-esophageal injuries, including but not limited to those caused by GERD or iatrogenic interventions. It is further contemplated that patients of the following categories can benefit from this approach: A) GERD associated esophageal lesion requiring esophagogastroduodenoscopic (EGD) ablation; B) Esophageal stricture requiring EGD dilation; and C) Peptic Ulcer Disease (PUD) requiring EGD treatment.

The pharmaceutically composition can be topically applied to one or more lesions of the injured gastro-esophageal tissue. Given the limited accessibility of the tissue, it is contemplated that use of a delivery device is beneficial. For instance, the composition can be delivered during an esophagogastroduodenoscopy (EGD) procedure or using an esophagogastroduodenoscope.

Palifermin is a keratinocyte growth factor useful for oral mucositis treatment. The bioconjugate of present disclosure binds to collagen and also binds to endogenous or exogenous growth factors such as Palifermin. Therefore, such a formulation provides targeted delivery of Palifermin. In some embodiments, this disclosure provides a method for delivering Palifermin. In certain embodiments, the method comprises applying a composition comprising bioconjugate and Palifermin to a patient in need thereof. In other embodiments, this disclosure provides a method for treating oral mucositis in a patient wherein the method comprises applying a composition comprising a bioconjugate and Palifermin to the patient in need thereof.

It is contemplated that the bioconjugates provided in the solution can be tailored with respect to the peptide identity, the number of peptides attached to the glycan, and the GAG backbone identity to promote recovery of an injured gastro-esophageal tissue. Thus, a number of molecular design parameters can be engineered to optimize the target effect.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

h. Wound Healing

The methods and compositions described herein can be used to treat any condition where the integrity of tissue is damaged, including chronic wounds and acute wounds, wounds in connective tissue, and wounds in muscle, bone and nerve tissue. A "wound", as used herein includes surgical incisions, burns, acid and alkali burns, cold burn (frostbite), sun burn, ulcers, pressure sores, cuts, abrasions, lacerations, wounds caused by physical trauma, wounds caused by congenital disorders, wounds caused by periodontal disease or following dental surgery, and wounds associated with cancerous tissue or tumors. As described herein, wounds can include either an acute or a chronic wound.

Acute wounds are caused by external damage to intact skin and include surgical wounds, bites, burns, cuts, lacerations, abrasions, etc. Chronic wounds include, for example, those wounds caused by endogenous mechanisms that compromise the integrity of dermal or epithelial tissue, e.g., leg ulcers, foot ulcers, and pressure sores. In any of the embodiments described herein, the compositions for promoting wound healing or decreasing scar formation may be used at any time to treat chronic or acute wounds. For example, acute wounds associated with surgical incisions can be treated prior to surgery, during surgery, or after surgery to promote wound healing and/or decrease scar formation in a patient. In various illustrative aspects, the compositions as herein described can be administered to the patient in one dose or multiple doses, as necessary to promote wound healing and/or to decrease scar formation.

As used herein, "decreasing scar formation" includes an increase in the ultimate tensile strength of the scar and/or a decrease in the visible scar length. As used herein, a decrease in scar formation also includes complete inhibition of scar formation or complete elimination of visible scarring in a patient.

As used herein, "promoting wound healing" means causing a partial or complete healing of a chronic or an acute wound, or reducing any of the symptoms caused by an acute or a chronic wound. Such symptoms include pain, bleeding, tissue necrosis, tissue ulceration, scar formation, and any other symptom known to result from an acute or a chronic wound.

In any of the embodiments described herein, a method of promoting wound healing is provided. The method comprises the step of administering to the patient a collagen-binding synthetic bioconjugate, wherein the collagen-binding synthetic bioconjugate promotes healing of a wound in the patient. In any of the various embodiments described herein, the collagen-binding synthetic bioconjugate can be an aberrant collagen-binding synthetic bioconjugate or a fibrillogenic collagen-binding synthetic bioconjugate with amino acid homology to a portion of the amino acid sequence of a bioconjugate that normally regulates collagen fibrillogenesis.

In any of the embodiments described herein, a method of decreasing scar formation is provided. The method comprises the steps of administering to the patient a collagen-binding synthetic bioconjugate, wherein the collagen-binding synthetic bioconjugate decreases scar formation in the patient. In any of the various embodiments described herein, the collagen-binding synthetic bioconjugate can be an aberrant collagen-binding synthetic bioconjugate or a fibrillogenic collagen-binding synthetic bioconjugate with amino acid homology to a portion of the amino acid sequence of a bioconjugate that normally regulates collagen fibrillogenesis.

In any of the embodiments described herein, the compositions for promoting wound healing and/or decreasing scar formation can be impregnated into any materials suitable for delivery of the composition to the wound, including cotton, paper, non-woven fabrics, woven fabrics, and knitted fabrics, monofilaments, films, gels, sponges, etc. For example, surgical sutures (monofilaments, twisted yarns or knitting yarns), absorbent pads, transdermal patches, bandages, burn dressings and packings in the form of cotton, paper, non-woven fabrics, woven fabrics, knitted fabrics, films and sponges can be used.

In one embodiment, the bioconjugate used in the methods described above comprises sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom.

i. Corneal Wounds

The methods of the invention are useful in a variety of applications related to corneal wound healing. In one embodiment, the corneal wound condition in need of treatment is a result of traumatic injury to the cornea (Chiapella, A. P., Rosenthal, A. R. British Journal of Ophthalmology, 1985; 69: 865-870). In another embodiment, the wound condition in need of treatment is caused by an ophthalmologic procedure such as Epi-Lasik induce corneal injury (Tuft, S. J., et al. Br J Ophthalmol. 1993; 77: 243-247). In some cases persistent defects or recurrent injury can occur due to lack of or incomplete healing (Kenyon, K. R. Cornea and Refractive Atlas of Clinical Wisdom. Eds. S. A. Melki and M. A. Fava. SLACK, Inc.: New Jersey, US, 2011; pp. 39). It is contemplated that the methods of the invention would be useful in treating these persistent defects or recurrent injury.

In one aspect, injury to the corneal epithelium results in a breach in the corneal barrier function and it is contemplated that the methods described herein would be useful in treating said injury.

The bioconjugates provided herein can be used to promote corneal wound healing in a patient in need thereof by administering to the patient a bioconjugate that targets specific extracellular matrix components implicated in corneal wound healing. It is contemplated that the bioconjugates provided herein can be tailored with respect to the peptide identity, the number of peptides attached to the glycan, and the glycan identity to promote corneal wound healing. Thus, a number of molecular design parameters can be engineered to optimize the target effect.

It is contemplated that the treatment with a bioconjugate comprising sulfated hyaluronic acid and from about 15 to about 30% functionalization with peptides, wherein the peptides comprise at least one sequence of RRANAALKAGELYKSILY (SEQ ID NO: 1), RRANAALKAGELYKSILYGSG (SEQ ID NO: 69), GQLYKSILY (SEQ ID NO: 16), or GQLYKSILYGSGSGSRR (SEQ ID NO: 17), CPGRVMHGLHLGDDEGPC (SEQ ID NO: 42), CVWLWEQC (SEQ ID NO: 39), or WREPSFCALS (SEQ ID NO: 22), or an amino acid sequence having one, two, or three amino additions, deletions and/or substitutions each therefrom, will enhance corneal would healing by binding to the area of injury, providing a protective hydrating layer to minimize pain, protecting corneal collagen from degradation, and/or promoting epithelial migration and/or epithelial proliferation. It is further contemplated that the bioconjugate will persist in the injured area so that multiple treatments per day are not necessary.

5. Compositions

In one embodiment, the bioconjugate is administered in a composition. The present disclosure provides compositions comprising a bioconjugate and a pharmaceutically acceptable carrier. Pharmaceutically acceptable carriers are known to one having ordinary skill in the art may be used, including water or saline. As is known in the art, the components as well as their relative amounts are determined by the intended use and method of delivery. Diluent or carriers employed in the compositions can be selected so that they do not diminish the desired effects of the bioconjugate. Examples of suitable compositions include aqueous solutions, for example, a solution in isotonic saline, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, the composition is an aqueous solution. Aqueous solutions are suitable for use in composition formulations based on ease of formulation, as well as an ability to easily administer such compositions by means of instilling the solution in. In certain embodiments, the compositions are suspensions, viscous or semi-viscous gels, or other types of solid or semi-solid compositions. In some embodiments, the composition is in the form of foams, ointments, liquid wash, gels, sprays and liposomes, which are very well known in the art. Alternatively, the topical administration is an infusion of the provided bioconjugate to the treatment site via a device selected from a pump-catheter system, a continuous or selective release device, or an adhesion barrier. In certain embodiments, the composition is a solution that is directly applied to or contacts the internal wall of a vein or artery. In some embodiments, the composition comprises a polymer matrix. In other embodiments, the composition is absorbable. In certain embodiments, the composition comprises a pH buffering agent. In some embodiments, the composition contains a lubricity enhancing agent.

In certain embodiments, a polymer matrix or polymeric material is employed as a pharmaceutically acceptable carrier or support for the composition. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In certain embodiments, the compositions provided herein is formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the bioconjugate may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

In certain embodiments, the composition contains a lubricity enhancing agent. As used herein, lubricity enhancing agents refer to one or more pharmaceutically acceptable polymeric materials capable of modifying the viscosity of the pharmaceutically acceptable carrier. Suitable polymeric materials include, but are not limited to: ionic and non-ionic water soluble polymers; hyaluronic acid and its salts, chondroitin sulfate and its salts, dextrans, gelatin, chitosans, gellans, other bioconjugates or polysaccharides, or any combination thereof; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); gums such as tragacanth and xanthan gum; gellan gums; alginate and sodium alginate; chitosans; vinyl polymers; hydrophilic polymers such as polyethylene oxides, polyoxyethylene-polyoxypropylene copolymers, and polyvinylalcohol; carboxyvinyl polymers or crosslinked acrylic acid polymers such as the "carbomer" family of polymers, e.g., carboxypolyalkylenes that may be obtained commercially under the Carbopol™ trademark; and various other viscous or viscoelastomeric substances. In one embodiment, a lubricity enhancing agent is selected from the group consisting of hyaluronic acid, dermatan, chondroitin, heparin, heparan, keratin, dextran, chitosan, alginate, agarose, gelatin, hydroxypropyl cellulose, hydroxyethyl cellulose, hydroxypropyl methylcellulose, hydroxypropyl methylcellulose phthalate, methyl cellulose, carboxymethyl cellulose, and etherified cellulose, polyvinyl alcohol, polyvinylpyrrolidinone, povidone, carbomer 941, carbomer 940, carbomer 971P, carbomer 974P, or a pharmaceutically acceptable salt thereof. In one embodiment, a lubricity enhancing agent is applied concurrently with the bioconjugate. Alternatively, in one embodiment, a lubricity enhancing agent is applied sequentially to the bioconjugate. In one embodiment, the lubricity enhancing agent is chondroitin sulfate. In one embodiment, the lubricity enhancing agent is hyaluronic acid. The lubricity enhancing agent can change the viscosity of the composition.

In some embodiments, the bioconjugates can be combined with minerals, amino acids, sugars, peptides, proteins, vitamins (such as ascorbic acid), or laminin, collagen, fibronectin, hyaluronic acid, fibrin, elastin, or aggrecan, or growth factors such as epidermal growth factor, platelet-derived growth factor, transforming growth factor beta, or fibroblast growth factor, and glucocorticoids such as dexamethasone or viscoelastic altering agents, such as ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic.

Suitable pH buffering agents for use in the compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 4 to about pH 8. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7. In some embodiments, the composition is in the form of a film, gel, patch, or liquid solution which comprises a polymeric matrix, pH buffering agent, a lubricity enhancing agent and a bioconjugate wherein the composition optionally contains a preservative; and wherein the pH of said composition is within the range of about pH 4 to about pH 8.

Surfactants are employed in the composition to deliver higher concentrations of bioconjugate. The surfactants function to solubilize the inhibitor and stabilize colloid dispersion, such as micellar solution, microemulsion, emulsion and suspension. Suitable surfactants comprise c polysorbate, poloxamer, polyoxyl 40 stearate, polyoxyl castor oil, tyloxapol, triton, and sorbitan monolaurate. In one embodiment, the surfactants have hydrophile/lipophile balance (HLB) in the range of 12.4 to 13.2 and are acceptable for ophthalmic use, such as TritonX114 and tyloxapol.

In certain embodiments, stabilizing polymers, i.e., demulcents, are added to the composition. The stabilizing polymer should be an ionic/charged example, more specifically a polymer that carries negative charge on its surface that can exhibit a zeta-potential of (−)10-50 mV for physical stability and capable of making a dispersion in water (i.e. water soluble). In one embodiment, the stabilizing polymer comprises a polyelectrolyte or polyelectrolytes if more than one, from the family of cross-linked polyacrylates, such as carbomers and Pemulen®, specifically Carbomer 9'74p (polyacrylic acid), at a range of about 0.1% to about 0.5% w/w.

In one embodiment, the composition comprises an agent which increases the permeability of the bioconjugate to the extracellular matrix of blood vessels. Preferably the agent which increases the permeability is selected from benzalkonium chloride, saponins, fatty acids, polyoxyethylene fatty ethers, alkyl esters of fatty acids, pyrrolidones, polyvinylpyrrolidone, pyruvic acids, pyroglutamic acids or mixtures thereof.

The bioconjugate may be sterilized to remove unwanted contaminants including, but not limited to, endotoxins and infectious agents. Sterilization techniques which do not adversely affect the structure and biotropic properties of the bioconjugate can be used. In certain embodiments, the bioconjugate can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the bioconjugate can be subjected to one or more sterilization processes. Alternatively, the bioconjugate may be wrapped in any type of container including a plastic wrap or a foil wrap, and may be further sterilized.

In some embodiments, preservatives are added to the composition to prevent microbial contamination during use. Suitable preservatives added to the compositions comprise benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures. In certain embodiments, the preservative is selected from benzalkonium chloride, chlorobutanol, benzododecinium bromide, methyl paraben, propyl paraben, phenylethyl alcohol, edentate disodium, sorbic acid, or polyquarternium-1. In certain embodiments, the compositions comprise a preservative. In some embodiments, the preservatives are employed at a level of from about 0.001% to about 1.0% w/v. In certain embodiments, the compositions do not contain a preservative and are referred to as "unpreserved". In some embodiments, the unit dose compositions are sterile, but unpreserved.

In some embodiments, separate or sequential administration of the bioconjugate and other agent is necessary to facilitate delivery of the composition. In certain embodiments, the bioconjugate and the other agent can be administered at different dosing frequencies or intervals. For example, the bioconjugate can be administered daily, while the other agent can be administered less frequently. Additionally, as will be apparent to those skilled in the art, the bioconjugate and the other agent can be administered using the same route of administration or different routes of administration.

Any effective regimen for administering the bioconjugate can be used. For example, the bioconjugate can be administered as a single dose, or as a multiple-dose daily regimen. Further, a staggered regimen, for example, one to five days per week can be used as an alternative to daily treatment.

In various embodiments, the bioconjugate can be administered topically, such as by film, gel, patch, or liquid solution. In some of the embodiments, the compositions provided are in a buffered, sterile aqueous solution. In certain embodiments, the solutions have a viscosity of from about 1 to about 100 centipoises (cps), or from about 1 to about 200 cps, or from about 1 to about 300 cps, or from about 1 to about 400 cps. In some embodiments, the solutions have a viscosity of from about 1 to about 100 cps. In certain embodiments, the solutions have a viscosity of from about 1 to about 200 cps. In certain embodiments, the solutions have a viscosity of from about 1 to about 300 cps. In certain embodiments, the solutions have a viscosity of from about 1 to about 400 cps. In certain embodiments, the solution is in the form of an injectable liquid solution. In other embodiments, the compositions are formulated as viscous liquids, i.e., viscosities from several hundred to several thousand cps, gels or ointments. In these embodiments, the bioconjugate is dispersed or dissolved in an appropriate pharmaceutically acceptable carrier.

Exemplary compositions for use with the bioconjugates for catheter-based delivery may comprise: a) a synthetic bioconjugate as described herein; b) a pharmaceutically acceptable carrier; c) a polymer matrix; d) a pH buffering agent to provide a pH in the range of about pH 4 to about pH 8; and e) a water soluble lubricity enhancing agent in the concentration range of about 0.25% to about 10% total formula weight or any individual component a), b), c), d) or e), or any combinations of a), b), c), d) or e).

Exemplary formulations may comprise: a) bioconjugate as described herein; b) pharmaceutically acceptable carrier; c) polymer matrix; and d) pH buffering agent to provide a pH in the range of about pH 4 to about pH 8, wherein said solution has a viscosity of from about 3 to about 30 cps for a liquid solution.

Exemplary compositions contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include bioconjugates described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, patches, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin films, gels, patches, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

Films used for drug delivery are well known in the art and comprise non-toxic, non-irritant polymers devoid of leachable impurities, such as polysaccharides (e.g., cellulose, maltodextrin, etc.). In some embodiments, the polymers are hydrophilic. In other embodiments, the polymers are hydrophobic. The film adheres to tissues to which it is applied, and is slowly absorbed into the body over a period of about a week. Polymers used in the thin-film dosage forms described herein are absorbable and exhibit sufficient peel, shear and tensile strengths as is well known in the art. In some embodiments, the film is injectable. In certain embodiments, the film is administered to the patient prior to, during or after surgical intervention.

Gels are used herein refer to a solid, jelly-like material that can have properties ranging from soft and weak to hard and tough. As is well known in the art, a gel is a non-fluid colloidal network or polymer network that is expanded throughout its whole volume by a fluid. A hydrogel is a type of gel which comprises a network of polymer chains that are hydrophilic, sometimes found as a colloidal gel in which water is the dispersion medium. Hydrogels are highly absorbent and can contain a high degree of water, such as, for example greater than 90% water. In some embodiments, the gel described herein comprises a natural or synthetic polymeric network. In some embodiments, the gel comprises a hydrophilic polymer matrix. In other embodiments, the gel comprises a hydrophobic polymer matrix. In some embodiments, the gel possesses a degree of flexibility very similar to natural tissue. In certain embodiments, the gel is biocompatible and absorbable. In certain embodiments, the gel is administered to the patient prior to, during or after surgical intervention.

Liquid solution as used herein refers to solutions, suspensions, emulsions, drops, ointments, liquid wash, sprays, liposomes which are well known in the art. In some embodiments, the liquid solution contains an aqueous pH buffer agent which resists changes in pH when small quantities of acid or base are added. In certain embodiments, the liquid solution is administered to the patient prior to, during or after surgical intervention.

Exemplary formulations may comprise: a) one or more bioconjugate as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the bioconjugate is dispersed or dissolved in an appropriate pharmaceutically acceptable carrier.

In certain embodiments, the bioconjugate, or a composition comprising the same, is lyophilized prior to, during, or after, formulation. Accordingly, also provided herein is a lyophilized composition comprising a bioconjugate or composition comprising the same as described herein.

6. Dosing

Suitable dosages of the bioconjugate can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.01 µg to about 10 g. For example, for systemic delivery, the dose can be about 10 g, or about 5 g, or about 1 g. In other illustrative embodiments, effective doses ranges from about 100 µg to about 10 g per dose, or from about 100 µg to about 1 g per dose, or from about 100 µg to about 500 mg per dose, from about 0.01 µg to about 100 mg per dose, or from about 100 µg to about 50 mg per dose, or from about 500 µg to about 10 mg per dose, or from about 1 mg to 10 mg per dose, or from about 1 to about 100 mg per dose, or from about 1 mg to 500 mg per dose, or from about 1 mg to 200 mg per dose, or from about 10 mg to 100 mg per dose, or from about 10 mg to 75 mg per dose, or from about 10 mg to 50 mg per dose, or about 10 mg per dose, or about 20 mg per dose, or about 30 mg per dose, or about 40 mg per dose, or about 50 mg per dose, or about 60 mg per dose, or about 70 mg per dose, or about 80 mg per dose, or about 90 mg per dose, or about 100 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to about 10 mg per dose.

In some embodiments, the compositions are packaged in multidose form. Preservatives are thus required to prevent microbial contamination during use. In certain embodiments, suitable preservatives as described above can be added to the compositions. In some embodiments, the composition contains a preservative. In certain embodiments the preservatives are employed at a level of from about 0.001% to about 1.0% w/v. In some embodiments, the unit dose compositions are sterile, but unpreserved.

EXAMPLES

Example 1: Preparation and Characterization of Sulfated Hyaluronic Acid (sHA)

As the sodium salt of hyaluronic acid (HA) is not soluble in organic solvents, it is necessary to prepare the tetrabutylammonium salt of HA before sulfating it. 3.74 g (9.31 mmol) of HA (sodium salt) was dissolved in 400 mL of distilled water. Dowex-50WX8 beads (75.74 g) were washed three times with 1.4 L of distilled water. The acidic Dowex beads were then added to the HA solution and stirred for 30 minutes at room temperature. The solution was filtered to remove the resin and was treated with tetrabutylammonium hydroxide (1 M in $H_2O$) until pH=6.5. The tetrabutylammonium HA salt (HA-TBA) was lyophilized and obtained as a white solid (5.76 g, 99% yield).

Preparation of Sulfated HA:1 In a dry three neck flask under nitrogen, HA-TBA (5.7622 g, 9.28 mmol, 323 kDa HA) was dissolved in anhydrous DMF (1050 mL) and left to dissolve overnight. In another dry three neck flask under nitrogen, $SO_3$-Pyridine complex (38.890 g, 244.3 mmol, 1:26.3 ratio HA-TBA:$SO_3$) was dissolved in anhydrous DMF (432 mL) and added into the HA-TBA solution. The reaction was stirred for 20 min at room temperature. After 20 min, cold water (500 mL) was quickly added and the reaction mixture transferred to beakers. A precipitate was observed after addition of cold ethanol saturated with sodium acetate (2 L). After filtering, the precipitate was dissolved in water (1 L) before purification by TFF with 5 CV of 0.5 M NaCl followed by 8 CV of water. The product was then lyophilized for 3 days and a beige solid was recovered (3.21 g, 58% yield).

Characterization of sHA: Degree of sulfation was obtained by elemental analysis of nitrogen and sulfur content. Once obtained the following calculation was carried out to determine degree of sulfation (DS):

$$DS = \frac{\% \text{ Sulfur}/32.065}{\% \text{ Nitrogen}/14.0067}$$

Samples were also analyzed by $^1H$ NMR analysis in $D_2O$ to determine any trace impurity from the tetrabutylammonium and/or pyridinium complex with their distinctive peaks.

The degree of sulfation is calculated based on molar ratio of HA:$SO_3$-Pyridine as well as the molecular weight of the initial HA, and is presented as the number of sulfates per disaccharide unit. The following table depicts these differences.

| Initial MW HA | Ratio HA:$SO_3$-Pyridine | Degree of Sulfation |
|---|---|---|
| 20 kDa | 1:13.2 | 1.5 |
|  | 1:19.8 | 1.9 |
| 136 kDa | 1:13.2 | 1.5 |
| 323 kDa | 1:13.2 | 1.5 |
|  | 1:26.3 | 2.4 |
| 738 kDa | 1:13.2 | 1.3 |
|  | 1:26.3 | 1.7 |

[1]Biomacromolecules, 2009, 10, 3290-3297

Example 2: Compound Synthesis

Reaction buffer preparation: 0.064 M MES (2-(N-morpholino)ethanesulfonic acid) with 8.0 M urea, 0.6% NaCl, pH 5.5, prepared within 6 hours prior to reaction. Note that 8 M urea requires solute volume change calculation as follows. Reaction buffer is formulated by the following equations:

$$V_{0.1\ M\ MES,\ 0.9\%\ NaCl}\ (mL) = V_{final}\ (mL) \times 0.64$$

$$\text{Urea (g)} = V_{0.1\ M\ MES,\ 0.9\%\ NaCl}\ (mL) \times 0.7443$$

Where $V_{final}$=target final volume after urea is added

The reaction buffer is then filtered through a 0.2 µm filter. Verify that pH is within pH4.75, adjust with 1M HCl or 0.5M NaOH if required.

TFF buffer preparation: The TFF buffer 10 mM Sodium Phosphate with 8.0 M urea, 0.6% NaCl, pH 7.0-7.8, prepared within 12 hours prior to purification. Note that 8 M urea requires solute volume change calculation as follows. Reaction buffer is formulated by the following equations:

$$V_{15.6\ mM\ sodium\ phosphate}\ (mL) = V_{final}\ (mL) \times 0.64$$

$$V_{100\ mM\ sodium\ phosphate\ dibasic}\ (mL) = V_{final}\ (mL) \times 0.06$$

$$V_{100\ mM\ sodium\ phosphate\ monobasic}\ (mL) = V_{final}\ (mL) \times 0.04$$

$$V_{water}\ (mL) = V_{15.6\ mM\ sodium\ phosphate}\ (mL) - (V_{100\ mM\ sodium\ phosphate\ dibasic}\ (mL) + V_{100\ mM\ sodium\ phosphate\ monobasic}\ (mL))$$

$$\text{Urea (g)} = V_{15.6\ mM\ sodium\ phosphate}\ (mL) \times 0.7443$$

Where $V_{final}$=target final volume after urea is added. The reaction buffer is then filtered through a 0.2 µm filter. Verify that pH is within pH7-7.8, adjust with 1M HCl or 0.5M NaOH if required.

Reaction calculation: The reaction mole ratios are as follows: 2 moles of EDC per GAG disaccharide, 0.12 moles of peptide per GAG disaccharide, and 1 mole of biotin and/or fluorescent tag CF633 per 20 kDa of GAG. The reaction ratio is represented as GAG:Peptide:EDC For instance a reaction of 300 kDA 2.5 degree of sulfation sHA would yield a reaction mole ratio of 1:55:916.

Reaction: Conjugate synthesis involves grafting a hydrazide functionalized peptide onto the GAG backbone through EDC chemistry through the activation of the carboxylic group (GAG activation) on the backbone allowing the activated carboxylic group to react with the hydrazide end at the N Terminus of the peptide.

sHA is dissolved in the reaction buffer at 20 mg/ml, hydrazide functionalized peptide at 3 mg/ml, detection tag (biotin and/or CF633) each at 3 mg/ml and EDC at 75 mg/ml. The GAG can be dissolved 4 hours prior to reaction. Peptide is mixed with GAG and tag before addition of solubilized EDC.

EDC must be dissolved immediately before adding it to the reaction mixture containing solubilized GAG, peptide and tag. The reactions allowed to proceed at 25° C. for 2 hours while the reaction mixture is stirred or shaken. The reaction is then quenched by raising the pH to 8 using 0.5 M NaOH and shaken/stirred for 30 mins.

TFF purification: TFF purification done using Spectrum KR2i TFF system, purchased from Spectrum labs. Modified Polyethersulfone (mPES) filters cartridges with a 30 kD molecular weight cutoff used, purchased from Spectrum labs. Filter surface area will vary depending on batch size. TFF buffer is circulated in TFF system for 10 min to equilibrate the system and then the TFF lines are replaced with fresh buffer. Synthesis reaction vessel is then connected to the TFF system and TFF is performed using 100 mL/min and TMP adjusted to 18 psi. The reaction is diafiltered with 6 purification volumes (CV) of TFF buffer followed by 16 CVs of water (where CV is equal to reaction volume plus TFF holdup volume).

The following bioconjugates were prepared via the procedure outlined above, using various molecular weight sulfated HA backbones and the hydrazide functionalized peptides shown in the table (Table 2).

TABLE 2

| Compound | Backbone | Peptide |
|---|---|---|
| Compound 1 (about 8% peptide functionalization) | sHA, MW = 163 | GQLYKSILYGSGSGSRRNHNH$_2$ (SEQ ID NO: 17) |
| Compound 1B (about 8% peptide functionalization) | sHA, MW = 163 | biotinGQLYKSILYGSGSGSRRNHNH$_2$ (SEQ ID NO: 17) |
| Compound 2 (about 8% peptide functionalization) | sHA, MW = 323 | GQLYKSILYGSGSGSRRNHNH$_2$ (SEQ ID NO: 17) |
| Compound 2B (about 8% peptide functionalization) | sHA, MW = 323 | biotinGQLYKSILYGSGSGSRRNHNH$_2$ (SEQ ID NO: 17) |
| Compound 3 (about 8% peptide functionalization) | sHA, MW = 28 | GQLYKSILYGSGSGSRRNHNH$_2$ (SEQ ID NO: 17) |

Compound 1 and Compound 1B were synthesized by reacting peptide at a ratio of about 30 peptides per glycan. Using this ratio, it is contemplated that the average number of peptides conjugated to glycan is about 20-25 peptides per glycan, corresponding to about 8, or about 8-12% modification. For the various molecular weight sHA conjugates shown in Table 2, the degree of peptide conjugation scaled linearly such that the ratio of peptide to backbone length was constant. Specifically, it is contemplated that the average number of peptides conjugated to glycan for Compound 2 and Compound 2B is about 70-80 peptides per glycan, and the average number of peptides conjugated to glycan for Compound 3 is about 6 peptides per glycan, all corresponding to about 8, or about 8-12% modification.

Example 3: Hepatic Stellate Cell (HSC) In Vitro Assay

Cell proliferation assay. Normal human hepatic primary hepatic stellate cells (HSCs) isolated from single donor human liver was purchased from ScienCell Research Laboratories (San Diego, CA). Early passage HSC (P2) were grown at 6000 cells/well seeding density on fibrillar collagen coated plates in Stellate Cell Medium (SteCM; ScienCell Research Laboratories) supplemented with 0.5% fetal bovine serum (Invitrogen), 1% of stellate cell growth supplement (ScienCell Research Laboratories), 100 U/ml penicillin (Invitrogen, Carlsbad, CA), and 100 U/ml streptomycin (Invitrogen). The primary HSCs were activated in culture by overnight treatment with 10 ng/mL of TGF-β1 (Bio-Techne Corporation, Minneapolis, MN). The cells were then exposed to low serum medium containing biotin-labeled Compounds 1B or 2B at a concentration range of 1000-0.0001 μg/mL for 30 hours. The effect of each treatment on proliferation of HSC was assessed using the CyQUANT Direct Cell Proliferation Assay kit (Invitrogen) according to the manufacturer's instructions.

Effect on HSC Activation and Immunostaining for alpha Smooth Muscle Actin. Early passage HSCs were (P2) were grown at 6000 cells/well seeding density grown on fibrillar collagen coated plates as previously described and activated in culture by overnight treatment with 10 ng/mL of TGF-β1. The cells were then exposed to low serum medium containing Compound 1B or Compound 2B at a concentration range of 6000-0.0001 μg/mL for 30 hours. Following 30 hours of treatment, cells were fixed with 4% formaldehyde for 10 minutes, washed with PBS and then permeabilized with 0.1% Triton X-100 for 7 minutes. The cells were then blocked overnight with 1% BSA, 10% normal goat serum, 0.3 M glycine in 0.1% PBS-Tween. For alpha smooth muscle actin staining, all the samples were incubated overnight at 4° C. with anti-alpha smooth muscle actin antibody (Abcam) diluted 200 fold. The samples were then washed with PBS 4 times for 5 minutes each. Following this, the samples were counterstained using Alexa Fluor 633 secondary antibody for 2 hours, and then washed with PBS 4 times for 5 minutes each. The cells were then imaged using an EVOS fluorescence microscope (ThermoFisher Scientific).

Platelet flow Assay. Ibidi μ-Slide VI 0.1 (Ibidi) channels were coated with Fibrillar Type I Collagen (Chrono-Log Corp) at 100 μg/mL for 1 hour. Channels were then rinsed with PBS. Human blood used for the assay was collected in sodium citrate vacutainers from a consented donor following an approved IRB protocol. Freshly collected blood was stained with Calcein AM (Invitrogen) diluted 400 fold for 30 minutes. Compound 1B or Compound 2B was added to the pre-stained blood at 100 μg/mL and blood was flowed across each channel at a sheer rate of $1000^{-1s}$ for 10 minutes. After flow, the channels were rinsed of all visible traces of blood and imaged using an EVOS fluorescence microscope (ThermoFisher Scientific).

Results

Cell proliferation assay. At the highest concentration tested, of 1 mg/mL, for Compound 1B and Compound 2B HSC proliferation is approximately inhibited by 60%. Both conjugates inhibit proliferation in a dose dependent manner.

Figure 7:
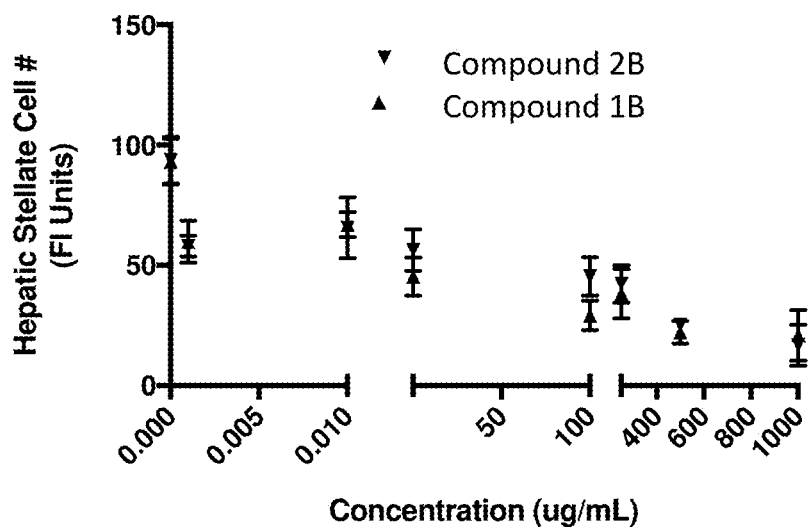

Effect on HSC Activation and Immunostaining for alpha Smooth Muscle Actin. In chronic liver disease TGF-β1 is the dominant stimulus for activation of HSCs to a myofibroblast phenotype. Activated HSCs can be identified by the expression of alpha Smooth Muscle Actin as shown in the images for the Control group. At the highest concentration tested, of 6 mg/mL, treatment of activated HSCs with Compound 1B and Compound 2B resulted in reduction of alpha Smooth Muscle Actin staining (FIG. 7).

Figure 6:
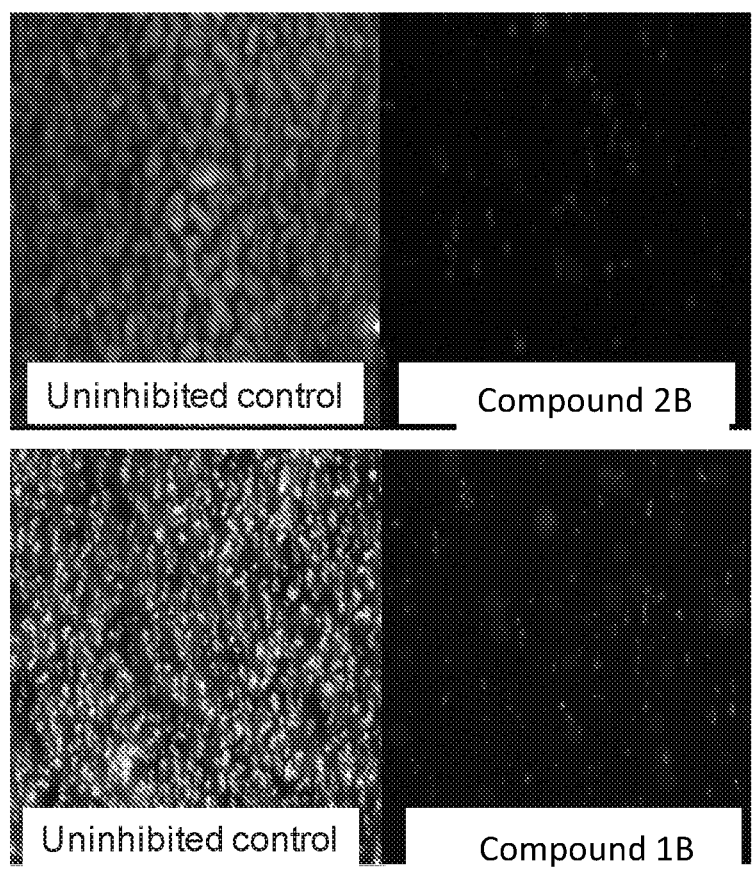
FIGS. 6 and 7 show platelet inhibition and hepatic stellate cell inhibition data for Compounds 1 and 2.

Platelet flow Assay. Fluorescence images show platelet-binding and inhibition by Compound 1B and Compound 2B at 100 μg/mL under whole blood flow. Channel 1 (uninhibited control), with no treatment was nearly completely covered with bound platelets whereas channels treated with the conjugates had significantly reduced number of platelets bound (FIG. 6).

The bioconjugates as described herein surprisingly showed anti-fibrotic and anti-proliferation effects on hepatic stellate cells, showing that the chemical modification with sulfates and peptides does not significantly diminish the biological effect.

Example 4: Carbon Tetrachloride Model

The ability of the compounds described herein to affect liver fibrosis was tested in a mouse model using carbon tetrachloride ($CCl_4$) as a toxic insult. C57BL/6 mice received twice per week intraperitoneal administration of 100 µL of 5% $CCl_4$ in mineral oil for 4 weeks total. During the same 4 week period, animals received intravenous administration of either saline (vehicle) or test article (Compound 1) 3 times per week. One group of animals received oral administration of Valsartan daily. Finally, a healthy group of animals that did not receive any test article or $CCL_4$ served as a normal control group.

Figure 2:
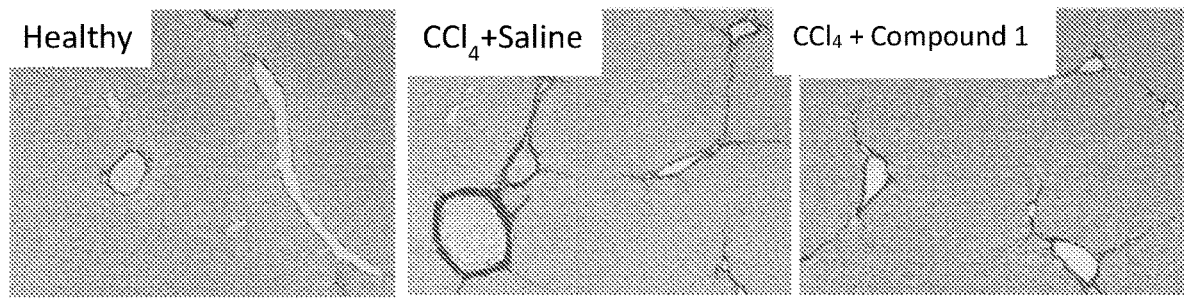
FIG. 2 shows the Sirius Red staining of livers in $CCl_4$ model.
Figure 3:
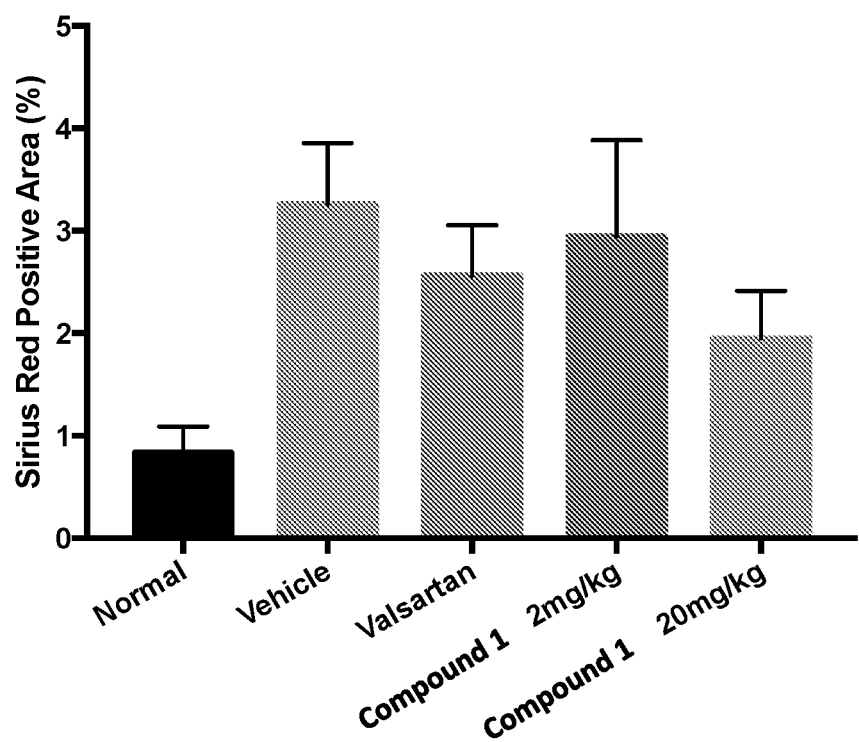
FIG. 3 shows the collagen content in the liver as measured histologically by Sirius Red staining for two doses of Compound 1 compared to Valsartan.

At the end of the 4-week period the animals were sacrificed and the livers were collected for biochemical and histological analysis. Hydroxyproline levels are shown in FIG. 1. $CCl_4$ administration increased hydroxyproline levels compared to the normal healthy animals. Treatment with Compound 1 at 20 mg/kg reduced the hydroxyproline levels to a statistically significant degree (p<0.05). Histological analysis of the livers for collagen content was performed using Sirius Red staining. FIG. 2 shows representative images of the liver sections, with increased collagen staining in vehicle treated group compared to normal healthy animals, and reduced collagen staining with compound treatment. The staining was quantified and presented in FIG. 3. $CCl_4$ increased the levels of collagen in the liver as measured histologically by Sirius Red. Treatment with Compound 1 significantly decreased the collagen staining compared to the vehicle control.

Example 5: Non-Alcoholic Steatohepatitis (NASH) Model

The ability of the compounds described herein to affect liver fibrosis was tested in a mouse model of Non-Alcoholic Steatohepatitis (NASH). C57BL/6 mice received a single subcutaneous injection of 200 ug streptozotocin after birth. Beginning at 4 weeks of age, animals were fed a high fat diet. Beginning at week 5 and continuing for 4 weeks until week 9, animals received 3x/week intravenous treatment with saline or Compound 1. A separate group of animals received daily oral administration of Telmisartan during the same period. Animals were sacrificed at 9 weeks of age and the livers were collected for histological and biochemical analysis.

Figure 4:
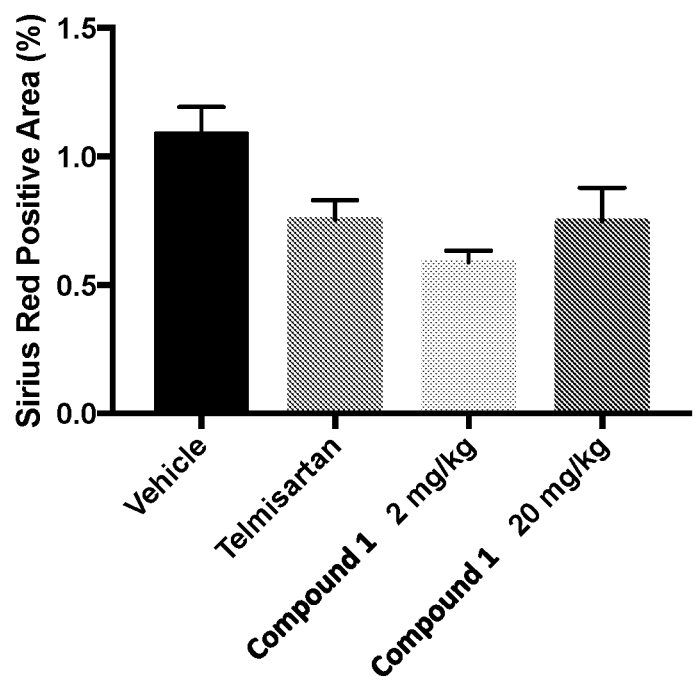
FIG. 4 shows collagen content in the liver as measured histologically by Sirius Red for two doses of Compound 1 compared to Telmisartan.

Histological analysis of the livers for collagen content was performed using Sirius Red staining. The staining was quantified and presented in FIG. 4. Treatment with Telmisartan or Compound 1 decreased levels of collagen in the liver compared to the vehicle treated group.

Figure 5:
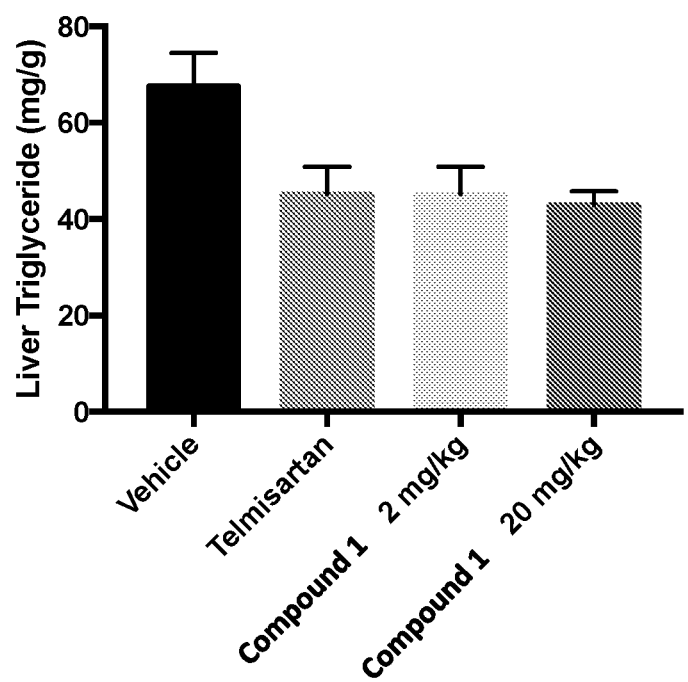
FIG. 5 shows liver triglyceride levels in animals at 9 weeks of age in the NASH model.

Liver triglycerides are shown in FIG. 5. Treatment with Telmisartan and Compound 1 decreased liver triglycerides during the study.

Distribution with In Vivo Imaging System

Figure 8:
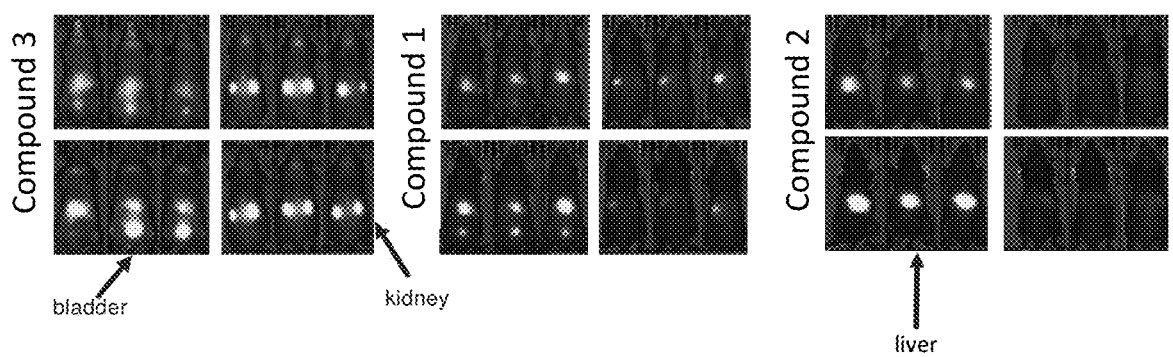
FIG. 8 shows IVIS imaging showing distribution of fluorescently labeled molecule (Compound 1, Compound 2 and Compound 3) in the kidneys, bladder, or liver. Top images were taken five minutes post IV injection, and bottom images were taken one hour post injection. Left images are the ventral side and right images are the dorsal side of the mice.

Molecules were synthesized with a fluorescent labeled. Specifically, CF633 was linked to the backbone via a hydrazide at a synthesis molar ratio of 1:1 dye to backbone. The molecules were intravenously dosed to nude mice at 10 mg/kg, and imaged using an In Vivo Imaging System (IVIS). At different time-points the animals were anesthetized and imaged using IVIS to determine biodistribution of the labeled compounds. FIG. 8 shows the localization of the compounds 5 or 60 minutes post injection. Localization in either the kidneys, bladder, or liver is demonstrated dependent on the molecular weight of the compound.

Differences in distribution of compounds were related to the molecular weight of the sHA backbone. The low molecular weight sHA (28 kDa) backbone (Compound 3) was observed in the kidneys, bladder, as well as the liver. In contrast, the higher molecular weight sHA (323 kDa) backbone (Compound 2) was only found to localize within the liver and did not show any signal in the bladder or kidneys. The sHA backbone of 163 kDa (Compound 1) was found to localize primarily within the liver, but also showed a slight signal within the bladder. These results demonstrate a surprising correlation between the molecular weight of the sHA backbone and distribution of the molecules when dosed IV, such that approximately 150 kDa molecular weight sHA is primarily excluded from the kidneys and instead localizes principally within the liver. Localization of sHA-peptide conjugates within the liver was also an unexpected finding given the unknown nature of the chemical modifications with sulfation and peptide conjugation on the parent HA backbone. Localization within the liver with relatively low distribution in other tissues or organs provides a unique opportunity to target diseases of the liver with an expected low systemic effect.

Example 6: VEGF Growth Factor Binding

VEGF189 (R&D Systems, 8147-VE) was coated onto a 96-well plate (Corning, 9018) by adding 75 µl of a 1 µg/ml solution in 1×PBS to each well and incubating overnight at 4C. Plates were washed 3 times using 300 µL of PBST (1×PBS with 0.02% Tween 20). Plates were then blocked with 1% BSA in PBS for 1 hour at room temperature. Biotinylated molecules were then dissolved in 1% BSA in PBST at 100 µg/mL, and serial dilutions of 1:10 were performed until reaching a final concentration of 0.1 ng/mL. 50 µL samples were then incubated on the plate for 1 hour at 37° C. Plates were then washed 3 times with 1% BSA in PBST and incubated with 100 µL of 1:500 Streptavidin-HRP (Thermo N504) in 1% BSA PBST for 20 minutes at room temperature. Plates were then washed 3 times with PBST and color was developed with 100 µl of 3,3',5,5'-tetramethylbenzidine (Abcam ab171527) for 10 minutes at room temperature, protected from light. The reaction was stopped by adding 100 µL 0.16 M sulfuric acid. Absorbance at 450 nm was read on a plate reader within 10 minutes.

Figure 9:
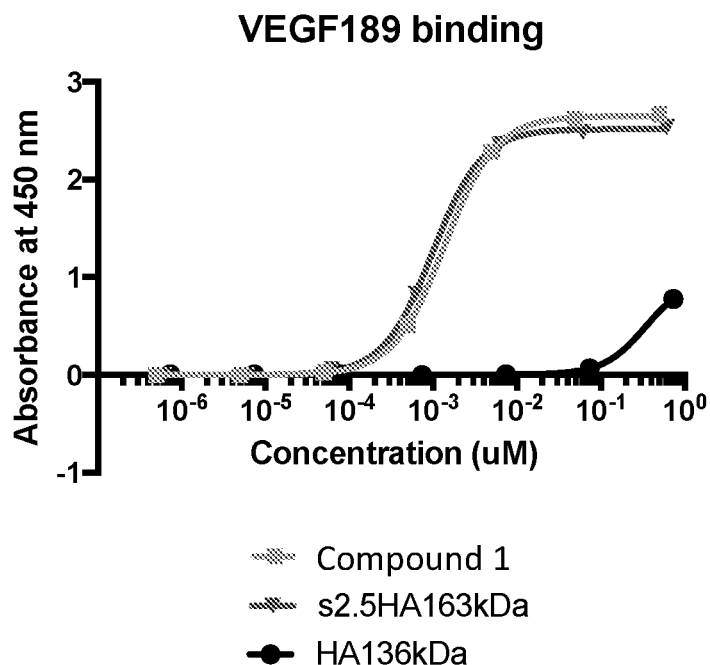
FIG. 9 shows binding of unfunctionalized HA, sulfated HA and Compound 1 to VEGF189.
Figure 10:
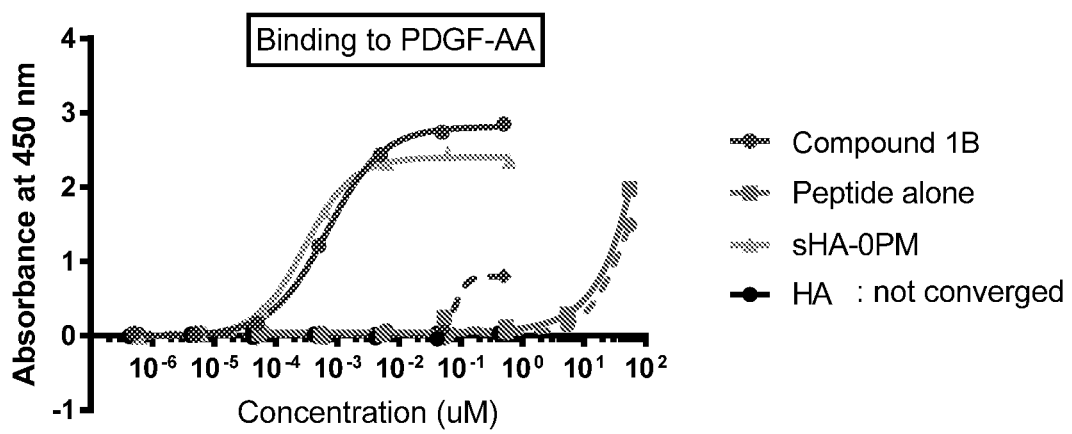
FIG. 10 shows the binding curve for Compound 1B, peptide alone, sHA-0PM and HA to PDGF-AA. Dashed lines indicate binding to non-coated wells at high molecule concentration (non-specific).
Figure 11:
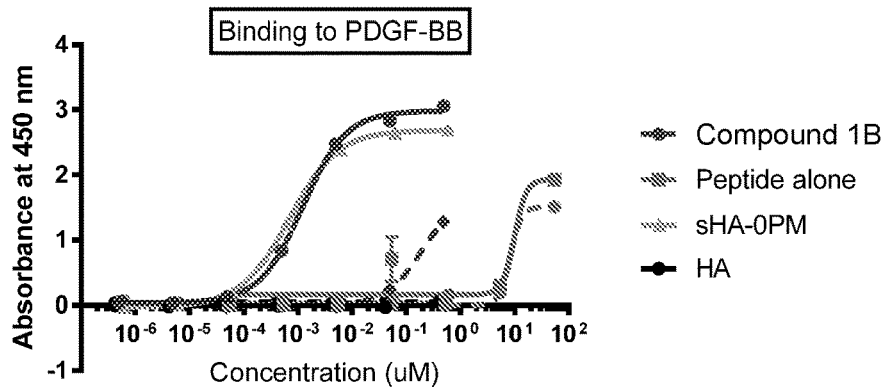
FIG. 11 shows the binding curve for Compound 1B, peptide alone, sHA-0PM and HA to PDGF-BB. Dashed lines indicate binding to non-coated wells at high molecule concentration (non-specific).
Figure 12:
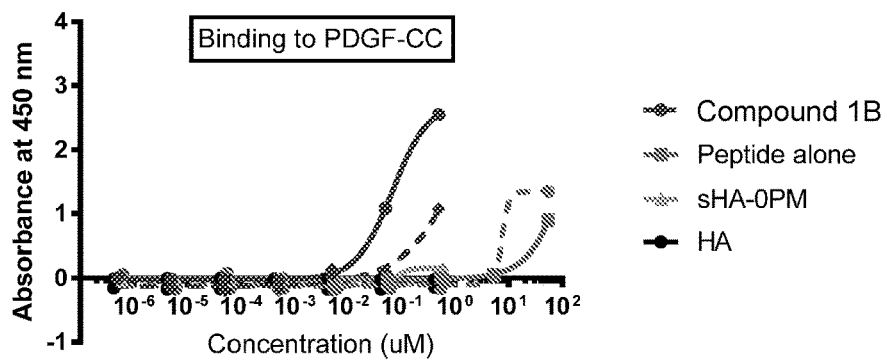
FIG. 12 shows the binding curve for Compound 1B, peptide alone, sHA-0PM and HA to PDGF-CC. Dashed lines indicate binding to non-coated wells at high molecule concentration (non-specific).
Figure 13:
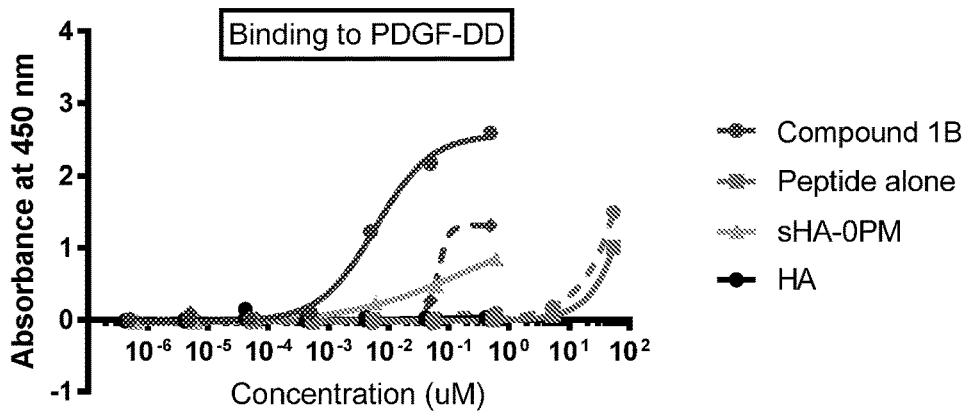
FIG. 13 shows the binding curve for Compound 1B, peptide alone, sHA-0PM and HA to PDGF-DD. Dashed lines indicate binding to non-coated wells at high molecule concentration (non-specific).

HA sulfated with 2.5 sulfate groups per disaccharide (s2.5HA, 163 kDa) was tested for binding to VEGF189 and an $EC_{50}$ of approximately 1 nM was observed (FIG. 9). A similar $EC_{50}$ value was observed when the same sulfated HA backbone was conjugated with peptide (Compound 1). However, HA of a similar MW that had not been sulfated did not bind to VEGF189. The same trend was also observed for an assay testing FGF2 binding. These data demonstrate that sulfation of HA enhances binding to growth factors and surprisingly the conjugation if sulfated HA with peptides does not decrease this binding.

Example 7: PDGF Growth Factor Binding

The following assays (growth factor binding and receptor engagement) assess various sulfated HA backbones for their ability to bind recombinant PDGF-BB, and interfere with its receptor engagement. PDGF-BB is a key inflammatory mediator found in fibrosis that triggers cell signaling by interacting with its receptor, PDGF-Rβ, on cell surface.

PDGF-BB's primary role is to promote migration and proliferation of HSCs. Also, activated HSCs (myofibroblasts) in both mice and humans have been shown to have a highly upregulated expression of PDGF-Rβ. Activated HSCs also produce PDGF-BB, resulting in an autocrine profibrotic loop. Lastly, PDGF-BB/PDGF-Rβ signaling synergistically regulates the profibrotic signaling of TGF-β. Both PDGF and TGF-β constitute important growth factors that mediate liver fibrosis.

The data provided herein demonstrates that Compound 1 inhibits the prominent growth factor isoform (PDGF-BB) and receptor (PDGF-Rβ) engagement. In addition Compound 1 also binds to other isoforms PDGF-AA, PDGF-CC, and PDGF-DD. Based on this data, it is contemplated that Compound 1 will inhibit receptor engagement by all PDGF isomers by binding and sequestering them.

Growth Factor Binding Assay Method

To determine the ability of Compound 1 to bind to all isomers of PDGF in vitro, an ELISA was developed using recombinant PDGF (AA, BB, CC, and DD) from R&D systems. Briefly, all four isomers of PDGF were reconstituted as per the manufacturer's protocol and adsorbed individually at a coating concentration of 1 μg/mL on Costar High Bind plates. Following overnight incubation at 4° C., any unbound PDGF was removed by rinsing with 1×PBS Tween (0.02%) wash buffer. Plates were then blocked with 1% BSA in 1×PBS for 1 hour at 25° C. Compound 1B (functionalized sHA with peptide load and biotin), zero peptide modification glycan backbone (sHA-0PM), or peptide alone—all labeled with biotin for detection—were serially diluted from 100 μg/mL to 0.0001 μg/mL in 1% BSA 1×PBS Tween (0.02%). Molecule dilutions were then added to PDGF-coated wells and incubated for 1 hour at 37° C. Following this, any unbound molecule was removed by rinsing plates three times with 1% BSA 1×PBS Tween (0.02%). Bound molecule with biotin label was then probed with streptavidin conjugated with horseradish peroxidase (HRP). After washing, plates were developed using tetramethylbenzidine (TMB) substrate and the reaction was stopped with acid solution. Plate well absorbances were measured at 450 nm using a Biotek Synergy H4 Multimode plate reader.

It has been observed that Compound 1B binds to all isoforms of PDGF to varying degrees in this in vitro assay (See FIGS. 10-13).

It was surprisingly found that the compound tested showed selectivity for certain isoforms, as is indicated by the $EC_{50}$s tabulated in Table 3. In summary, Compound 1B binds to PDGF-AA better than each of PDGF-BB, PDGF-DD, and PDGF-CC. It was also observed that sHA-0PM binds PDGF-AA better than PDGF-BB and PDGF-DD. PDGF-CC binding was not detected in this assay. Based on this study, non-sulfated HA and peptide alone do not bind to any PDGF isoform in vitro. In addition, conjugation of peptide to sHA improves binding to PDGF-CC and PDGF-DD when compared to functionalized sHA-0PM.

TABLE 3

$EC_{50}$ (μM) values for various PDGF isoforms in vitro.

| Molecules | PDGF-AA | PDGF-BB | PDGF-CC | PDGF-DD |
|---|---|---|---|---|
| Compound 1B | 0.00068 | 0.0012 | 0.069 | 0.0059 |
| sHA-0PM | 0.00029 | 0.0007 | — | 0.16 |

TABLE 3-continued $EC_{50}$ (μM) values for various PDGF isoforms in vitro.

| Molecules | PDGF-AA | PDGF-BB | PDGF-CC | PDGF-DD |
|---|---|---|---|---|
| Peptide alone | — | — | — | — |
| HA | — | — | — | — |

Growth Factor Receptor Engagement

Compound 1 or functionalized glycan backbone with different degrees of sulfation and/or peptide load (herein referred to as conjugates) were tested in a competitive ELISA assay designed to measure inhibition of PDGF-BB binding to PDGF-Rβ. Recombinant human PDGF-Rβ Fc chimera protein and biotin labeled PDGF-BB (R&D Systems) were reconstituted as per the manufacturer's protocol. PDGF-Rβ Fc chimera protein was adsorbed overnight at 4° C. onto Costar High Bind plates at a coating concentration of 1 nM. Unbound PDGF-Rβ Fc was removed by rinsing with 1×PBS Tween (0.02%) wash buffer following which the plate was blocked using 1% BSA in 1×PBS for 1 hour at 25° C. Compound 1 and conjugates were prepared at 2× concentration (Serial dilutions ranging from 4000 μg/mL to 0.002 μg/mL for result 1 and 2, at a single concentration 2 mg/mL (effective well concentration assayed=1 mg/mL) for result 3 below) in 1% BSA 1×PBS Tween (0.02%). PDGF-BB stock solution was also prepared at a 2× concentration of 20 ng/mL. Conjugates and PDGF-BB were mixed together 1:1 by incubating equal volumes of each for 30 minutes at room temperature. Pre-incubated solutions were then added to PDGF-Rβ Fc coated plate and allowed to bind for 1 hour at 37° C. Next, the plate was rinsed three times with 1% BSA 1×PBS Tween (0.02%). Bound biotin labeled PDGF-BB was detected using streptavidin conjugated with horseradish peroxidase (HRP). After washing, tetramethylbenzidine (TMB) substrate was added to wells to develop color. The reaction was stopped with acid solution and absorbance was measured at 450 nm using a Biotek Synergy H4 Multimode plate reader. More the inhibition, less PDGF-BB would be bound to the receptor on the plate and thus the signal read out would be lowered. Ratios of absorbance for conjugates to reference were recorded for result 3.

Figure 14:
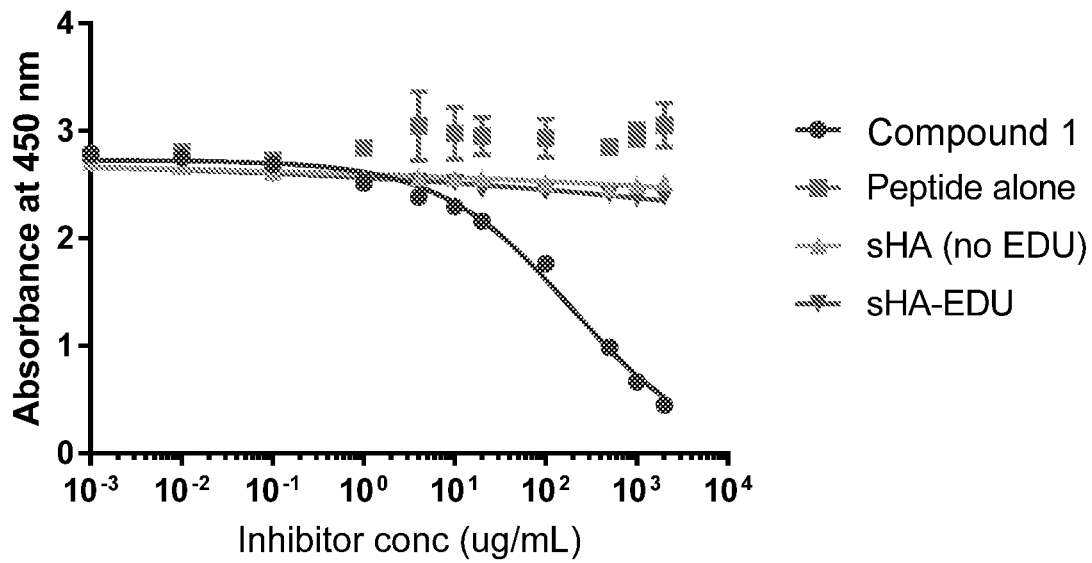
FIG. 14 shows PDGF-BB binding to its receptor PDGF-R$\beta$ in vitro in the presence of increasing amounts of Compound 1, peptide alone, sHA unfunctionalized or sHA functionalized (0PM).

Compound 1 (functionalized sHA with 30 peptide load, resulting in approximately 8, or 8-12% peptide functionalization) inhibits PDGF-BB (ligand) binding to its receptor, PDGF-Rβ, in vitro (FIG. 14). It is contemplated that the average number of peptides conjugated to glycan is less than indicated under "Peptide load". For example, it is believed that the average number of peptides conjugated to glycan in the 30PM conjugates may be about 20-25 peptides per glycan, corresponding to about 8-12% modification. Surprisingly, sHA (functionalized or unfunctionalized) does not inhibit this. Previously, in FIG. 11, it was shown that functionalized sHA-0PM binds PDGF-BB in vitro. However, binding of sHA-0PM to PDGF-BB does not seem to interfere with its receptor interaction based on the data in FIG. 14.

Figure 15:
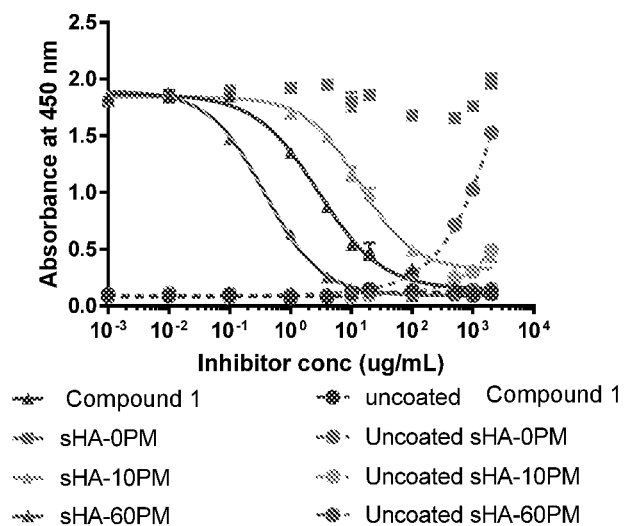
FIG. 15 shows PDGF-BB binding to its receptor PDGF-R$\beta$ in vitro in the presence of increasing amounts of Compound 1 of varying peptide load.

It has also been shown that increasing peptide load on functionalized sHA increases its ability to inhibit binding of PDGF-BB to its receptor in vitro (FIG. 15).

These results show that the degree of sulfation of functionalized HA influences its ability to interfere with receptor engagement of PDGF-BB in the in vitro assay. In general, at the same peptide load increasing degrees of sulfation increases inhibition of PDGF-BB binding to its receptor in vitro. As tabulated below, the inhibition by compounds having 2.3-2.4 degrees of sulfation exceeded that of compounds having 1.4 or 0 degrees of sulfation.

It was also found that as peptide load increased, the inhibition of PDGF-BB binding to its receptor improved, further corroborating the findings above.

Table 4 shows ratios of Absorbance 450 conjugate/Absorbance 450 reference. The bolded entries show similar or better binding of PDGF-BB to receptor when compared to similar amount of reference Compound 1 in the reaction. Shaded cells indicate higher inhibition or reduced binding of PDGF-BB to receptor.

TABLE 4

| Peptide | HA108 backbone | | | | HA163 backbone s2.5HA |
|---|---|---|---|---|---|
| load | HA | s1.4HA | s2.3HA | s2.4HA | |
| No EDU | — | — | — | — | 12.49 |
| 0PM | 17.27 | 12.66 | 11.46 | 11.36 | 16.40 |
| 10PM | 16.96 | 15.05 | 7.18 | 7.46 | 4.82 |
| 20PM | 16.33 | 12.83 | 5.17 | 4.11 | — |
| 30PM | 14.18 | 13.33 | 2.64 | 5.18 | — |
| 50PM | 9.31 | 13.42 | 1.48 | 1.52 | — |
| 60PM | — | — | — | — | 0.53 |

Example 8: Thioacetamide (TAA) Model

Severe liver fibrosis was induced in rats by the toxin thioacetamide, dosed 3 times per week IP at a concentration between 100 and 150 mg/kg for 8 total weeks. Beginning at week 5, test article dosing of either compound 1 at 3 different doses or sHA-0PM (no peptide) was started, delivered IV once per week. At the end of the 8 weeks animals were sacrificed. Plasma was collected and measured for liver biomarkers. Livers were separated for biochemical analysis of total collagen as measured by hydroxyproline, or processed for histology to assess fibrosis by Sirius Red staining.

Figure 16:
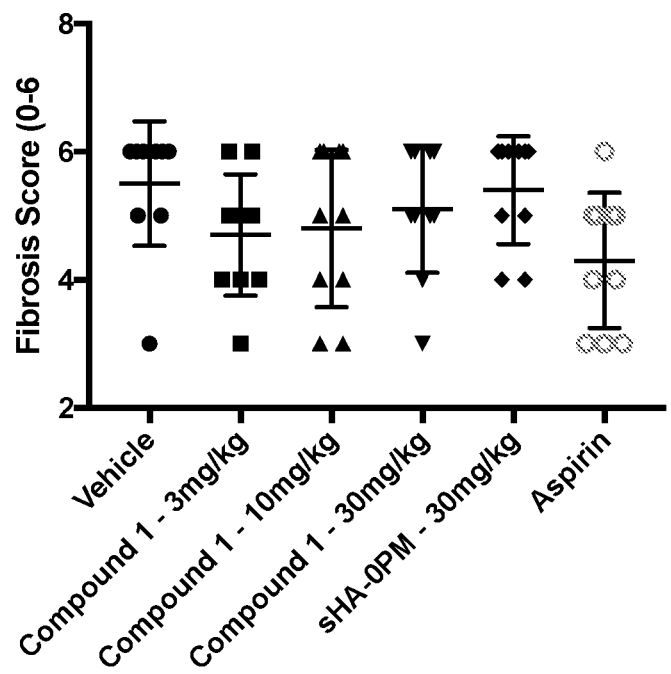
FIG. 16 shows reduced occurrence of high fibrosis scores compared to vehicle treated animals.

Fibrosis was scored histologically using a scale from 0-6, with 0 indicating no fibrosis and 6 indicating severe fibrosis. 70% of the animals treated with a vehicle control were ranked at the highest level of fibrosis, indicating the severity of the model. Treatment with Compound reduced the occurrence of high fibrosis scores compared to vehicle treated animals (FIG. 16). This reduction in fibrosis occurred in all doses of compound 1 tested, with a general trend towards a reverse dose response. Dosing of sHA-0PM resulted in some reduction in fibrosis scores, but less so than Compound 1. Additionally, aspirin was used as a positive control for platelet inhibition, and its use resulted in decreased fibrosis scores.

Figure 17:
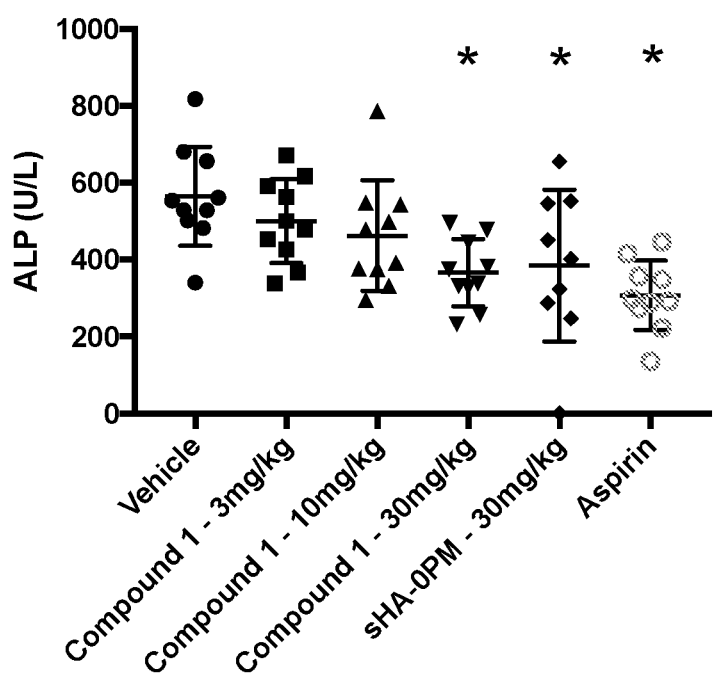
FIG. 17 shows that after two weeks of test article dosing, serum levels of alkaline phosphatase (ALP) was significantly reduced with treatment of 30 mg/kg Compound 1.

Serum levels of alkaline phosphatase (ALP) were also measured during the study. ALP is typically used as a measure of cholestatic or metabolic liver injury. After two weeks of test article dosing, ALP was significantly reduced with treatment of 30 mg/kg Compound 1 (FIG. 17), however lower doses of Compound 1 did not have a significant effect on ALP. sHA-0PM did significantly lower ALP. This effect on ALP occurred mid-way through the treatment period, but in this severe model did not remain sustained throughout the study. Reduction in ALP levels was not an expected outcome in the model. Additionally, the dose dependent effect in ALP levels mid-way through the study is unexpectedly counter to the inverse dose response found in fibrosis score at the study endpoint.

Additional fibrosis data may include quantifying the amount of fibrosis, either through histological quantification of collagen staining, or in biochemical analysis of collagen in the liver. It is expected that Compound 1 will reduce these measures of collagen. Additionally, Compound 1 may also reduce the mRNA levels of collagen, as well as serum levels of pro-collagen III, as has been seen with treatment of Compound 1 in other more mild fibrosis models (carbon tetrachloride model). Further, Compound 1 may reduce other biomarkers of fibrosis, such as PDGFRb, alpha smooth muscle actin, or any other marker known to be associated with fibrosis.

Example 9: Sulfation Study

Collagen I Binding Assay

Rat tail monomeric collagen I (Corning) was diluted to a working concentration of 50 µg/mL using 0.2 N glacial acetic acid. Costar High Bind plates were overnight at 4° C. with the diluted rat tail collagen I. Unbound collagen was removed by rinsing with 1×PBS Tween (0.05%) wash buffer following which the plates were blocked using 1% BSA in 1×PBST (0.05%) for 1 hour at 25° C. Serial dilutions of Compound 1 and bioconjugates with varying degrees of sulfation and peptide loads (Table 5) were prepared at 2× concentrations ranging from 4000 µg/mL to 0.064 µg/mL in 1% BSA 1×PBST (0.05%). Biotin tagged Compound 1B stock solution was also prepared at a 2× concentration of 8 µg/mL. Test bioconjugates and Compound 1B were combined in a 1:1 volume ratio and incubated for 5 minutes at room temperature. Pre-incubated solutions were then added to collagen coated plates and allowed to bind for 15 minutes at 25° C. Plates were rinsed three times with 1×PBST (0.05%) and blocked with 5% BSA in 1×PBST (0.05%) for 1 hour at 25° C. Compound 1B was detected using streptavidin conjugated with horse-radish peroxidase (HRP). After washing, tetramethylbenzidine (TMB) substrate was added to wells to develop color. The reaction was stopped with acid solution and absorbance was measured at 450 nm using a Biotek Synergy H4 Multimode plate reader.

TABLE 5

| | Peptide load | | | | |
|---|---|---|---|---|---|
| DOS | 0 | 10 | 20 | 30 | 50 |
| 0 | 27.78 | 14.76 | 2.82 | 13.41 | 7.49 |
| 1.4 | 1000 | 161.28 | 1000 | 1.96 | 1000 |
| 2.3 | 53.88 | 1000 | 4.90 | 0.79 | 0.80 |
| 2.4 | 42.19 | 1000 | 0.50 | 0.43 | 0.25 |

Table 5, above, shows ratios of $IC_{50\,sample}/IC_{50\,Compound\,1}$ from competitive collagen I binding assay. Ratios≤1 demonstrate binding similar to or stronger than Compound 1. Ratios>1 demonstrates binding to collagen that is weaker than Compound 1. The data shows that collagen binding increases with increasing peptide load and that for degree of sulfation 2.3 and 2.4, increasing the peptide per backbone demonstrates binding to collagen similar to that seen with Compound 1. This demonstrates that both degree of sulfation (DOS) and peptide load play a synergistic role in determining binding to collagen.

Hepatic Stellate Cell Proliferation Assay A

This study demonstrates the effect of Compound 1 and bioconjugates with varying degrees of sulfation and peptide load on hepatic stellate cell (HSC) proliferation. Primary human Hepatic Stellate Cells (HSC) were obtained from ScienCell Research Labs (San Diego, CA, USA). These cells were provided at passage 1, thus exhibited an activated phenotype. The cells were expanded on Poly-L-lysine coated T-75 flasks in medium provided by ScienCell Research Labs containing 2% fetal calf serum in a humidified atmosphere containing 95% air, 5% $CO_2$. Cells were grown to 75-80% confluence and cryopreserved at P2 for use in all experiments.

Tissue culture treated 96 well μ-Plate (Ibidi) were coated with 50 μg/mL of Chrono-Par Fibrillar Collagen I for 2 hours in a humidified atmosphere containing 95% air, 5% $CO_2$. Following the 2 hour incubation, plates were manually rinsed with sterile 1×PBS to remove any excess fibrillar collagen. Plates were then pre-incubated with 30 μL per well of medium provided by ScienCell Research Labs containing 0.5% fetal calf serum. P2 cryopreserved cells were thawed and reconstituted in the same low serum-containing medium for the experiment. Cells were seeded onto the fibrillar collagen coated wells at a seeding density of 6000 cells in 30 μL per well and allowed to attach for 2-3 hours. Cell attachment was confirmed by imaging with a Leica phase contrast microscope. TGF-β (R&D Systems) was reconstituted as per the manufacturer's protocol. 30 μL per well of TGF-β at 30 ng/mL was then added to each well and plates were incubated overnight in a humidified atmosphere containing 95% air, 5% $CO_2$. Stock solutions of Compound 1 and conjugates with varying degrees of sulfation and peptide loads were prepared at concentrations of 1000, 100, 10, and 1 μg/mL. After 20 hours of TGF-β stimulation, medium was replaced with 80 μL per well of prepared dilutions. Negative controls wells were treated with 80 μL per well of low serum medium. Cells were allowed to grow for 48 hours in a humidified atmosphere containing 95% air, 5% $CO_2$. Cell proliferation was assessed at 48 hours using CyQuant Direct Assay kit. Fluorescence intensity measurements were recorded using Molecular Devices M5 multimode plate reader.

Figure 18:
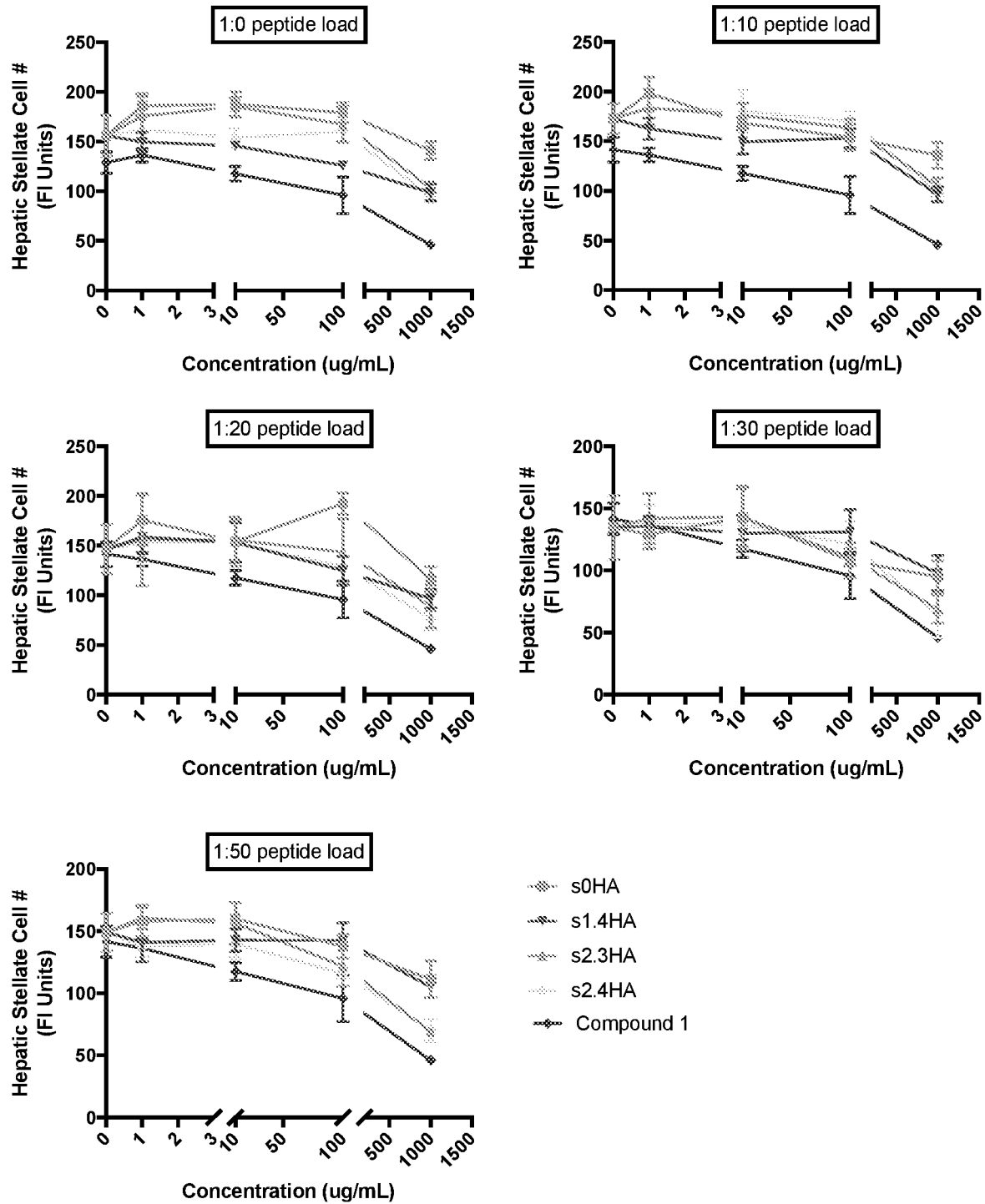
FIG. 18 shows a dose range study demonstrating effect of Compound 1 and bioconjugates with varying degrees of sulfation and peptide load on hepatic stellate cell (HSC) proliferation.

HA backbones with degrees of sulfation ranging from zero (s0HA), 1.4 (s1.4HA), 2.3 (s2.3HA), and 2.4 (s2.4HA) were synthesized and conjugated with peptide loads 0, 10, 20, 30, or 50. Compound 1 consists of HA backbone with a degree of sulfation of 2.5 and peptide load of 30 peptides. As can be seen in FIG. 18, both degree of sulfation and peptide load have a synergistic effect on inhibiting proliferation of HSCs. Low degree of sulfation with low peptide load does not inhibit as well as Compound 1, whereas increasing the peptide load on conjugates with lower degree of sulfation restores its ability to inhibit proliferation.

Table 6 shows the percent inhibition of HSC proliferation by Compound 1 and bioconjugates with varying degrees of sulfation (DOS) and peptide load tested at a concentration of 1000 μg/mL.

TABLE 6

| DOS | Peptide Load | | | | |
|---|---|---|---|---|---|
| | 0 | 10 | 20 | 30 | 50 |
| 0 | 9.57 | 21.25 | 20.51 | 29.46 | 25.53 |
| 1.4 | 36.69 | 44.11 | 34.10 | 27.20 | 29.52 |
| 2.3 | 33.66 | 38.89 | 39.31 | 48.82 | 53.70 |
| 2.4 | 38.96 | 42.12 | 47.51 | 51.62 | 52.85 |
| 2.5 | x | x | x | 64.25 | x |

The data shows that increasing the degree of sulfation of the HA backbone increases the backbone mediated inhibition of HSC proliferation. For degree of sulfation 2.3 and 2.4, increasing the peptide load results in inhibition of HSC proliferation similar to that observed by Compound 1. This demonstrates that both degree of sulfation and peptide load have a synergistic role in determining the biological activity.

Hepatic Stellate Cell Proliferation Assay B

This study shows that backbone with no chemical modification (non-sulfated HA) inhibits HSC proliferation similar to Compound 1. Primary human HSCs were obtained from ScienCell Research Labs (San Diego, CA, USA). These cells were provided at passage 1, thus exhibited an activated phenotype. The cells were expanded on Poly-L-lysine coated T-75 flasks in medium provided by ScienCell Research Labs containing 2% fetal calf serum in a humidified atmosphere containing 95% air, 5% $CO_2$. Cells were grown to 75-80% confluence and cryopreserved at P2 for use in all experiments.

Tissue culture treated Costar 96 well was coated with 50 μg/mL of Chrono-Par Fibrillar Collagen I for 2 hours in a humidified atmosphere containing 95% air, 5% $CO_2$. Following the 2 hour incubation, plate was manually rinsed with sterile 1×PBS to remove any excess fibrillar collagen. The plate was then pre-incubated with 100 μL per well of medium provided by ScienCell Research Labs containing 0.5% fetal calf serum. P2 cryopreserved cells were thawed and reconstituted in the same low serum-containing medium for the experiment. Cells were seeded onto the fibrillar collagen coated wells at a seeding density of 6000 cells in 100 μL per well and allowed to attach for 2-3 hours. Cell attachment was confirmed by imaging with a Leica phase contrast microscope. TGF-β (R&D Systems) was reconstituted as per the manufacturer's protocol. 100 μL per well of TGF-β at 30 ng/mL was then added to each well and plate was incubated overnight in a humidified atmosphere containing 95% air, 5% $CO_2$. Stock solutions of Compound 1 and modified and no modification backbone were prepared at concentrations ranging from 1000 to 0.001 μg/mL. After 20 hours of TGF-β stimulation, medium was replaced with 200 μL per well of prepared dilutions. Negative controls wells were treated with 200 μL per well of low serum medium. Cells were allowed to grow for 48 hours in a humidified atmosphere containing 95% air, 5% $CO_2$. Cell proliferation was assessed at 48 hours using CyQuant Direct Assay kit. Fluorescence intensity measurements were recorded using Molecular Devices M5 multimode plate reader.

Figure 19:
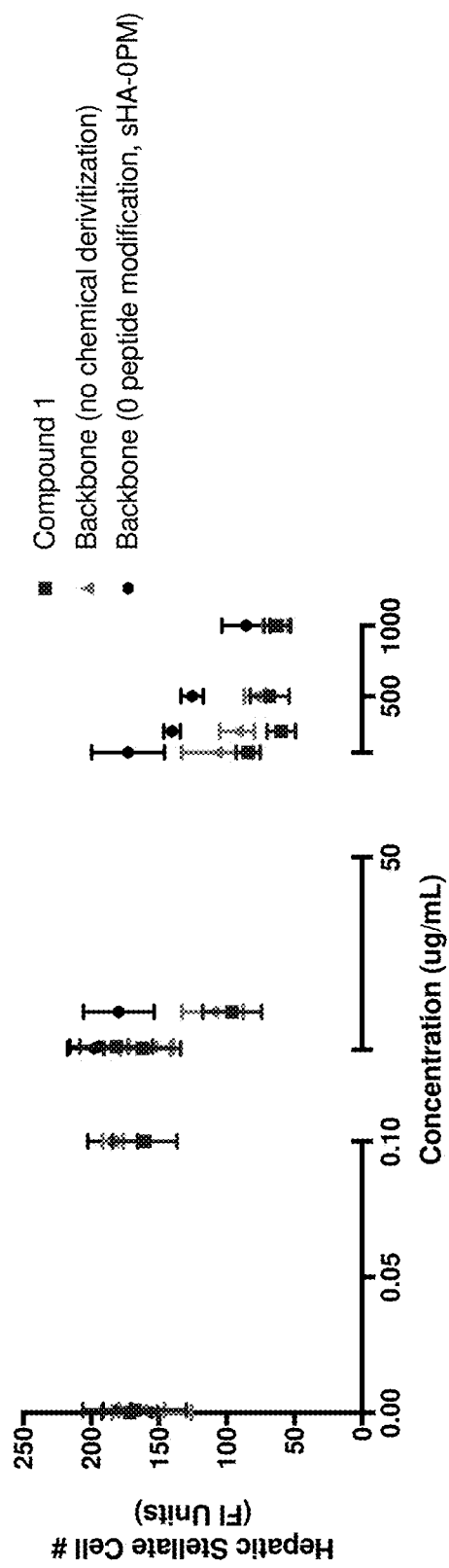
FIG. 19 shows a dose range study demonstrating effect of Compound 1, backbone (no chemical derivatization, i.e., sulfation), and backbone (0 peptide modification, "sHA-0PM") on hepatic stellate cell (HSC) proliferation.

FIG. 19 shows a dose range study demonstrating effect of Compound 1, backbone (no chemical derivatization, i.e., sulfation), and backbone (0 peptide modification, "sHA-0PM") on hepatic stellate cell (HSC) proliferation. Backbone with no chemical modification inhibits HSC proliferation similar to Compound 1. Sulfation of the HA backbone diminishes its ability to inhibit HSC proliferation. The addition of peptides to the sulfated backbone (e.g., Compound 1) restores the loss of biological activity. Therefore, both peptide load and degree of sulfation of the HA backbone play a synergistic role in inhibiting HSC proliferation.

What is claimed is:

1. A bioconjugate comprising at least one peptide(s), wherein the at least one peptide(s) comprises a collagen-binding unit covalently bonded to a chemically sulfated hyaluronic acid,
    wherein the chemically sulfated hyaluronic acid has a molecular weight greater than about 150 kDa,
    wherein the chemically sulfated hyaluronic acid comprises from 15 to 30 percent (%) functionalization with peptides,
    wherein the chemically sulfated hyaluronic acid has been chemically sulfated to a degree of sulfation of from about 2.0 to about 3.0, and
    wherein the at least one peptide(s) comprises the amino acid sequence of SEQ ID NO: 17.

2. The bioconjugate of claim 1, wherein the chemically sulfated hyaluronic acid has a molecular weight of from about 150 to about 750 kDa.

3. The bioconjugate of claim 1, wherein the chemically sulfated hyaluronic acid has a molecular weight of from about 200 to about 400 kDa.

4. The bioconjugate of claim 1, wherein the collagen-binding unit of the peptide(s) bind to collagen with a dissociation constant ($K_d$) of less than about 1 mM.

5. The bioconjugate of claim 1, wherein the peptide(s) comprise up to about 120 amino acids.

6. The bioconjugate of claim 1, wherein the chemically sulfated hyaluronic acid does not contain oxidatively cleaved saccharide units.

7. A composition comprising the bioconjugate of claim 1, wherein the average number of peptide(s) per chemically sulfated hyaluronic acid is from about 50 to about 150.

8. A composition comprising the bioconjugate of claim 1, wherein the average number of peptide(s) per chemically sulfated hyaluronic acid is about 100.

* * * * *